United States Patent [19]
Czeisler et al.

[11] Patent Number: 5,163,426
[45] Date of Patent: Nov. 17, 1992

[54] ASSESSMENT AND MODIFICATION OF A SUBJECT'S ENDOGENOUS CIRCADIAN CYCLE

[75] Inventors: Charles A. Czeisler; Richard E. Kronauer, both of Cambridge, Mass.; James S. Allan, Pittsburgh, Pa.

[73] Assignee: Brigham and Women's Hospital, Boston, Mass.

[21] Appl. No.: 66,677

[22] Filed: Jun. 26, 1987

[51] Int. Cl.$^5$ .............................. A61N 5/06
[52] U.S. Cl. ................................... 128/395
[58] Field of Search .............................. 364/413, 414; 128/395–398

[56] References Cited

U.S. PATENT DOCUMENTS

| | | |
|---|---|---|
| 628,351 | 7/1899 | O'Neill . |
| 720,357 | 2/1903 | Joachimson . |
| 730,750 | 6/1903 | Dowsing . |
| 791,232 | 5/1905 | Wolpers et al. . |
| 828,733 | 8/1906 | Fuller . |
| 853,033 | 5/1907 | Roberts . |
| 1,162,424 | 11/1915 | Wiener . |
| 1,222,945 | 4/1917 | Hammerstein . |
| 1,280,857 | 8/1918 | Ruiter . |
| 1,290,036 | 1/1919 | Anderson . |
| 1,337,798 | 4/1920 | Ruiter . |
| 1,563,736 | 12/1925 | Fink . |
| 1,564,552 | 12/1925 | Gerdes . |
| 1,578,654 | 3/1926 | Gerdes . |
| 1,583,420 | 5/1926 | Picard . |
| 1,718,770 | 6/1929 | Zublin . |
| 1,755,418 | 4/1930 | Anderson . |
| 1,842,100 | 1/1932 | Johnson . |
| 1,859,601 | 5/1932 | Rice . |
| 1,951,569 | 3/1934 | Vestvold . |
| 2,008,653 | 7/1935 | Braselton . |
| 2,054,332 | 9/1936 | Lower et al. . |
| 2,114,173 | 4/1938 | Boerstler . |
| 2,184,644 | 12/1939 | Homberger . |
| 2,444,379 | 6/1948 | Sexton . |
| 2,631,588 | 3/1953 | Paschell . |
| 3,042,046 | 7/1962 | Willems . |
| 3,648,706 | 3/1972 | Holzer . |
| 3,773,049 | 11/1973 | Rabichev et al. . |
| 4,100,415 | 7/1978 | Blaisdell et al. . |
| 4,335,724 | 6/1982 | Frei et al. . |

(List continued on next page.)

OTHER PUBLICATIONS

"Entrainment of Human Circadian Rhythms by Light–Dark Cycles: A Reassessment," Ceizler et al., *American Society for Photobiology*, Printed by University of Vermont, 1978, p. 73.

(List continued on next page.)

*Primary Examiner*—Ruth S. Smith
*Attorney, Agent, or Firm*—Sterne, Kessler, Goldstein & Fox

[57] ABSTRACT

A method for accurately assessing and rapidly modifying the phase and amplitude of the endogenous circadian pacemaker is disclosed. A circadian cycle modification capacity assessment method comprises (before and after a stimulus) eliminating activity-related confounding factors associated with the sleep-rest cycle which otherwise mask the state of the endogenous circadian pacemaker. Based on either individual or normative assessment data, the circadian phase and amplitude modification method involves the application of bright (about 9,500 lux) light and, advantageously, episodes of imposed darkness, at critically chosen phases to achieve rapid and stable changes in phase and amplitude. The timing of the episodes of bright light may be chosen either by reference to empirically-derived phase response data, or by using a mathematical model in which the endogenous circadian pacemaker is a van der Pol oscillator. A forcing function in the model is substantially proportional to changes in the cube root of the surrounding illuminance, in lux. The amplitude of the endogenous circadian pacemaker may actually be reduced to substantially zero, so as to bring about dramatic phase modifications in diminishingly small periods of time. The methods find special utility in treating "jet lag" sufferers, shift workers, advanced circadian phase experienced by many elderly subjects, and those afflicted with delayed sleep phase insomnia.

26 Claims, 40 Drawing Sheets

U.S. PATENT DOCUMENTS

| | | |
|---|---|---|
| 4,424,598 | 1/1984 | Cima . |
| 4,444,189 | 4/1984 | Seiverd . |
| 4,469,102 | 9/1984 | Fish . |
| 4,469,951 | 9/1984 | Coco et al. . |
| 4,543,957 | 10/1985 | Friedman et al. . |
| 4,600,723 | 7/1986 | Short et al. . |
| 4,665,086 | 5/1987 | Short . |

OTHER PUBLICATIONS

"Human Circadian Rhythms: A Multioscillatory System," Aschoff et al., *Federation Proceedings*, vol. 35, 1976, pp. 2326–2332.

"Bright Light Improves the Entrainment of Circadian Rhythm of Body Temperature to a 26-Hour Sleep--Wake Cycle in Humans," Eastman, *Sleep Research*, 1986, p. 271.

*Overcoming Jet Lag*, Ehret et al., Berkley Books (New York), 1983, 160 pages.

"Phase Response of Human Melatonin Rhythms to Bright Light in Antarctica," Arendt et al., *Journal of Physiology*, vol. 377, 1986, p. 68.

"Bright White Light Alleviates Depression", Kripke et al., *Psychiatry Research*, vol. 10, 1983, pp. 105–112.

"Bright Light Resets the Human Circadian Pacemaker Independent of the Timing of the Sleep-Wake Cycle", Czeisler et al., *Science*, vol. 233, Aug. 1986, pp. 667–671.

"Moonlight and Circadian Rhythms", Sinclair, and Response by Czeisler et al., *Science*, vol. 235, Jan. 1987, p. 145.

"Human Sleep: Its Duration and Organization Depend on Its Circadian Phase," Czeisler et al., *Science*, vol. 210, 1980, pp. 1264–1267.

"Scheduled Exposure to Daylight: A Potential Strategy to Reduce Jet Lag Following Transmeridian Flight," Daan, et. al., *Psychopharmacology Bulletin*, vol. 20, No. 3 (1984) pp. 566–568.

"Strength of a Light-Dark Cycle as a Zeitgeber for Circadian Rhythms in Man," Ruetger Wever, *Pfluegers Arch.* 321, pp. 133–142 (1970).

"Circadian Wortham Amplitude and Individual Ability to Adjust to Shift-Work," Reinberg et al., *Ergonomics*, vol. 21, No. 10 (1978) pp. 763–766.

"Rotating Shift Work Schedules That Disrupt Sleep Are Improved by Applying Circadian Principals," Czeisler et al., *Science*, vol. 217, No. 4558, (1982) pp. 460–463.

Lewy, A. J., Wehr, T. A., et al., "Light suppresses melatonin secretion in humans", *Science* 1980; 210: 1267–1269.

"The Use of Bright Light in the Treatment of Chronobiologic Sleep and Mood Disorders: The Phase-Response Curve," Goodwin and Lewy, *Psychopharmacology Bulletin*, vol. 19, No. 3, 1983, pp. 523–525.

"Immediate and Delayed Effects of Bright Light on Human Melatonin Production: Shifting Dawn and Dusk Shifts Dim Light Melatonin Onset," Lewy et al. *Annals New York Academy of Sciences*, 1985, pp. 253–259.

"Antidepressant and Circadian Phase-Shifting Effects of Light," Lewy et al., *Science*, vol. 235, pp. 352–354.

"Phase-Dependent Responses of Human Circadian Rhythms to a Bright Light Pulse: Experiments in a Temporal Isolation Unit," Honma et al., *J. Physiol. Soc. Japan*, 1986, p. 416.

"Sleep Deprivation In Constant Light Phase Advance Shifts and Shortens the Free-Running Period of the Human Circadian Timing System," Czeisler et al., *Sleep Research*, vol. 14, p. 252, 1985.

"A Method for Quantifying phase position of the Deep Circadian Oscillator and Determining a Confidence Interval", Brown et al., *Sleep Research*, vol. 14, 1985, p. 290.

"Entrainment of Human Circadian Rhythms by Light--Dark Cycles: A Reassessment," Czeisler et al., *Photochemistry and Photobiology*, vol. 34, 1981, pp. 239–247.

"A Functional Analysis of Circadian Pacemakers in Nocturnal Rodents, II. The Variability of Phase Response Curves," Daan et al., *Journal of Comparative Physiology*, vol. 106, 1976, pp. 253–266.

*The Geometry of Biological Time*, Winfree, Springer-Verlag, 1980, pp. 36–38, 53.

"Circadian Rhythms: Entrainment by Light and Temperature" (Chapter 3), Saunders, *An Introduction To Biological Rhythms*, Blackie, 1977, pp. 40–64.

"Light Effects on Circadian Timing System of a Diurnal Primate, the Squirrel Monkey" Hoban et al., *American Journal of Physiology*, vol. 249, 1985, pp. R274–R280.

(List continued on next page.)

OTHER PUBLICATIONS

"Circadian Rhythms and Performance Decrements in the Transportation Industry", Czeisler et al., *Proceedings of a Workshop on the Effects of Automation on Operator Performance*, Coblenz, A. M., ed., Commission Des Communautes Europeenes, Programme De Recherche Medicale et de Sante Publique, Universite Rene Descartes: Paris, 1986, pp. 146-171.

"Mathematical Model of the Human Circadian System With Two Interacting Oscillators," Kronauer et al., *American Journal of Physiology*, vol. 242, 1982, pp. R3-R17.

"To Honor Fechner and Repeal His Law," Stevens, *Science*, vol. 133, 1961, pp. 80-86.

"A Clinical Method to Assess the Endogenous Circadian Phase (ECP) of the Deep Circadian Oscillator in Man," Czeisler et al., *Sleep Research*, vol. 14, 1985, p. 295.

"Bright Light Affects Human Circadian Rhythms," Wever et al., *European Journal of Physiology*, Pfluegers Archiv, vol. 396, 1983, pp. 85-87.

"Use of Light to Treat Jet Lag: Differential Effects of Normal and Bright Artificial Light on Human Circadian Rhythms," Wever, *Annals New York Academy of Sciences, Part III, Health Effects of Interior Lighting*, 1985, pp. 282-304.

"Chronotherapy: Resetting the Circadian Clocks of Patients with Delayed Sleep Phase Insomnia," Czeisler et al., *Sleep*, vol. 4, No. 1 (1981) pp. 1-11.

"Insomnia During the 'Dark Period' In Northern Norway," Lingjaerde et al., *Acta Psychiatr. Scand.*, vol. 71, 1985, pp. 506-512.

"Treatment of Appropriately Phase Typed Sleep Disorders Using Properly Timed Bright Light," Lewy et al., *Sleep Research*, 1985, p. 304.

"A 2-Oscillator Model Derived from Free-running Circadian Rhythms Accurately Predicts Range of Zietgeber Entrainment," Kronauer et al., *Sleep Research*, vol. 12, 1983, p. 368.

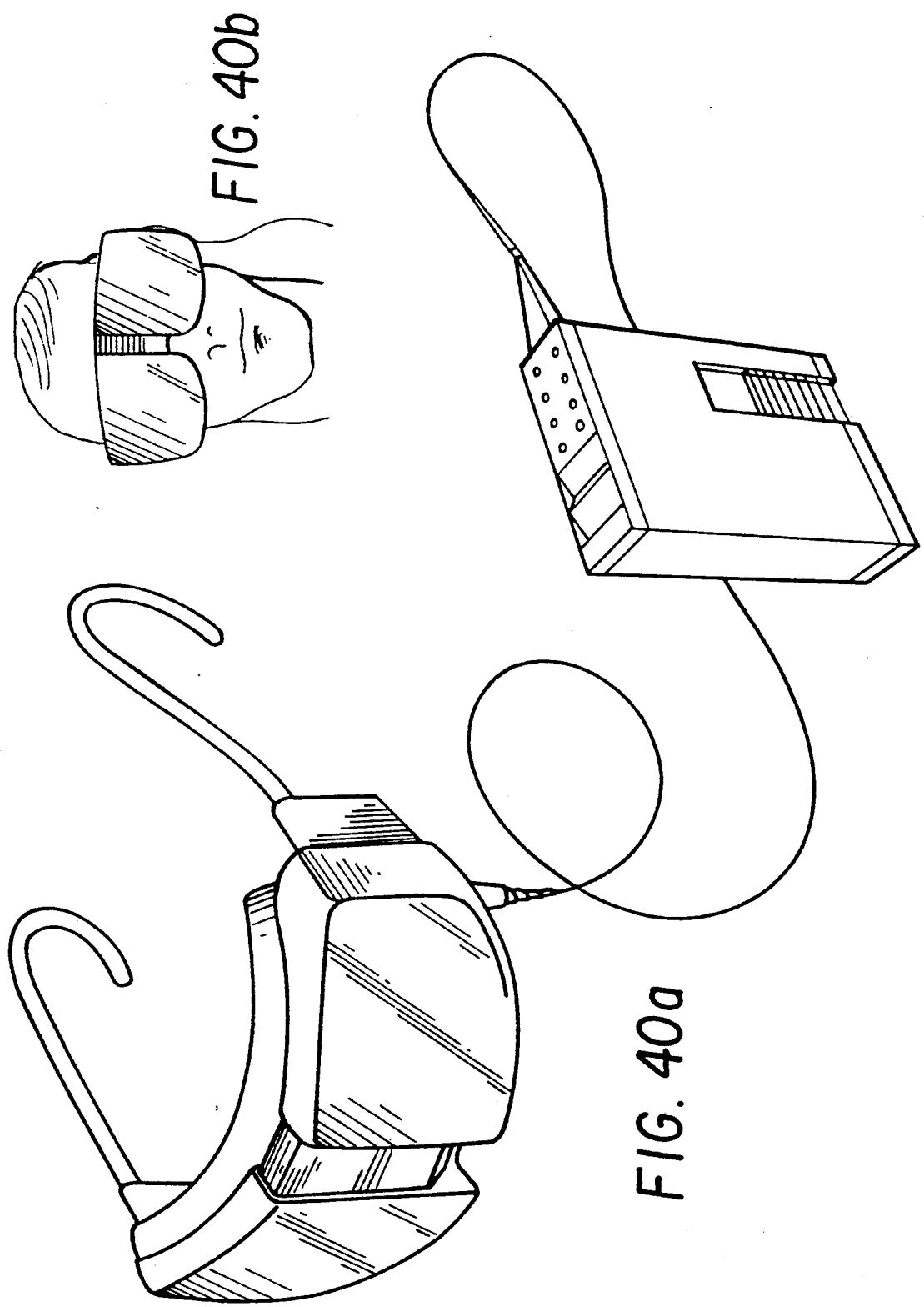

ASSESSMENT AND MODIFICATION OF A SUBJECT'S ENDOGENOUS CIRCADIAN CYCLE

BACKGROUND OF THE INVENTION

1. Field of the Invention

This invention relates to methods and devices for assessing and modifying the circadian cycle in humans. More specifically, the invention relates to methods and devices for using scheduled exposure to bright light, and advantageously also periods of darkness, to alter the circadian cycle of humans to a desired phase and amplitude.

2. Related Art

It is known in the art that humans exhibit circadian (daily) cycles in a variety of physiologic, cognitive, and behavioral functions. The cycles are driven by an internal biological clock or circadian pacemaker which has been located in the brain and are not just passive responses to periodic environmental changes. It is known that humans exhibit different degrees of alertness, performance, and proneness to accidents at different phases in their circadian cycle.

Often, the activities in which humans wish to engage do not coincide in time with the most appropriate point in the circadian cycle. For instance, transmeridian travelers experience what is commonly referred to as "jet lag." This phenomenon occurs when the internal, physiological circadian phase of the traveler has not yet adapted to the geophysical time of his destination. Individuals who travel from west to east often experience sleeplessness late in the evening at their destination, with a corresponding difficulty in awakening on time in the morning. Similarly, those who travel from east to west often experience a tendency to sleep earlier in the evening and arise earlier in the morning than is appropriate for the locale of their destination. The travelers' internal, physiological cycle lags (or leads) their desired activity-rest cycle. Symptoms are worse and last longer when travelers must cross more than three or four time zones, especially when traveling west to east. West to east travel is more difficult than east to west travel because the intrinsic period of the human circadian pacemaker is greater than 24 hours (averaging about 24.3 to 25.0 hours in normal young men). Therefore, in the absence of an environmental synchronizing cue, the phase position of the pacemaker tends to drift to a later hour (i.e., in a manner equivalent to westward travel at a rate of about one time zone per 2 days). The insomnia associated with jet lag may be postponed two or three days if the travelers are sleep-deprived as a result of the journey, since sleep deprivation makes it easier to sleep at any circadian phase. However, the essential circadian nature of jet lag is demonstrated by nocturnal insomnia and excessive daytime sleepiness which typically occur within two to three days of arrival.

In a similar fashion, people who work in professions requiring them to work at night, such as factory workers, medical personnel police, and public utilities personnel, experience a desynchrony between the activities in which they desire to engage and their physiological ability to engage in such activities. Such "shift workers" often experience an inability to sleep soundly during their non-working hours. This misalignment between internal circadian phase and scheduled work hours at night also manifests as increased drowsiness during the early morning hours of 3:00–7:00 a.m., assuming a habitual waketime of 7:00 to 8:00 a.m. (These times would be modified if the habitual waketime were at a different hour.) It is during this time frame that most people's circadian cycles are at their troughs, implying that they experience minimum alertness and maximum proneness to accident or error. These workers then experience corresponding difficulty sleeping during the daytime hours after they have worked at night, again because of circadian phase misalignment. This results in sleep deprivation, which exacerbates the problem they experience with alertness and performance on their subsequent night shifts. For workers in the medical field or for those individuals who monitor the processes in nuclear power plants, for example, such decreased alertness can have (and already may have had) disastrous consequences.

Two different approaches have been used previously to reduce the deleterious effects of shift work schedules on the performance of shift workers and the safety of shift work operations. One, used primarily in Europe, has been to select those workers with a reduced amplitude of the temperature cycle for shift work, since it has been reported that individuals with a lower temperature cycle amplitude can adapt more easily to rotating shift work schedules (see A. Reinberg et al., "Circadian Rhythm Amplitude and Individual Ability to Adjust to Shift Work." *Ergonomics,* Vol. 21 (1978), pp. 763–766). The second approach has been to apply circadian principles in the design of work schedules (see C. A. Czeisler et al., "Rotating Shift Work Schedules That Disrupt Sleep Are Improved by Applying Circadian Principles." *Science,* Vol. 210 (1980), pp. 1264–1276).

There are various categories of sleep-related and affective disorders which are thought to be related to misalignment between the internal circadian cycle and the external activity-rest cycle. For example, the elderly often experience a phase advance of the internal circadian pacemaker to an earlier hour, which manifests as a tendency to be fatigued and tired earlier in the evening, and to spontaneously awake earlier in the morning, than was the case earlier in their lives. Many elderly subjects also have a reduced amplitude of the endogenous component of the body temperature cycle, suggesting that the output of the circadian pacemaker may be attenuated with age. This may contribute to the increased tendency for both daytime napping and nocturnal arousals reported in the elderly.

Other sleep scheduling disorders not totally determined by age, such as delayed-sleep-phase insomnia, are also known. Finally, the misalignment between the internal circadian cycle and the external activity-rest cycle may contribute to certain affective disorders, including depression.

Various techniques have been attempted in the past to correct the above-noted abnormalities in phase or amplitude of the circadian system. In the case of activity-induced phase misalignment or desynchronization, as in the case of transmeridian travelers and shift workers, the goal of the methods was to facilitate the speedy adjustment to the "destination" place or time. In the case of non-activity-induced phase misalignment, such as age-related circadian phase advance and delayed sleep phase insomnia, the goal of the methods was to provide prompt and stable adjustment of the circadian phase to match the desired activity-rest (sleep-wake) cycle. These various alleged phase-shifting techniques involved special diets, drugs, exercise, or direct manipulation of the sleep-wake cycle. For various reasons, such as the presence of side effects, impracticality of implementation and/or simple ineffectiveness, such techniques have not found practical utility. No techniques to date have allowed rapid and efficient circadian phase-shifting.

Other researchers have employed the application of light to phase-shift the circadian cycle of humans. At first, it had been thought that humans were the exception in the animal kingdom to the rule that light provided a means by which the internal circadian phase was directly synchronized to the external periodic environmental cycle. Although later research showed that human circadian cycles appeared to respond to timed application of light, the researchers who attempted to determine the effects of light on human circadian cycles were confounded by the lack of an accurate means of assessing the circadian phase and amplitude resetting capacity of a given human subject. Without being able to rapidly assess the phase and amplitude of an experimental subject before and after a series of applications of light, researchers were unable to accurately determine the effect of those applications of light.

It is therefore desirable to design a reliable and accurate method of assessing the effect of a particular stimulus on human circadian phase and amplitude in a reasonably short period of time. Such an accurate and efficient circadian phase and amplitude assessment method would allow accurate measurement of the effects of different exposures to light on phase and amplitude modification.

An early method of assessing the phase-shifting effect of a particular stimulus on the circadian phase of lower animals was embodied in procedures carried out to derive a hypothetical construct called a Phase Response Curve (PRC), developed in early experiments conducted by Hastings and Sweeney, DeCoursey et al., and Pittendrigh et al. See Czeisler et al., "Chronotherapy: Resetting the Circadian Clocks of Patients with Delayed Sleep Phase Insomnia," *Sleep*, Vol. 4, No. 1 (1981), pp. 1–21. See also Lewy et al., "The Use of Bright Light in the Treatment of Chronobiologic Sleep and Mood Disorders: The Phase Response Curve," *Psychopharmacology Bulletin*, Vol. 19, No. 3 (1983), pp. 523–25. The PRC was based on early research on nocturnal animals which spent most, if not virtually all, of the duration of the experiment in total darkness. When in total darkness, circadian rhythms "free-run" since they lack any means by which they may be "reset" to the 24-hour geophysical day. The results of such experiments are therefore of limited usefulness in determining the effect of a more complex lighting schedule which includes exposure to bright light, ordinary indoor light, and darkness, in causing phase shifts and amplitude changes in the internal physiological circadian cycle of humans. Also, humans cannot practically be expected to spend weeks in total darkness punctuated by occasional episodes of bright light.

It was known that the core body temperature of humans varied with the circadian cycle. By observing subjects who were placed in isolation from any external time cues (or "zeitgebers") for a time period on the order of 30 days, researchers could monitor the core body temperature to discern a long-term trend to the troughs of the body temperature cycle. The long-term trend of body temperature troughs was used to determine (using, for example, Fourier analysis) the period of the "free-running" cycle of the individual subject. Furthermore, about one quarter of the subjects studied in these long-term studies exhibited an activity-rest cycle which was desynchronized from the period of the body temperature cycle (spontaneous internal desynchronization), thereby revealing the intrinsic period of the endogenous circadian pacemaker which drives the endogenous component of the body temperature cycle. This technique of period and phase determination will hereinafter be referred to as the desynchronized wave form eduction technique. (See S. H. Strogatz, *The Mathematical Structure of the Human Sleep-Wake Cycle, Lectural Notes in Biomathematics No. 69*, Heidelberg, FRG: Springer-Verlag, 1986). Although this method's validity was enhanced by the later-demonstrated stability of the period of the internal circadian cycle, the 1–2 month length and cost of this assessment technique rendered it impractical for all clinical applications and even many laboratory experiments. Unfortunately, such lengthy and costly experiments were once necessary to eliminate the confounding effects of activity on the body temperature cycle. However, for statistical reasons, the inaccuracies of the phase determinations incorporated in this 1–2 month desynchronized waveform eduction technique for period and phase assessment are the greatest at the beginning and the end of the study. The desynchronized waveform eduction technique is therefore neither practical nor useful for determining the phase-shifting effect of a particular stimulus delivered between two such (30–60 day) phase assessment procedures.

Lewy et al. later attempted to use melatonin as an indicator of circadian phase, based on the observation that light above a certain brightness threshold (2500 lux) suppresses the secretion of melatonin. See Lewy et al., "Immediate and Delayed Effects of Bright Light on Human Melatonin Production: Shifting 'Dawn' and 'Dusk' Shifts the Dim Light Melatonin Onset," *Annals New York Academy of Sciences*, 1985, pp. 253–59. However, no reliable correlation has yet been shown between melatonin secretion levels and the phase or amplitude of the endogenous circadian cycle using generally accepted techniques such as the desynchronized waveform eduction technique. Furthermore, the shifts reported by that method were modest, and required an impractically large number of treatments. Daily exposure to light treatments for one week were typically required to achieve a 1- or 2-hour phase shift. (See A. J. Lewy et al., "Antidepressant and Circadian Phase-Shifting Effects of Light", *Science*, Vol. 235, pp. 352–54 (1987). See also Honma, K., Honma, S., Wada, T., "Phase Dependent Responses of Human Circadian Rhythms to a Bright Pulse: Experiments in a Temporal Isolation Unit", *J. Physol. Soc. Jap.*, Vol. 48, p. 416 (1986).)

SUMMARY OF THE INVENTION

The present invention is a method for rapidly adjusting the phase and amplitude of the output of the human circadian pacemaker (also called the endogenous (or deep) circadian oscillator, "x" oscillator, or the internal clock) by scheduled exposure to light and, advantageously, also darkness. While there have been a variety of theories on how to achieve such shifts, none of these methods had practical utility without a means of calibrating the strength or effectiveness of the stimulus suggested. An essential component of the present invention is therefore a newly developed method to assess the response of the circadian system to an intervention stimulus. Also, a set of functions relating the timing and intensity of bright-light exposure, and advantageously also the timing of darkness, to the amount by which the circadian pacemaker is adjusted or modified, has been experimentally derived.

The present invention is premised on the observed results that light has a direct effect on the endogenous circadian pacemaker, and that the strength of that effect depends on the timing, intensity and duration of light exposure. Indeed, in most subjects, exposure to bright light is required to rapidly shift the endogenous circadian pacemaker, but the timing of darkness/sleep determines in part the magnitude and, in some instances, the direction, of the shift induced by bright light exposure at a given phase.

The invention comprises an accurate assessment of phase and amplitude resetting capacity, and an efficient means of adjustment of human circadian rhythms. The assessment method involves elimination of the confounding effects of the activity-rest behavioral cycle and light-dark cycle before and after the intervention, and, advantageously, scheduling the sleep/dark time such that the most stimulus-sensitive phase of the circadian system is accessible for exposure to bright light. Confounding effects which are eliminated include timing of sleep episodes, food ingestion, posture, and physical activity. When these confounding factors have been removed, an accurate physiological assessment of the endogenous circadian phase and amplitude of the subject is performed in a comparatively short period of time. Assessment may be followed by administration of a particular stimulus, such as a regimen of light exposure and darkness, at specific circadian phases, derived from the pre-treatment phase assessment data. After the administration of the stimulus, the circadian phase and amplitude assessment may be repeated. The difference between the pre-treatment and post-treatment endogenous phase and amplitude assessments reveals the effect of the stimulus administered.

Based on this assessment of phase and amplitude resetting capacity, the method of administering a regimen of bright light (and advantageously also darkness) according to the present invention efficiently adjusts the circadian phase to a new, desired phase and amplitude. This adjustment is based on application of bright light at critically chosen phases in the existing circadian cycle. The adjustment of the phase is enhanced and stabilized by also choosing periods of darkness to be in proper time relation to the application of the light pulses.

The invention advantageously increases the efficiency of acute phase adjustments by altering the amplitude of the circadian cycle, in addition to adjusting the phase. The amplitude is decreased to magnify the phase-shifting effect of a subsequent bright light application. Reducing amplitude near zero to facilitate rapid phase shifts is analogous to positioning oneself near the North or South Pole to facilitate travel across time zones. At either pole, travel across many time zones can be achieved by taking a few steps, rather than the hundreds of miles required to cross a single time zone near the equator. By application of bright light at appropriate phases, the amplitude may even be reduced to zero. When the amplitude is zero, a succeeding light pulse instantly resets the circadian cycle to a desired phase. Conversely, the amplitude may be increased, for example, to improve quality of sleep and increase wakeful alertness.

The present invention envisions that, in many circumstances, the phase and amplitude may be individually modified without substantially affecting the other. For example, when the desired phase shifts are small (e.g., four hours or less), the timing of the bright light and darkness stimuli may be selected such that the phase shifting effects of the stimulus are maximized while maintaining the normal amplitude of the pacemaker output.

The present invention makes use of a mathematical model of this phase and amplitude resetting process with light. This model is derived from, and validated by, a large body of human research data. The model predicts the results of exposure to an even wider variety of additional lighting regimens.

Devices which facilitate the methods of application of bright light and darkness are within the scope of the invention. Also, computer-based methods automatically determine the correct amount of phase adjustment required to synchronize a subject's circadian cycle with a desired activity cycle, and "prescribe" a sequence of applications of bright light so as to achieve that phase adjustment.

One embodiment of the invention is a method of modifying a subject's circadian cycle to a desired state, comprising the steps of assessing characteristics of a present circadian cycle of the subject; and applying, at preselected times in the assessed present circadian cycle, pulses of bright light of preselected duration; whereby the characteristics of the present circadian cycle of the subject are rapidly modified to become the desired state of the subject's circadian cycle.

Another embodiment of the invention is a method of modifying a subject's circadian cycle to a desired state, comprising the steps of assessing characteristics of the present circadian cycle of the subject; applying, at preselected times in the assessed present circadian cycle, pulses of bright light and, optionally, pulses of imposed darkness, of preselected durations so as to modify the amplitude of the circadian cycle to be substantially zero; and applying a subsequent pulse of bright light at a preselected time to set the circadian cycle of the subject to the desired state.

Another embodiment of the invention is a method of assessing modification capacity of a stimulus on a subject's circadian cycles, comprising the steps of assessing characteristics of a pre-stimulus circadian cycle of the subject; applying the stimulus to the subject; and assessing characteristics of a post-stimulus circadian cycle of the subject. The assessing steps comprise placing the subject in a semi-recumbent position; minimizing the subject's physical activity; feeding the subject small amounts of food at regular, closely-timed intervals; keeping the subject awake; and measuring the characteristics of the circadian cycle by measuring physiological parameters of the subject.

Another embodiment of the invention is a method of modifying a subject's circadian cycle to a desired state, comprising the steps of assessing characteristics of a present circadian cycle of the subject; and applying, at preselected times in said assessed present circadian cycle, pulses of bright light and, optionally, pulses of imposed darkness, of preselected durations. The characteristics of the present circadian cycle of the subject are modified to become the desired state of the subject's circadian cycle. The assessing step comprises modelling the subject's circadian cycle as a solution to a van der Pol differential equation; whereby the preselected times and the preselected durations are selected.

Another embodiment of the invention is a method of modifying a subject's circadian cycle to a desired state, comprising the steps of assessing characteristics of a present circadian cycle of the subject; and applying, at preselected times in the assessed present circadian cycle, pulses of bright light and, optionally, pulses of imposed darkness, of preselected durations. The characteristics of the present circadian cycle of the subject are rapidly modified to become the desired state of the subject's circadian cycle. The assessing step comprises determining optimum bright light pulse onset times, and, optionally, imposed darkness pulse offset times, based on one or more empirically derived phase response curves.

Another embodiment of the invention is a method for stably synchronizing the circadian cycle of a subject to the subject's sleep/wake cycle, comprising the steps of exposing the subject's retinas to a normal range of illumination during waking hours of the subject; and imposing strict darkness on the subject's retinas during the sleeping hours of the subject; whereby the amplitude of subject's circadian cycle is increased.

Another embodiment of the invention is an apparatus for administering bright light to a subject's retina, comprising luminous means for controllably emitting bright light; aperture means, located relative to the luminous means for allowing the subject to view his environment even when the luminous means are emitting bright light. The apparatus may be self-supporting, or it may be in the form of portable light goggles.

Another embodiment of the invention is a computer apparatus for prescribing a substantially optimum stimulus regimen of bright light pulses, and, optionally, darkness pulses, to allow a subject's circadian cycle to be modified to a desired state. The apparatus comprises input means for inputting pre-stimulus timing data; assessing means for receiving the pre-stimulus timing data, and for assessing characteristics of the subject's circadian cycle; modelling means, connected to said assessing means, for computing substantially optimum durations and application times of the bright light pulses and, optionally, the darkness pulses; and output means, connected to the modelling means, for outputting the substantially optimum durations and application times.

In this disclosure, "pulse" need not be defined as of short duration. "Pulses" may be hours long.

BRIEF DESCRIPTION OF THE DRAWINGS

The invention is best understood and appreciated by reading the following detailed description with reference to the accompanying drawings, in which:

FIGS. 40a and 40b are sketches of a representative light goggle with peripheral hardware and software.

FIG. 40a shows application of the representative light goggle.

DETAILED DESCRIPTION OF THE PREFERRED EMBODIMENTS

Figure 1:
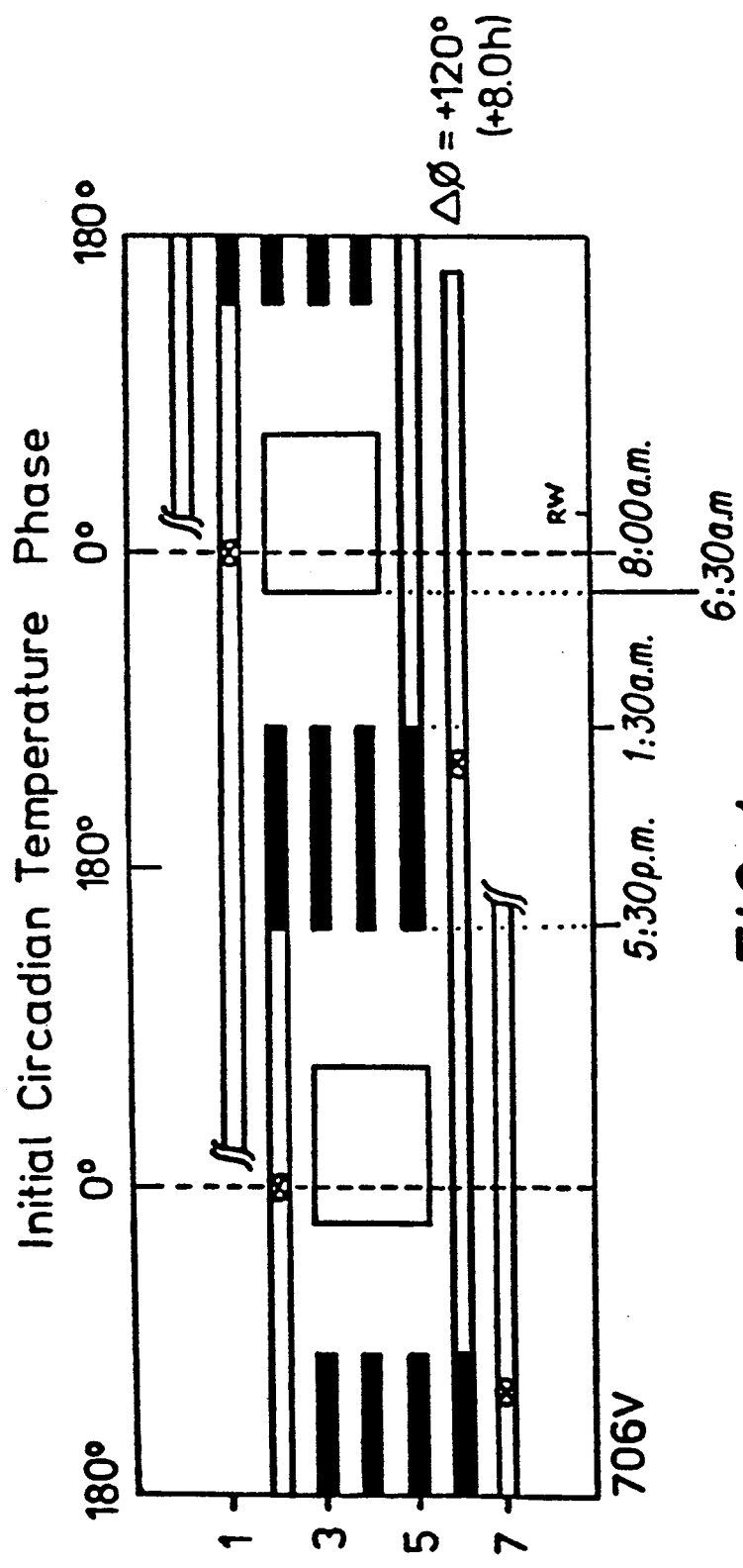
FIG. 1 shows a protocol for Evaluation of Circadian Phase and Amplitude Resetting Capacity.
Figure 2:
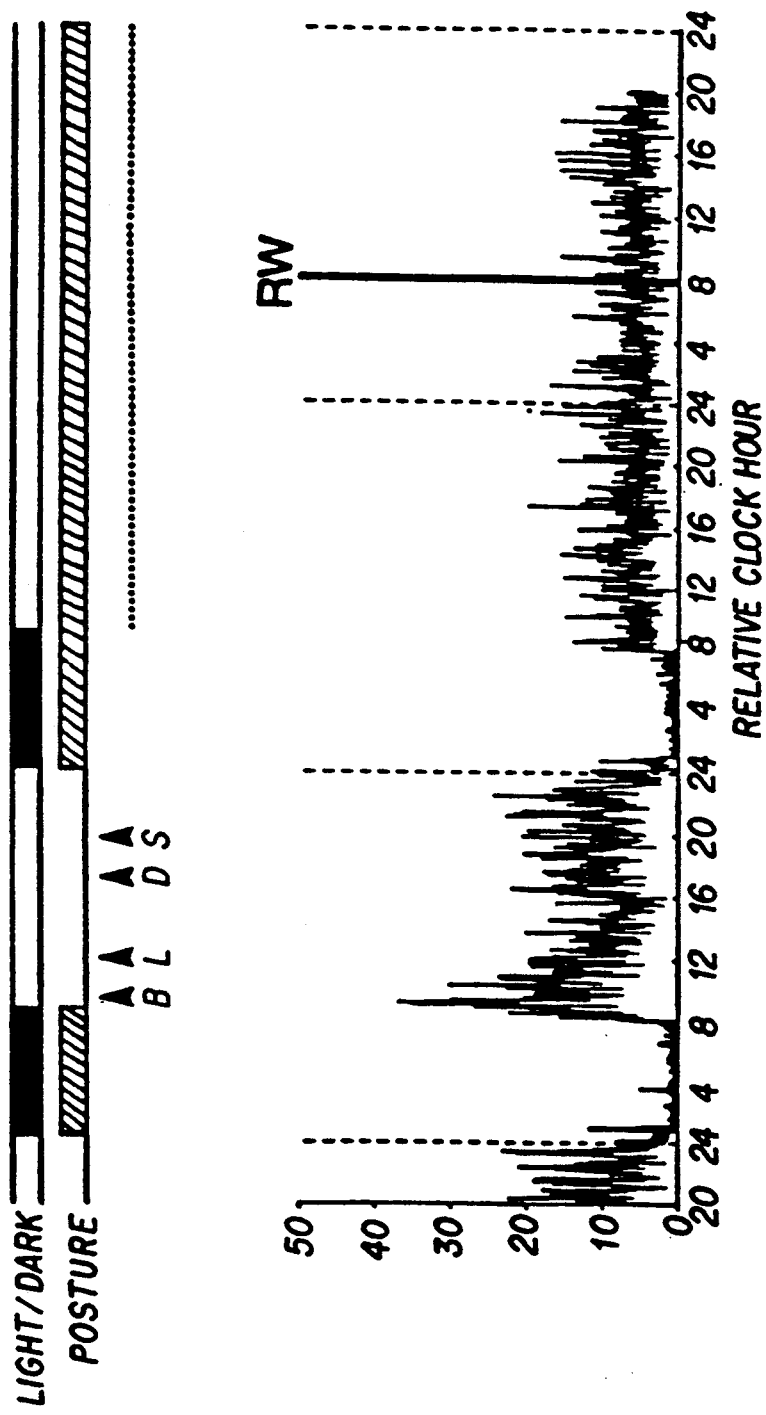
FIGS. 2A and 2B show a protocol to expose endogenous phase and amplitude by use of the Constant Routine.

A first method is directed to the accurate assessment of the phase and amplitude resetting capacity of the endogenous circadian pacemaker for a particular subject within a relatively short time frame. A second method is directed to the actual modification of the phase and/or amplitude of that pacemaker using scheduled periods of bright light, advantageously enhanced with manipulation of dark (rest) periods, based on either normative phase assessments or on a phase assessment of that individual subject. Phase and amplitude modification may be achieved based on either empirically derived normative data or based on a mathematical model, relating to the existing state of the deep circadian pacemaker. Finally, devices which facilitate the practice of the assessment and modification methods are described.

1. Foundations for the Inventive Techniques of Assessing Circadian Phase and Amplitude Resetting Capacity As stated above in the Background of the Invention, there have been a variety of lengthy techniques used to try to asses the phase resetting capacity of the circadian timing system, none of which was ideally suitable for use in humans. The most commonly used technique used in animal studies, delivery of a stimulus during a synchronized free-run, is an inadequate means of testing the response capacity of the circadian system to a signal. This is because after disturbance of the sleep-wake cycle the body temperature cycle would no longer oscillate at the compromise period it displays during a synchronized free run ($\tau_s$) which is longer than its intrinsic period ($\tau_x$), but would instead oscillate for 1-2 cycles at its intrinsic period. This would make most signals appear to cause a modest phase advance, as occurs in response to one night of sleep deprivation (see C. A. Czeisler et al., "Sleep Deprivation in Constant Light Phase Advance Shifts and Shortens the Free-Running Period of the Human Circadian Timing System," *Sleep Research*, Volume 14, p. 252. See also Honma, K., Honma, S., Wada, T., "Phase Dependent Responses of Human Circadian Rhythms to a Bright Pulse: Experiments in a Temporal Isolation Unit", *J. Physiol. Soc. Jap.*, Vol. 48, p. 416 (1986).).

Thus, we designed a technique to combine a method to rapidly assess the phase and amplitude of the endogenous circadian pacemaker before and after delivery of a stimulus protocol. With the stimulus protocol itself.

Presently, the most widely recognized method to assess the phase and amplitude of the endogenous circadian oscillator is to track the body temperature cycle during long-term studies where behavioral activity is desynchronized from the output of the endogenous oscillator, thereby distributing masking effects of activity on the temperature cycle across a variety of temperature pulses. Typically, this assessment method is carried out prior to, and following a particular intervention in order to assess the effect of that intervention on the circadian oscillator. However, since masking effects are not in any way eliminated, each of the assessments require the collection of 4-6 weeks of continuously recorded data in a time-isolated facility. Following spectral analysis of the data, an endogenous circadian period is determined. Using this period, an average waveform is educed. Endogenous circadian phase and amplitude are determined from this educed waveform. For statistical reasons, this estimate is accurate only for days in the middle of the study, and achieves its greatest inaccuracies at the beginning and end of the study. Also, because this method is dependent upon an accurate period assessment, a misestimation of period, when iterated over the length of the study, can result a several hour misestimation of phase.

Because this method is inaccurate in initial and final phase estimation, it is unsuited to be used as the "before" and "after" assessment components of an experimental protocol designed to test the effect of a particular invention. Additionally, their length is prohibitively long for practical use.

In the following section we describe a technique which is able to characterize the output of the endogenous circadian pacemaker in a brief time. This has utility both in identifying circadian dysfunction and in developing a body of normative data on circadian function. Most importantly, in a preferred embodiment consisting of two such assessments, one immediately prior to and one following an intervention, this method provides a means of assessing the ability of a particular intervention to modify circadian phase and amplitude. In this regard, this new method and its preferred embodiments have provided a means both for development and validation of the empirical methods upon which our techniques of modifying circadian phase and amplitude are based.

The preferred embodiment of the method of accurately assessing the phase and amplitude of the deep circadian pacemaker is premised on the elimination of confounding factors which would otherwise mask the measurement of the phase. The confounding factors introduced by food ingestion, changes in posture, changes in physical activity, sleep onset and waking are eliminated according to the preferred embodiment of the present invention. Generally, the effects of these factors on the phase measurement are minimized by eliminating them, or at least distributing them evenly over the course of the phase measurement process.

2. Method for Assessment of Circadian Phase and Amplitude Resetting Capacity The preferred embodiment of the method for assessment of circadian phase and amplitude resetting capacity is based upon a comparison between a pre-intervention phase and amplitude assessment and a post-intervention phase and amplitude assessment. The pre-intervention assessment characterizes the baseline status of the circadian timing system. It also provides a phase and amplitude reference useful in the subsequent determination of the appropriate time(s) to schedule the intervention stimulus. The post-intervention assessment provides a final characterization of the circadian system so that an objective assessment of the efficacy of the intervention can be made.

FIG. 1 shows an example of the preferred embodiment of the method for assessment of circadian phase and amplitude resetting capacity. In this particular study, a human subject was studied for seven days in an environment free of time cues. The schedule of this embodiment of the assessment technique is presented in double raster format as described below (e.g., in the discussion relating to FIGS. 8 and 18). The first thirty to forty hours of the study (represented by an open bar) constitute the pre-intervention phase and amplitude assessment. Days 2-5 comprise the particular intervention stimulus under study. The final 40 hours (represented by an open bar) depicts the post-intervention assessment of phase and amplitude. It is necessary to detect and account for the free-running phase delay which occurs in the Constant Routines. Thus, a correction factor related to the free-running deep circadian pacemaker period $\tau_x$ must be considered when formulating conclusions regarding the effect of the intervening experiment.

In this example, the intervention stimulus chosen was a particular light schedule consisting of bright indoor light (large boxes) and episodes of darkness/sleep (solid bars). However, the intervention stimulus chosen may be of any nature (i.e., a pharmaceutical agent or other therapy). In this example, the duration of the intervention stimulus was approximately 3.5 days. However, the intervention stimulus may take on any duration, shorter or longer, depending upon the nature of the particular intervention.

The pre- and post-intervention assessments of phase and amplitude are advantageously embodied in a technique called the "Constant Routine". The Constant Routine involves keeping the subject at absolute bedrest in a semi-recumbent posture (i.e., lying in bed with the head of the bed (from the waist up) advantageously elevated at an approximately 45 degree angle, and the knees elevated and supported advantageously to provide approximately 90 degrees between the back of the calf and the back of the thigh). This ensures that changes in the physical posture do not influence the phase or amplitude assessment. The subject refrains from any physical activity, since physical activity might also influence or distort the phase measurement. In practice, arm and head movement, and general shifting of body weight in the semi-recumbent posture, are allowable. However, the torso should not be elevated from the bed, even for brief periods.

The subject is kept awake in ordinary room light throughout the duration of the assessment so that sleep onset or offset and changes in ambient light levels also do not affect the phase measurement. Finally, to minimize the effects of food intake which would result from a normal schedule of large meals, the subject ingests measured small amounts of food at closely spaced intervals, such as hourly. The food is advantageously chosen to emulate the daily nutritional intake of the individual during a normal day, with the subject on an isocaloric diet, with caloric intake calculated using the Wilmore nomogram, with balanced electrolyte intake of 150 milliequivalents of sodium and 100 milliequivalents of potassium per 24 hours. This effectively continuous feeding ensures that any effect of food ingestion on the phase measurement is evenly distributed throughout the duration of the phase measurement technique.

Figures 2A, 2B:
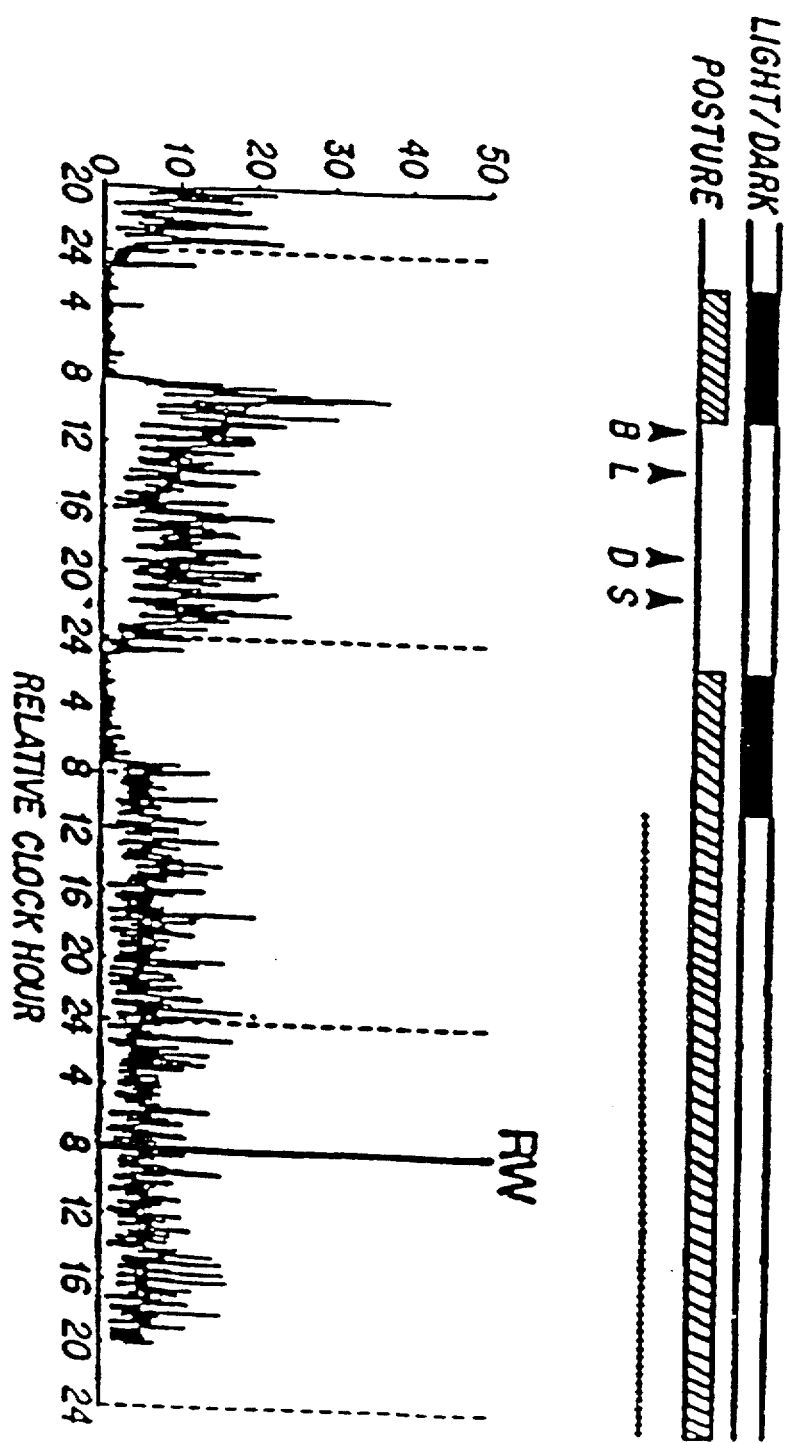

Assessment of physiologic parameters is advantageously achieved by continuous measurements of core body temperature via a thermistor inserted 10 cm. into the rectum, a skin temperature thermistor worn on the inner - aspect of the non-dominant wrist; polysomnographic recording from surface electroencephalographic (central, frontal and occipital placements), electromyographic and electrooculographic electrode placements; an intravenous placement unit in a forearm vein for multiple frequent sampling of blood (3 samples per hour) without repeated venipuncture; cognitive and behaviorial alertness and performance measures; and other techniques well known in the art. The overall Constant Routine protocol is illustrated in FIGS. 2A and 2B, and is further explained in the discussion directed to FIGS. 3, 4, and 7.

The measurements are then advantageously plotted as a function of time for statistical analysis. Advantageously, statistical analysis using harmonic regression techniques may be used to calculate the amplitude of the endogenous temperature rhythm, and to pinpoint the time of the endogenous temperature cycle minimum, which serves as a marker of circadian phase. For example, see Brown, *Sleep, Research*, Vol. 14, p. 90 (1985).

Other researchers have considered many of the confounding factors which are eliminated by the Constant Routine. However, what was missing in many such experiments was the correct bracketing of the initial estimate of the deep circadian pacemaker minimum. In the absence of a reasonable estimate of the timing of this minimum, other experimenters did not choose a duration long enough to ensure that each phase assessment exposed at least one unobscured minimum of the endogenous circadian temperature cycle, as is ensured by a 40-hour Constant Routine according to an embodiment of the present invention.

It is advantageous that the subject remain in this Constant Routine for at least one and one-half full periods of his or her endogenous circadian pacemaker. Generally, this period is approximately 25 hours. In one embodiment of the present invention, the full duration of the Constant Routine is 40 hours. A 40-hour Constant Routine allows several hours at the beginning of the Constant Routine to dissipate any transient effects of the subject's sleep episode or other activities immediately before the Constant Routine. It has been found that approximately 4-5 hours at the beginning of the Constant Routine are necessary to dissipate the effect of those activities. Using a full 40-hour Constant Routine ensures that at least one unobscured endogenous circadian pacemaker minimum is measured without any effect being imposed by the transient response to the subject's activity immediately prior to the Constant Routine.

In another embodiment of the assessment method according to the present invention, a Constant Routine of duration much shorter than 40 hours may be successfully practiced. The use of this shorter assessment method is premised on knowledge of the approximate time of the minimum of the endogenous circadian pacemaker minimum. It is desirable that 6-8 hours of core body temperature measurements both before and after the deep circadian pacemaker minimum be recorded, in order to accurately determine the minimum using, for example, mathematical techniques described by Brown, cited above. Therefore, it is conceivable that a Constant Routine of a duration as short as 16 hours can be applied. (2×6 hours surrounding the minimum +4 hours to dissipate the transient effects=16 hours.)

Since, especially in longer-duration Constant Routines, the period of imposed wakefulness may prove burdensome to many subjects, it is preferred that Constant Routines are timewise flanked by periods of darkness/sleep. These periods of darkness/sleep must be considered when assessing the effects of the bright light/darkness regimen on a particular subject, since the periods of darkness themselves have a strong effect on the phase and amplitude modification being investigated. In most experimental scenarios, a Constant Routine is entered both before and after the regimen of bright light pulses and darkness periods. The periods of darkness which flank both Constant Routines are an integral part of the stimulus regimen, and are advantageously scheduled to enhance the phase-shifting characteristics of the regimen.

Figure 3:
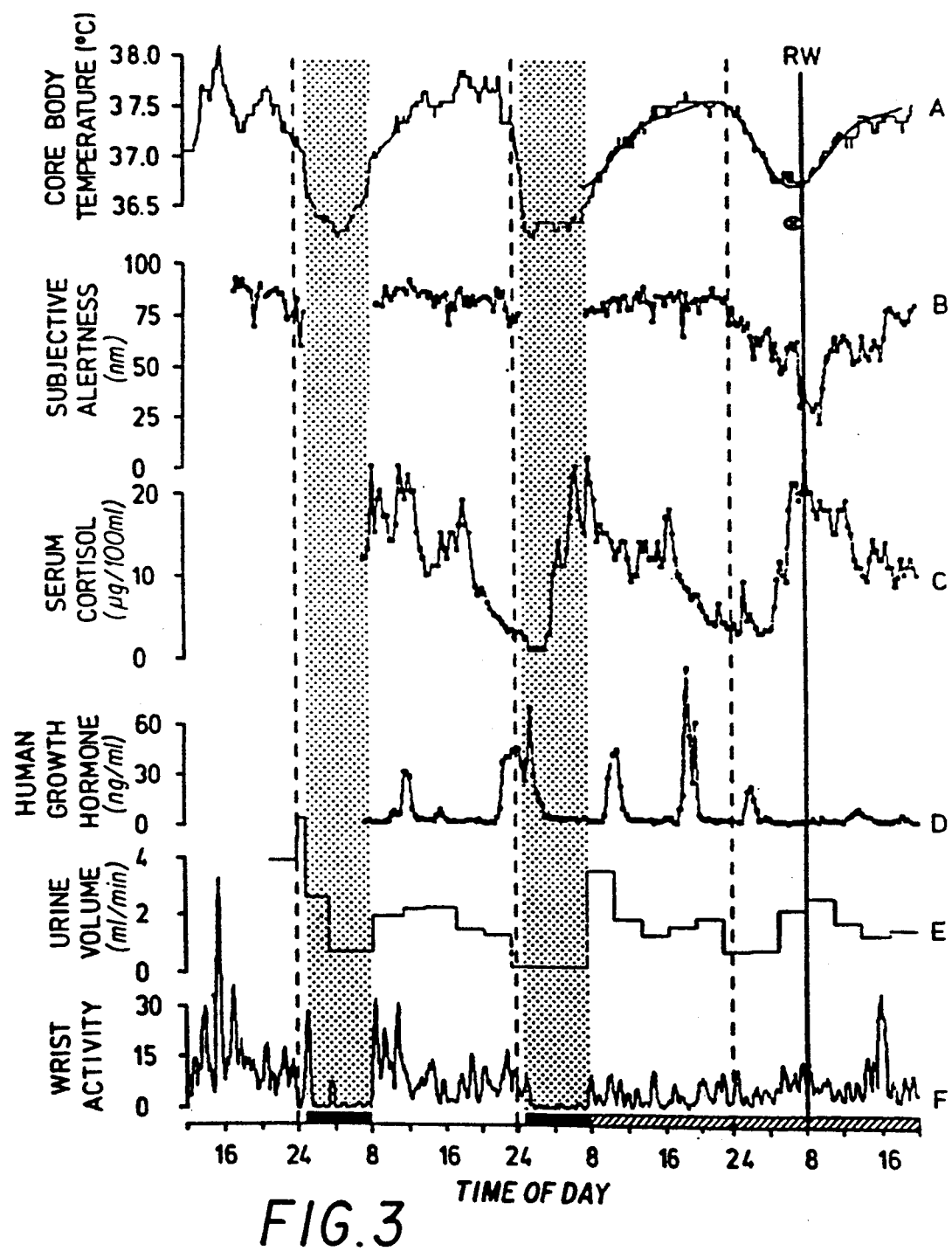
FIG. 3 shows the recording of multiple physiologic functions from a single subject (203) on an entrained baseline day and during a Constant Routine.

FIG. 3 shows the daily patterns of several physiologic and cognitive functions in a single young male subject on a normal day and during a phase and amplitude assessment procedure. A fitted dual harmonic regression model of the body temperature data during the Constant Routine is shown in Panel A, superimposed on the actual body temperature data. Time is plotted along the horizontal axis; dark bars and stippled areas indicate episodes of sleep the cross hatched bar represents the time of the Constant Routine. In comparing data collected during the Constant Routine days with that of the previous entrained day, one can see the persistent oscillation of the endogenous component of the observed rhythms, which is prominent in the case of core body temperature, subjective alertness, serum cortisol secretory pattern, and urine volume; such oscillations are no longer detectable in the activity level, and growth hormone secretion ceases under these constant conditions. By fitting the endogenous component of the temperature rhythm with a harmonic regression curve (as has been done in the upper panel of this figure), an estimate of the amplitude and fitted phase of the temperature minimum (marked by the encircled cross) of the endogenous circadian pacemaker can be made.

Figure 4:
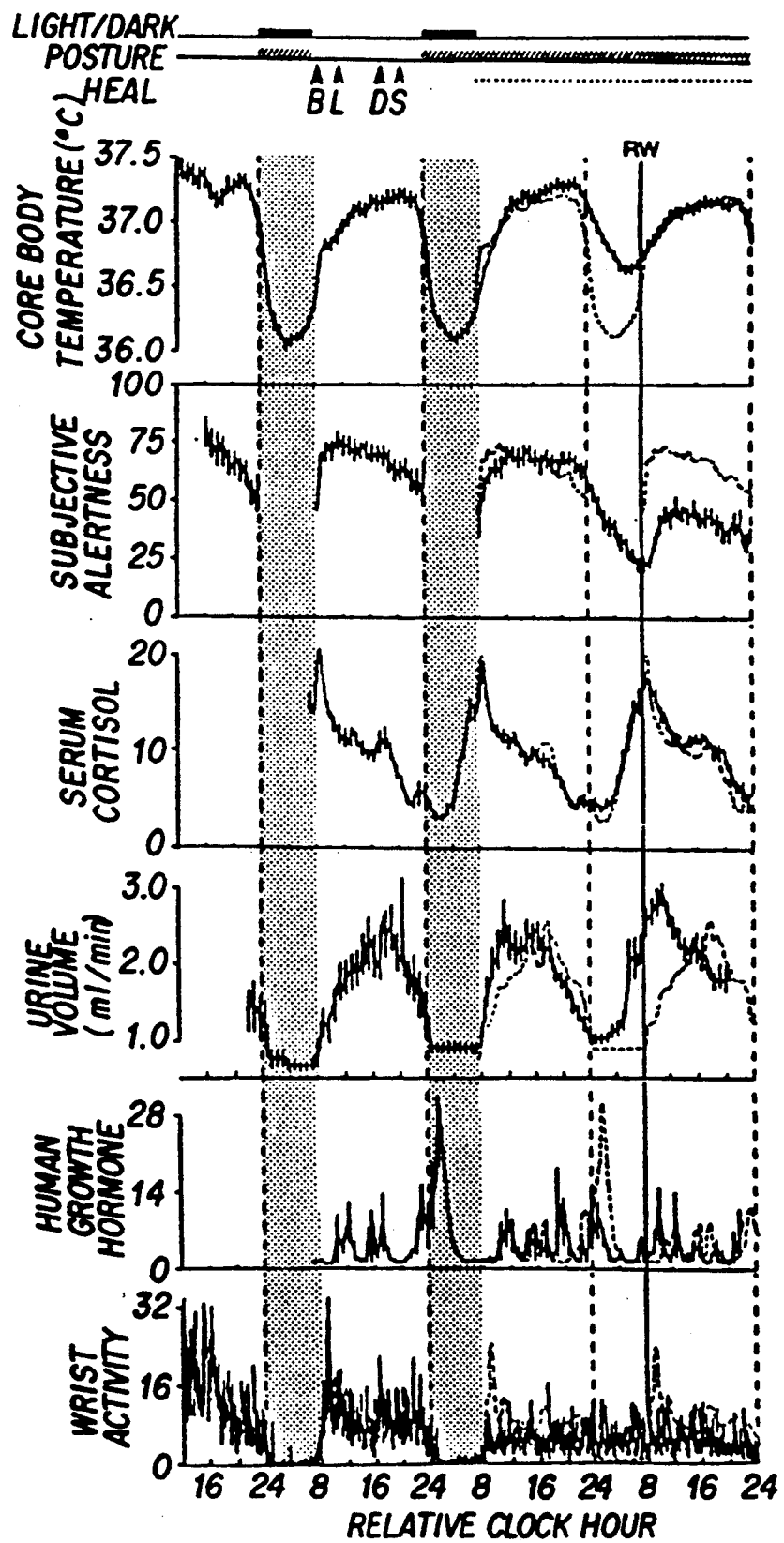
FIG. 4 shows circadian rhythms of normal young subjects during baseline laboratory monitoring and during the endogenous circadian phase assessment (Constant Routine), averaged across subjects with respect to their habitual waketime (RW), baseline data being superimposed (dashed line) on that collected during Constant Routine for comparative purposes.

FIG. 4 shows normative data collected from 29 normal young male subjects. The protocol is indicated in the top legend, with symbols as in FIGS. 2A and 2B. B, L, D, S mean breakfast, lunch, dinner, snack, respectively, before the Constant Routine was entered. Panel A—core body temperature ($N=29$); Panel B—subjective alertness ($N=27$); Panel C—serum cortisol ($N=23$); Panel D—urine volume ($N=28$); Panel E—Human Growth Hormone; and Panel F—wrist activity ($N=18$). The data are normalized with respect to the subjects' habitual reference waketime (RW), and are plotted in a manner similar to that of FIG. 3. Additionally, data from the entrained day are superimposed (dotted lines) during the Constant Routine period to facilitate comparison between the entrained (masked rhythm) and the unmasked Constant Routine waveforms. Note how the Constant Routine temperature data from the individual subject in FIG. 3 closely matches that of the normative population, allowing accurate comparison of data recorded on a single individual with that of the normative population.

Figure 5:
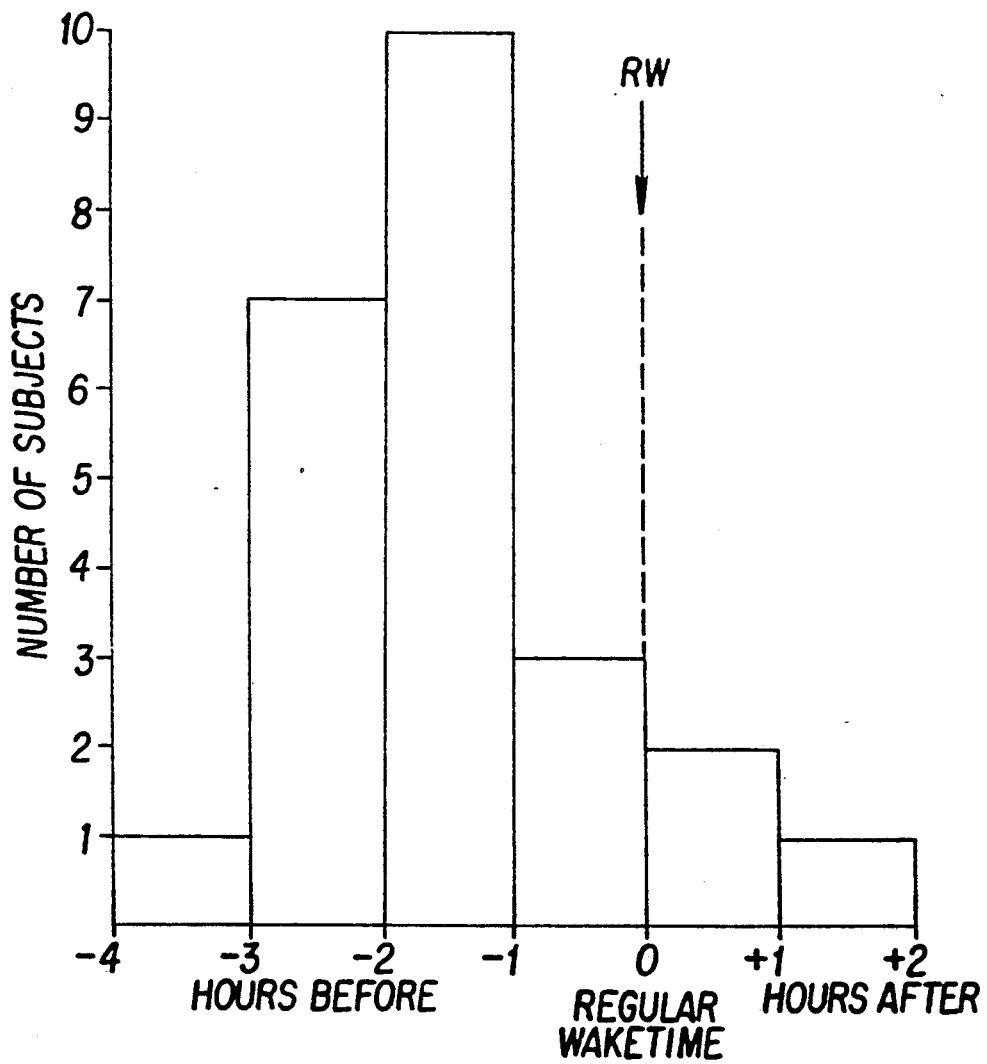
FIG. 5 is a histogram of estimated reference phase position of the deep circadian oscillator as marked by the trough of the endogenous component of the circadian temperature cycle in 24 normal young subjects 18 to 26 years old.

FIG. 5 shows a histogram of the estimated phase of the endogenous circadian temperature minimum, based on data collected from 29 normal male subjects with no history of circadian disruption (i.e., shift-work, transmeridian travel, or disturbed sleep). As can be seen, most subjects reached their endogenous temperature minimum approximately $1.5 \pm 1.0$ hours before their habitual waketime.

Figure 6A:
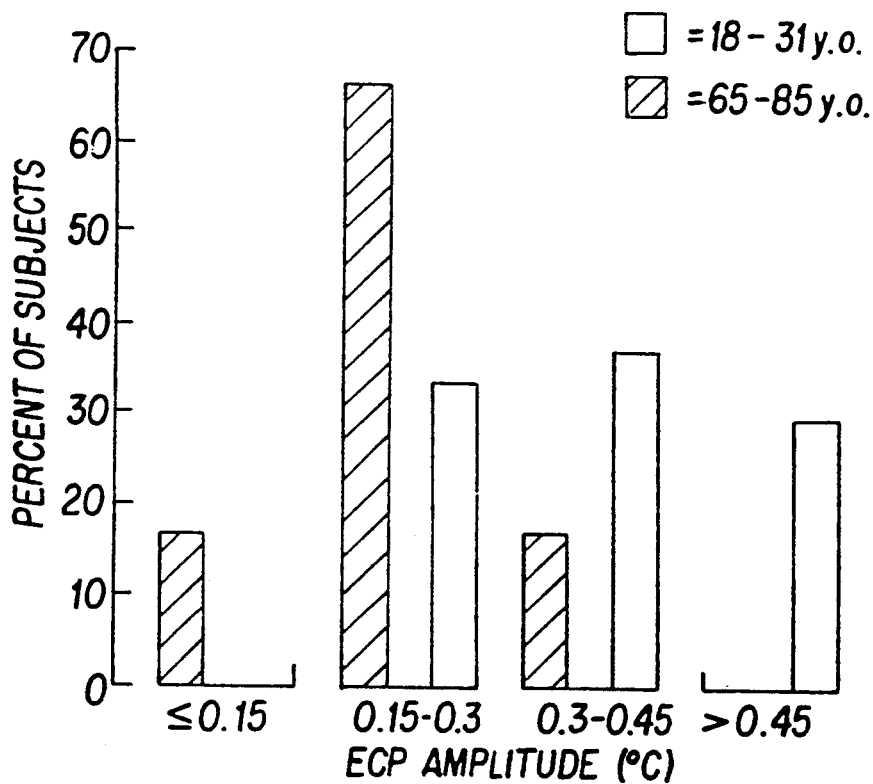
FIG. 6a is a histogram of the amplitude of the fitted temperature from young (open bars) as compared to elderly (hatched bars) subjects.
Figure 6B:
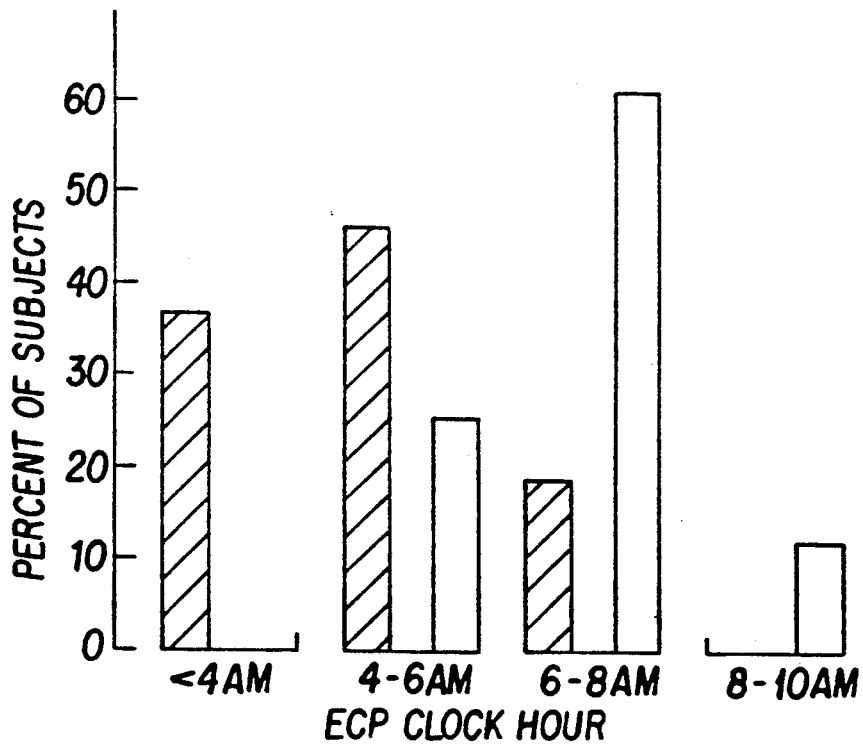
FIG. 6b is a histogram of the clock hour of the estimated circadian phase position in young as compared to elderly subjects.

Normative data for subjects of various ages is shown similarly in FIGS. 6a and 6b. In FIG. 6b, one can see that the amplitude of the temperature rhythm measured during the Constant Routine is lower in the elderly population (65-85 years of age). The second panel shows that the phase of the endogenous circadian temperature rhythm occurs earlier in the elderly than in the young normal males.

Figure 7:
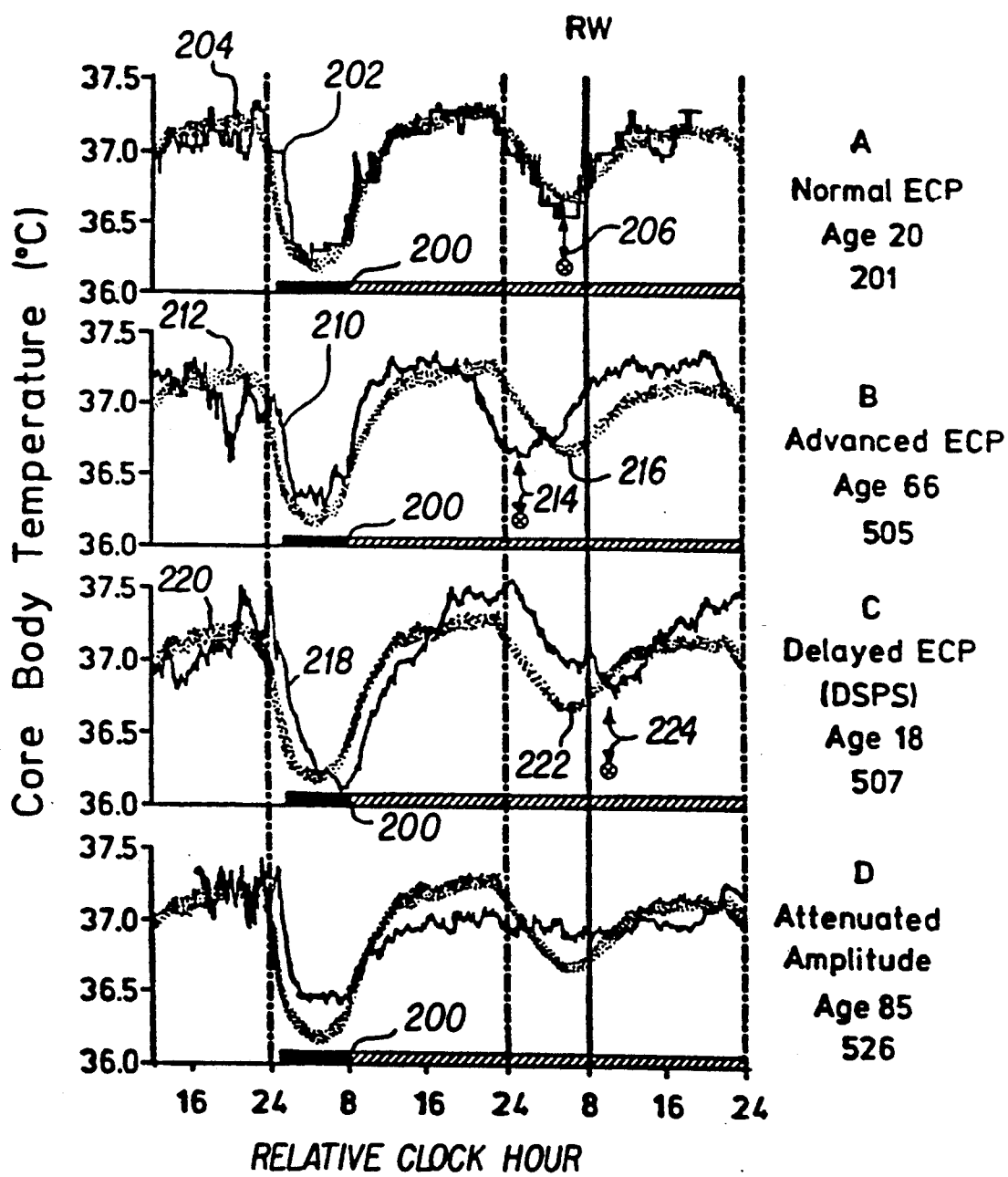
FIG. 7 illustrates the core body temperature of four individual subjects as compared with normative data, the comparison of which demonstrates the "unmasking" of the endogenous circadian pacemaker enabled by the phase assessment method of the present invention.

FIG. 7 demonstrates the unmasking effect of the Constant Routine according to a preferred embodiment of the method according to the present invention. FIG. 7 illustrates the core body temperature of four subjects as a function of time. The top panel presents the core body temperature of a normal young subject; the second panel, that of an elderly subject with advanced circadian phase; the third, that of a young adult with Delayed Sleep Phase Syndrome; and the bottom, that of an elderly subject with reduced amplitude.

For all four subjects, the Constant Routine commences at time 0800 on the first full day, as illustrated at 200. The Constant Routine continues for 40 hours until the end of the second full day. The duration of the Constant Routine is indicated on the time axes to the right of 200. Before the Constant Routine was initiated (to the left of 200), the core body temperature of each subject was monitored, starting at noon on the day before the Constant Routine.

All four panels illustrated in FIG. 7 have plotted normative data 204, 212, and 220 for comparison to various individual core body temperature plots 202, 210, and 218. The normative data plots 204, 212, and 220 are identical.

As can be seen in the pre-Constant Routine period to the left of 200, all four subjects' core body temperature followed the normative data with a high degree of phase correlation. Before the onset of the Constant Routine, then, it would have been impossible to accurately determine the endogenous circadian pacemaker amplitude or phase because of the activity-induced core body temperature response.

Before engaging in the Constant Routine, all four subjects appeared to be normal, based on observation of core body temperature. In fact, however, only the subject illustrated in the top panel was normal.

The top panel of FIG. 7 shows a 20-year-old male whose measured core body temperature coincided with the trough of the normative data at 206. His endogenous circadian pacemaker minimum, as indicated by the core body temperature minimum, was timed optimally for a regular waking time (RW) of 8:00 a.m. This subject reported no abnormalities or difficulties in his sleeping habits.

The second panel shows the core body temperature of a 66-year old woman suffering from extreme phase-advancement, characteristic of many elderly subjects. Her measured deep circadian pacemaker trough 214 was in fact 4.5 standard deviations earlier than the trough 216 of the young subjects contributing to the normative data plot 212. In contrast, the core body temperature trough of the normal young subject in the upper panel is synchronized to the measured deep circadian pacemaker minimum at 206.

The third panel illustrates the core body temperature from a young patient suffering from Delayed Sleep Phase Insomnia. This subject had reported great difficulty in awakening in the morning and remaining alert. This difficulty is explained by the fact that his internal physiology did not even begin to "awaken" until about noon. The third panel of FIG. 7 illustrates his core body temperature trough at 224 as being approximately 4 hours past his regular wake time, 8:00 a.m. This trough 224 is also significantly delayed from the normative data trough at 222.

The bottom panel illustrates the reduced amplitude characteristic of many elderly subjects. The significance of this reduced amplitude is discussed below.

The core body temperature troughs indicated at 206, 214, and 224 were unmasked by the Constant Routine. These troughs indicate the tendency of the deep circadian pacemaker to establish its own period and phase which are demonstrable in the absence of activity-induced body temperature changes. A value of the Constant Routine in eliminating physiologic responses to environmental and behavioral stimuli lies in diagnosing such phase advance or phase delay disorders. Once diagnosed, these disorders may be treated according to a method of phase-shifting according to the present invention, described below.

The preferred embodiment of the assessment method is far less time-consuming than the assessment methods described previously which require temporal isolation for a time period on the order of 30 days. The method of assessment according to the present invention thus allows clinical observation in cases where extremely accurate individual phase and amplitude measurements must be made. The present method also allows the gathering of extremely accurate normative data which can later be used in the phase adjustment of large classes of people who are similarly situated with respective classes of subjects whose circadian cycles' characteristic phase and amplitude have already been assessed using the Constant Routine.

3. Empirical Foundations for the Inventive Techniques to Modify Circadian Phase and Amplitude Aschoff and Wever in Germany and Siffre in France discovered that numerous daily rhythms in man also persist in the absence of environmental and social time cues. However, under these conditions of temporal isolation, the "free-running" period of these rhythms no longer remained exactly 24 hours (FIG. 8).

Figure 8:
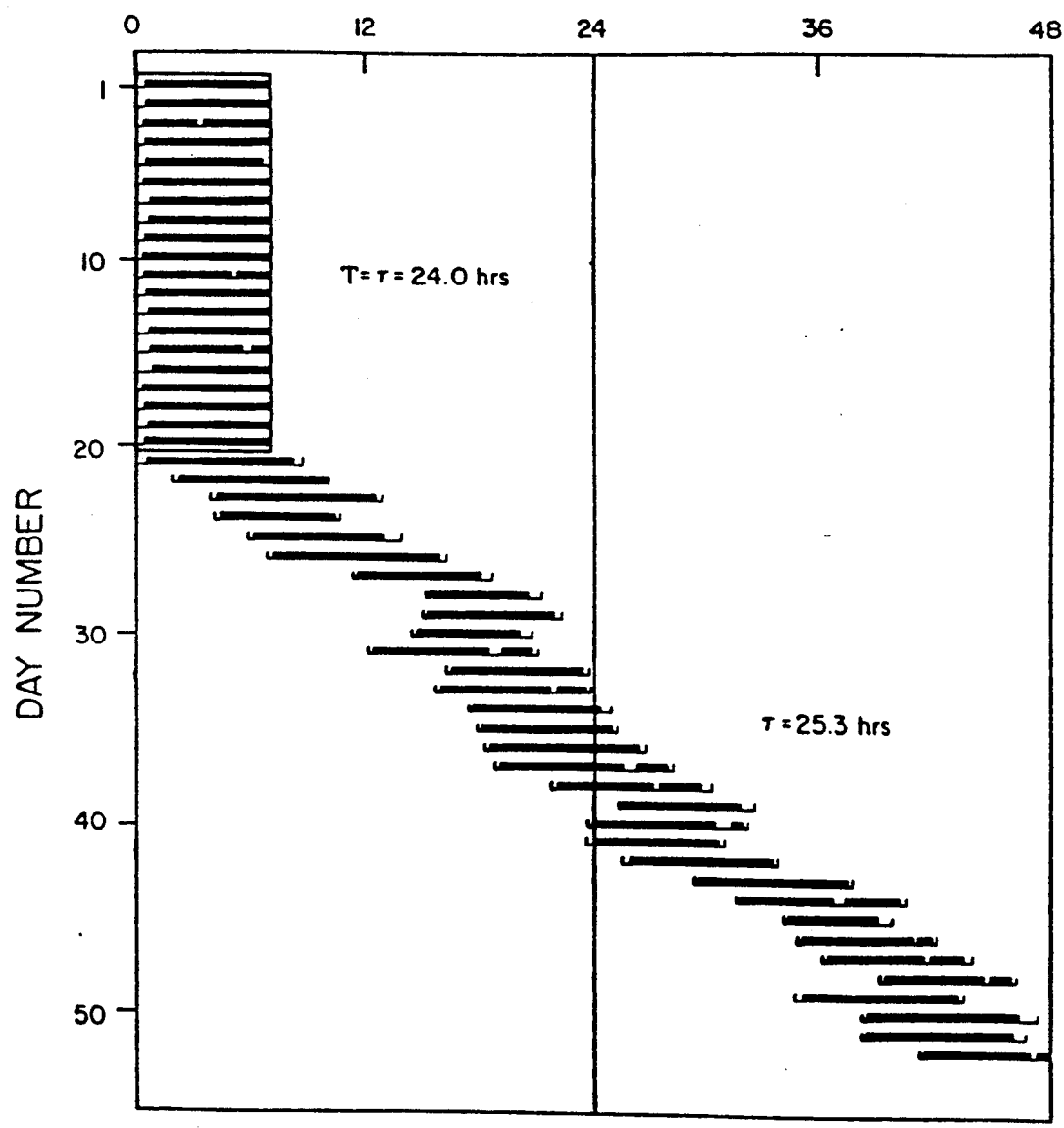
FIG. 8 shows entrained and free-running sleep-wake pattern of a normal 22-year old male subject living in an environment without knowledge of time.
Figure 9:
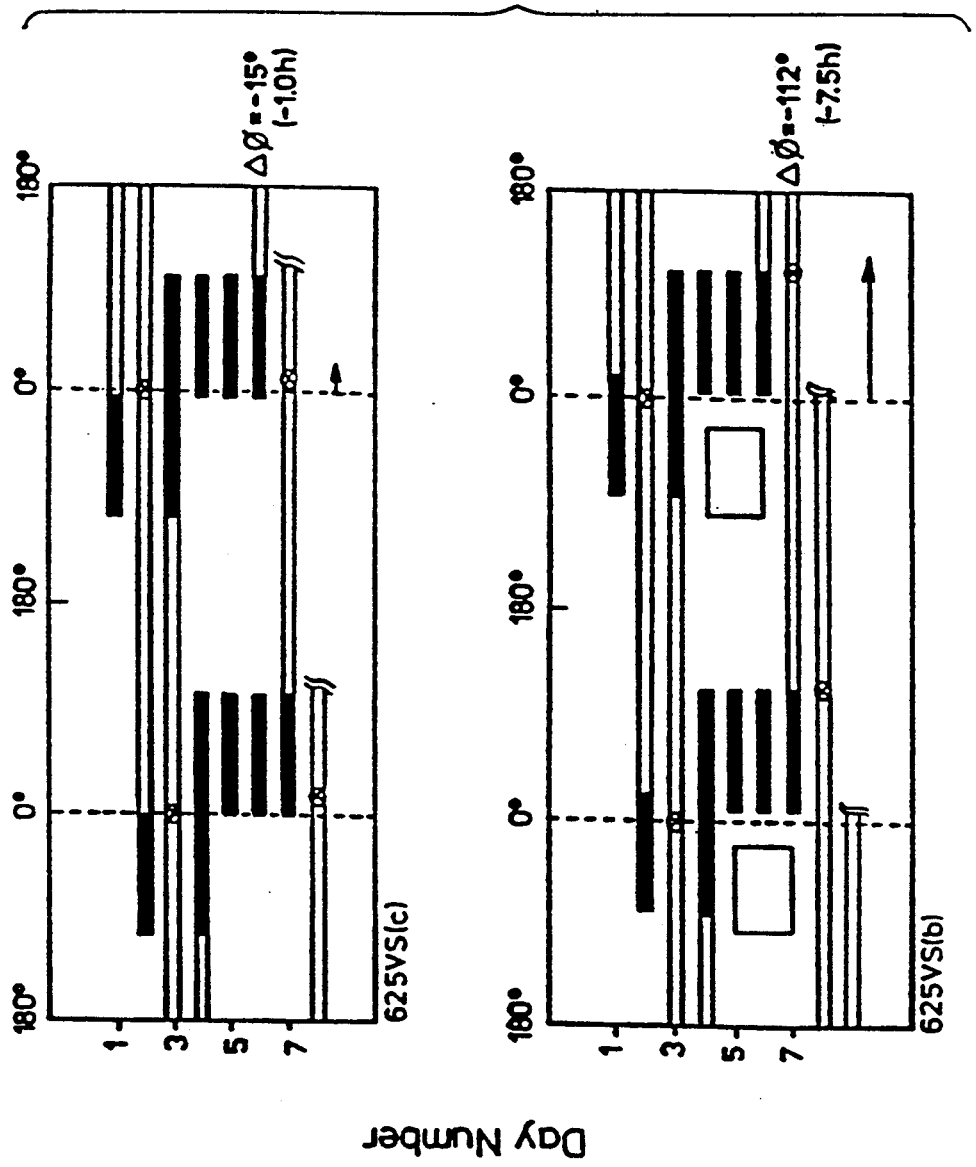
FIG. 9a demonstrates the insignificant ECP phase delay (1h) to be expected by mere manipulation of the darkness episode.
FIG. 9b demonstrates the significance of the delay (7.5h) achieved using a bright light pulse regimen.

Referring to FIG. 8, a raster diagram of the sleep episodes of a subject in temporal isolation is illustrated. The horizontal time axis is referenced to the subject's habitual bed time (hour 0), as recorded in a home sleep-wake diary during the prior week. Successive days are plotted beneath each other. Scheduled sleep/dark intervals (outlined by a black box) were from hours 0 to 7 on days 1-20. Thin horizontal lines indicate time span awake in bed; time asleep (as determined polysomnographic recording) is indicated by heavy black horizontal bars. Thin vertical lines indicate self-selected bed times and times of rising.

Generally, raster diagrams have a series of time axes, each of which traverses continuously from left to right. Each horizontal time axis is labelled with a "Day n" number which indicates the 24-hour period which is presented in the left-most 24 hours of that time axis. Information about days immediately succeeding "Day n" may be illustrated to the right of the leftmost 24-hour period in the "Day n" axis. (In some raster displays—unlike FIG. 8—information from the Day n axis may actually be repeated, but left-shifted by 24 hours, on the Day n+1 axis.) Raster diagrams thus provide a convenient means by which temporal activities and conditions may be analyzed both in a serial fashion (horizontally), and in a parallel fashion (vertically) for comparison.

Referring again to the particular raster diagram in FIG. 8, during Days 1-20 of the experiment, the subject was forced to keep a regular schedule synchronized to the 24-hour geophysical day, as indicated at 102. The subject's circadian cycle was thus "entrained" to a 24-hour period.

After the 21st day, the subject was allowed to choose when to sleep, awaken, eat, etc., naturally, his schedule being governed only by his internal circadian pacemakers. Consistent with previous experimental results in humans and diurnal animals, from Days 21-53 the subject's activity-rest cycle and core body temperature cycle both assumed their "free running" (but mutually synchronized) periods of greater than the previously entrained period of 24 hours. The assumption of a period longer than 24 hours is indicated in FIG. 8 as a gradual but steady phase delay in both the bed rest episodes. The free-running period was determined by linear regression through midsleep times to be 25.3 hours.

The first 20 days of the experiment depicted in FIG. 8 are indicative of the "normal" days experienced by the majority of humans. Their internal circadian cycle periods of greater than 24 hours are overridden, or reset, by some zeitgeber. It was thought that only zeitgebers such as social contact or imposed activity could reset the circadian cycle to the 24-hour geophysical day. As will be seen below, humans are in fact no exception to the rule in the animal kingdom that light, in and of itself, is a strong zeitgeber.

Ordinary sunlight, then, apparently resets both the deep circadian pacemaker and the activity-rest pacemaker on a daily basis to a 24-hour cycle. This resetting allows humans to function in activities which are necessarily tied to the 24-hour geophysical day. If the circadian cycles of humans were not reset on a daily basis, the free-running cycle of greater than 24 hours would cause disruption of individuals' performance not only with respect to the geophysical day, but also with respect to other individuals' free-running but mutually desynchronized circadian cycles.

Concomitant with the discovery of non-twenty-four hour free-running circadian rhythms in man came the assumption that man, like all other eukaryotic organisms studied, must have a mechanism of entrainment receptive to exogenous time cues (Zeitgeber) which would allow synchronization to the twenty-four hour geophysical day. The effect of an entraining agent, such as a light pulse in otherwise constant darkness, on circadian rhythms has been studied extensively in a variety of species, ranging from single-celled eukaryotes to primates. It is therefore possible to describe the effect of a single light pulse in otherwise constant darkness by means of a phase response curve which indicates that under such conditions the phase of administration of the light pulse alone determines the magnitude and direction of the phase shift elicited.

Although it was generally accepted that the light-dark cycle was the most potent resetting stimulus in almost all eukaryotic organisms, much debate arose as to the nature of the principal resetting stimulus in man. Based on a series of temporal isolation studies, Aschoff and Wever concluded that a 24-hour light-dark cycle was too weak an entraining stimulus to mediate the approximately one hour phase resetting necessary for synchronization to the 24-hour geophysical day. A critical review of the experimental protocol revealed that the subjects of Aschoff and Wever were in fact self-selecting much of the lighting in the experimental suite. It is therefore not surprising that a free-running pattern emerged. Subsequent studies under more rigorous control have revealed that a light-dark cycle alone is capable of entraining the human circadian timing system to a twenty-four hour day. (See C. A. Czeisler et al., "Entrainment of Human Circadian Rhythms by Light-Dark Cycles: A Reassessment," *Photochemistry and Photobiology*, Vol. 34, pp. 239-249 (1981)). It was not known, however, whether this entrainment was the result of a direct action of light on the central hypothalamic pacemaker or whether it was simply due to the light-dark cycle's indirect influence on the behavioral choice of bedtime and wake-time.

Unfortunately, physiologists had been unable to demonstrate an unequivocal direct effect of bright light on human circadian rhythms, primarily because of a lack of experimental techniques to directly assess circadian phase in real time. The development of the aforementioned means of assessment of phase and amplitude resetting capacity has now yielded a better understanding of the interaction between the human biological clock and periodic environmental stimuli than had been afforded by the animal studies carried out under the rather simplistic and clinically irrelevant condition of total darkness.

As will be described below, applications of bright light may be artificially imposed to achieve effects other than mere resetting to the geophysical day. It will be seen that bright light can be used to achieve dramatically rapid shifting of circadian phase. Very significantly, the application of bright light can have a direct influence on the deep circadian pacemaker, independent of the timing of activity-related factors.

Based on application of the above assessment technique, the present invention is partially based on the determined circadian effects of numerous different illumination schedules, all consisting of components of bright light, ordinary indoor light, and absolute darkness. The invention is partially based on newly discovered general properties of the human circadian pacemaker's response to light-dark cycles. These can be summarized as follows:

A. Bright light is required to shift rapidly the phase of the circadian pacemaker. That is to say that shifting the timing of the sleep-wake schedule alone is inadequate in effecting large, rapid phase shifts.

Figure 9A:
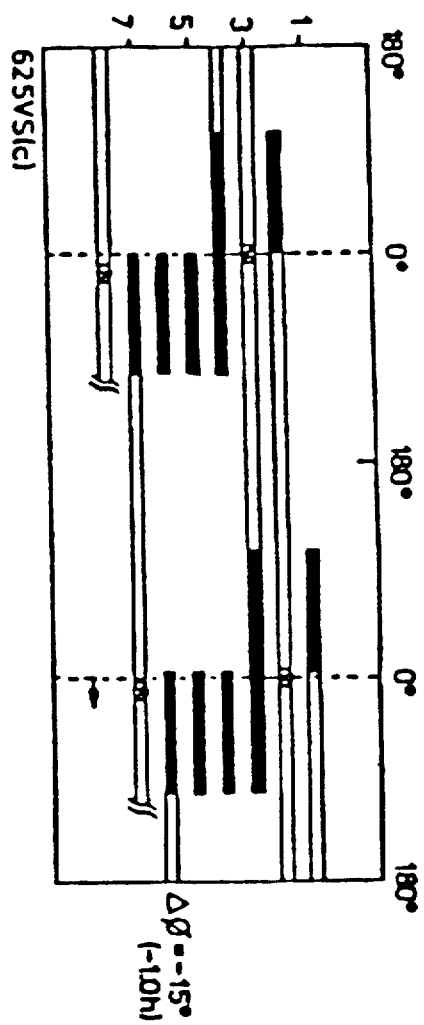
Figure 9B:
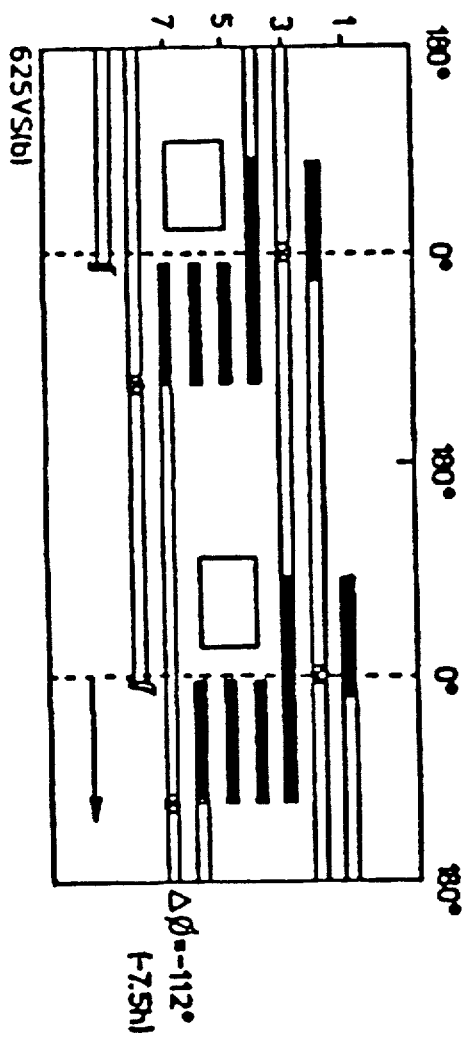

It was discovered that bright light is necessary to rapidly achieve phase modification. Dimmer light, such as ordinary indoor lighting on the order of 100-300 lux, was ineffective to cause phase modification which could be clearly attributable to the application of such light. However, when bright light, on the order of 7,000-12,000 lux (optimally averaging about 9,500 lux or greater in the preferred embodiment) is applied daily, phase shifts on the order of 9-11 hours in a 2-3 day period are commonly observed. (For intuitive reference, 9,500 lux is equivalent to the outdoor illumination near the time of dawn or dusk. Bright sunlight at noon presents an ambient light intensity of approximately 100,000 lux.) As can be seen in FIG. 9a displacement of darkness/sleep alone 6 hours later in time—as will often be required of shift workers or transmeridian travelers—does not result in an appreciable shift of circadian phase position. However, exposure to a bright light stimulus of appropriate intensity at an appropriate phase concurrent with the same displacements of darkness/sleep (FIG. 9b) results in a rapid and large (7.5 h) shift of circadian phase position. Although the circadian timing system would eventually adapt to a shift in the timing of the darkness/sleep schedule, use of the bright indoor lights in conjunction with the shift accelerates the rate of adjustment by 2-5 fold.

B. Bright light can reset rapidly the phase of the human circadian pacemaker independent of the timing of the sleep-wake cycle.

Figure 10:
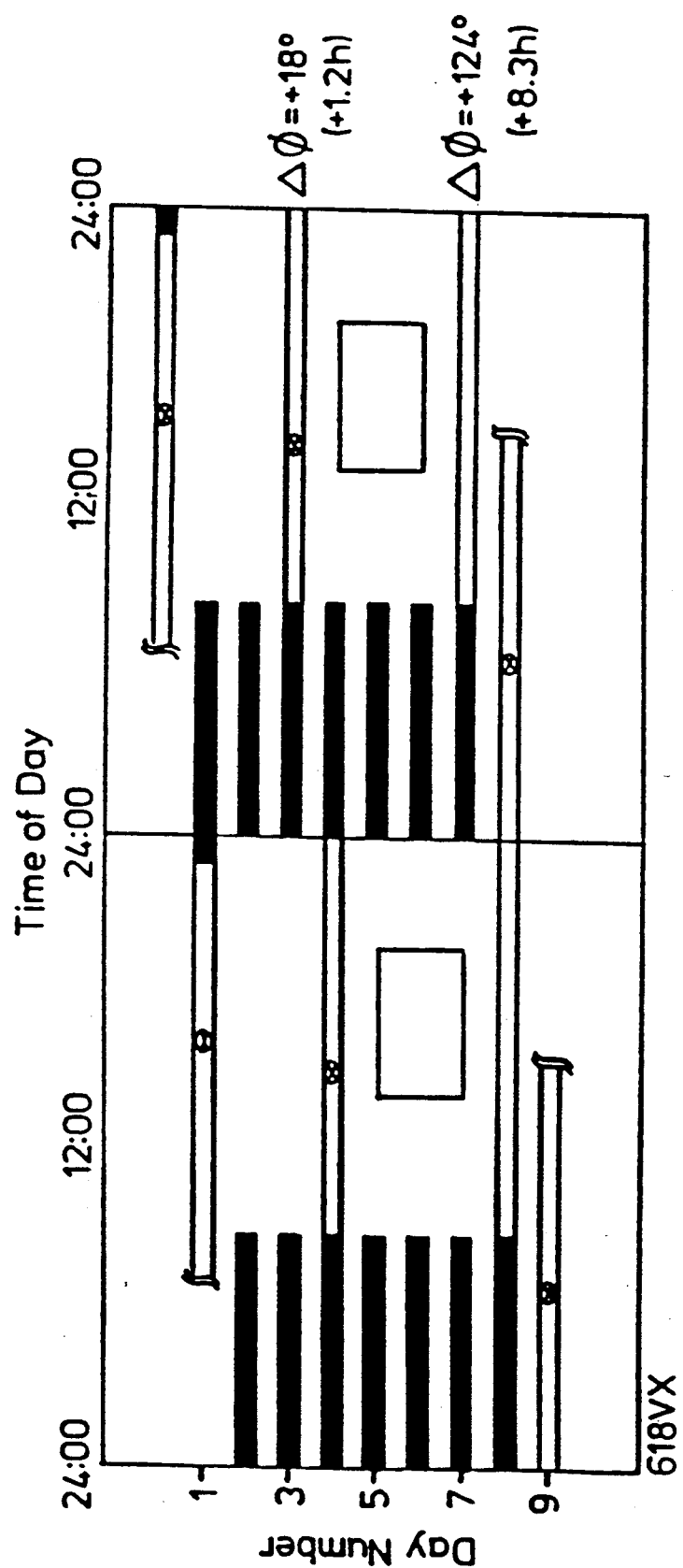
FIG. 10 shows the rapid acceleration of ECP phase adjustment caused by a bright light pulse regimen.

As shown in FIG. 10, during the first endogenous circadian phase (ECP) assessment, the subject's ECP temperature minimum (as indicated by the encircled X) was misaligned from the timing of his sleep-wake cycle, occurring 8-9 hours later than normal at 4:10 p.m. The subject's scheduled sleep/darkness episode was held essentially constant, and the subject's ECP temperature minimum remained essentially unchanged. Then, independent of the timing of the scheduled darkness/sleep episode, a bright light stimulus was introduced (large open boxes) which rapidly reset the circadian pacemaker to a normal phase position, with the ECP temperature minimum occurring 2.25 hours before the subject's waketime of 9:00 a.m.

For any given light-dark/sleep-wake schedule, it has also been discovered that the magnitude of the phase shift is critically dependent on the timing of onset of the bright light pulse with respect to the pre-existing circadian cycle. Not only the magnitude, but also the direction (advance or delay) of the phase shift can be drastically affected by this pulse onset phase. A time of particular sensitivity to bright light has been found to be in a time frame approximately two-three hours before and after the endogenous circadian pacemaker minimum. Small changes in the phase of application of light pulses can make the difference between subsequently advancing, or delaying, the circadian cycle by several hours. This observed result accentuates the necessity for an accurate method of assessment of the existing circadian phase.

C. For any given light-dark/sleep-wake schedule, the magnitude of the phase shift which can be achieved in response to bright light depends on the phase of bright light administration with respect to the phase of the circadian pacemaker (as marked, for example, by the endogenous component of the body temperature cycle).

Figure 11:
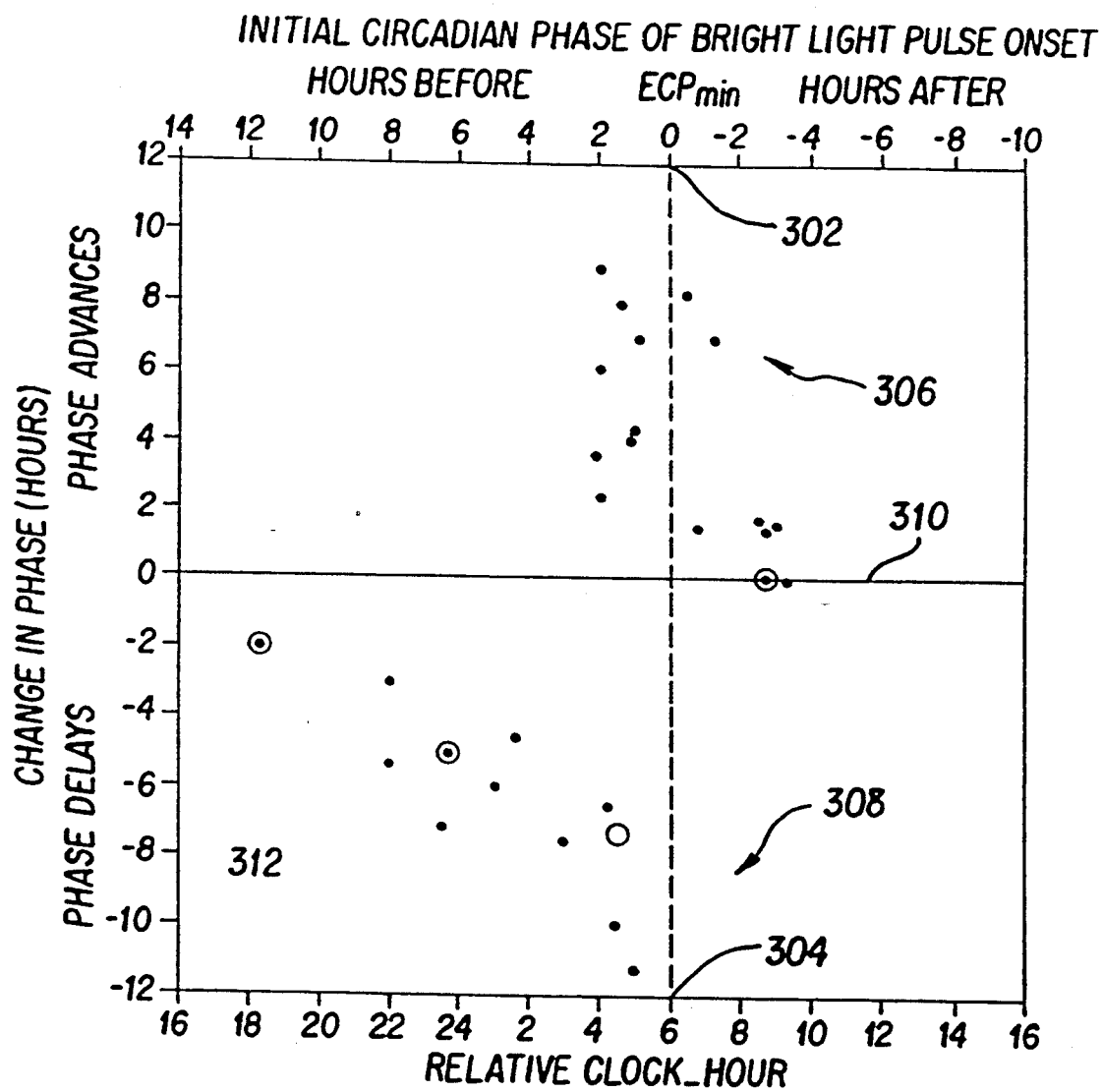
FIG. 11 shows an empirical phase response curve to 2-7 exposures of bright light (7,000-12,000 lux) in humans, with the response plotted as a function of bright light pulse onset.

FIG. 11 presents the raw data from our experiments using the technique for evaluating circadian phase capacity measuring the amount of phase shift achieved in response to bright light stimuli delivered at a range of circadian phase positions with respect to the ECP temperature minimum.

Figure 12:
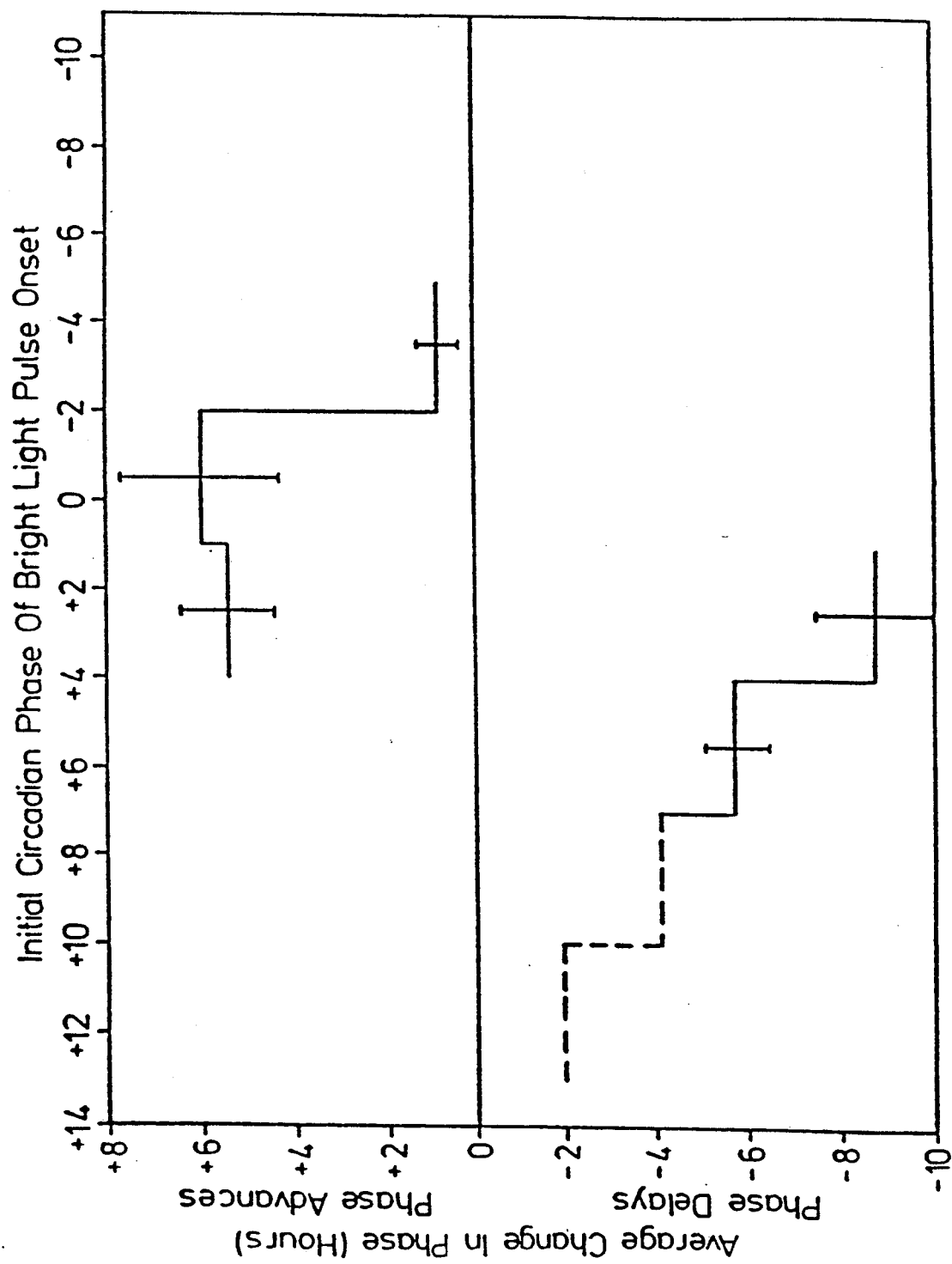
FIG. 12 shows averaged empirical phase response curve to light.

FIG. 12 presents an average plot of the same data as plotted in FIG. 11. However, data points in the advance and delay zones have been binned and averaged across intervals of three hours' duration. Vertical bars represent the standard error of the mean. In those bins which contained less than four values, a dashed line has been used to approximate the mean. Standard errors were not calculated for these bins.

The shape of this response curve to light suggests that the phase marker we have chosen—the ECP temperature minimum and its correlates—does indeed reflect the phase position of the human circadian pacemaker since the response curve generated using this phase reference marker shares the expected properties of phase delays in the early part of the subjective night, phase advances in the late subjective night and a zone of relative insensitivity during the subjective day.

Since the phase response curve is a circadian pacemaker property, the phase reference marker which we have chosen (i.e., the endogenous component of the core body temperature rhythm) must maintain a relatively fixed phase relationship to the output of the circadian pacemaker. (See S. Daan and C. S. Pittendrigh, "A Functional Analysis of Circadian Pacemakers in Nocturnal Rodents: II. The Variability of Phase Response Curves," *J. Comp. Physiol.*, Vol. 106, pp. 253–266 (1976).)

The magnitude of the shifts and shape of the response curve (see A. T. Winfree, The *Geometry of Biological Time*, Springer-Verlag, (New York, Heidelberg, Berlin), 1980, pp. 36–38, p. 53), unexpectedly indicates that our three pulse protocol has generated what is called a strong "Type 0" phase response curve, usually observed only in plants and insects in response to light and seldom observed in mammals or other higher organisms (see D. S. Saunders, *An Introduction to Biological Rhythms*, Blackie (Glasgow and London), 1977, pp. 40–64). The existence of Type 0 resetting means that a full description of the state of the oscillator requires amplitude as well as phase of the oscillator. Furthermore, for Type 0 resetting, there is at least one point on the resetting curve for which the amplitude of the oscillation passes through zero during the resetting process, and that for a correct phasing of the stimulus and adjustment of its strength, zero amplitude can be achieved. The phase response curves to light found in most mammals, including primates (see T. M. Hoban and F. M. Sulzman, "Light Effects on Circadian Timing System of a Diurnal Primate, the Squirrel Monkey," *Am. J. Physiol.*, Vol. 249, pp. R274–R280 (1985)) are of a weak "Type 1" resetting pattern, which are generally of low amplitude (maximum phase shifts of only one to three hours) and do not have a sharp "break point" between the advance and delay portions of the curve. Type 1 resetting can be described in terms of phase only.

Therefore, this empirical finding of Type 0 resetting in humans in response to scheduled episodes of bright light and darkness would not have been predicted a priori by someone skilled in the art and knowledge of the subject. This information makes possible many of the useful applications described herein.

Referring to FIG. 11, the effect of the timing of application of bright light pulses on the circadian phase shift is illustrated. FIG. 11 comprises two time axes superimposed on one another. The top time axis is determined by the placement of the endogenous circadian pacemaker minimum at 302, labeled $ECP_{min}$ (Endogenous Circadian Phase minimum). The bottom time axis presents a standard 24-hour day in a way which associates the endogenous circadian phase minimum with a time of 6:00 a.m., as indicated at 304. The plotted points are experimental results of repeated use of the Method of Assessment of Circadian Phase and Amplitude Resetting Capacity, described above. The key to FIG. 11 is $0 = \times 2$; ● $= \times 3$; ⊙ $= \times 7$. Data points above the zero phase change line 310 phase advances. Data points below the zero phase change line 310 indicate phase delays, measured after the application of bright lights. The independent variable in each of these experiments was the time when, in the existing endogenous pacemaker cycle, the bright light pulse began.

The distribution of data points in FIG. 11 illustrates that there is an interval of particular sensitivity around the minimum of the deep circadian pacemaker. Points generally indicated at 306 show a phase advance, while points generally indicated at 308 show a phase delay. The relatively small phase separation of the pulse onsets for different experiments, as well as the strength of the resultant phase changes for pulse onsets timed closely together, accentuate the necessity for careful timing of the light pulses. Application of bright light pulses several hours before or after the endogenous circadian phase minimum result in more modest phase delays as indicated at 312.

Results such as those found in FIG. 11 are consistent with the Phase Response Curve (PRC), described above and shown to have general validity during the "subjective night" of lower animals. However, earlier PRC's did not take into account the importance of the timing of episodes of darkness and ordinary room light.

Figure 14:
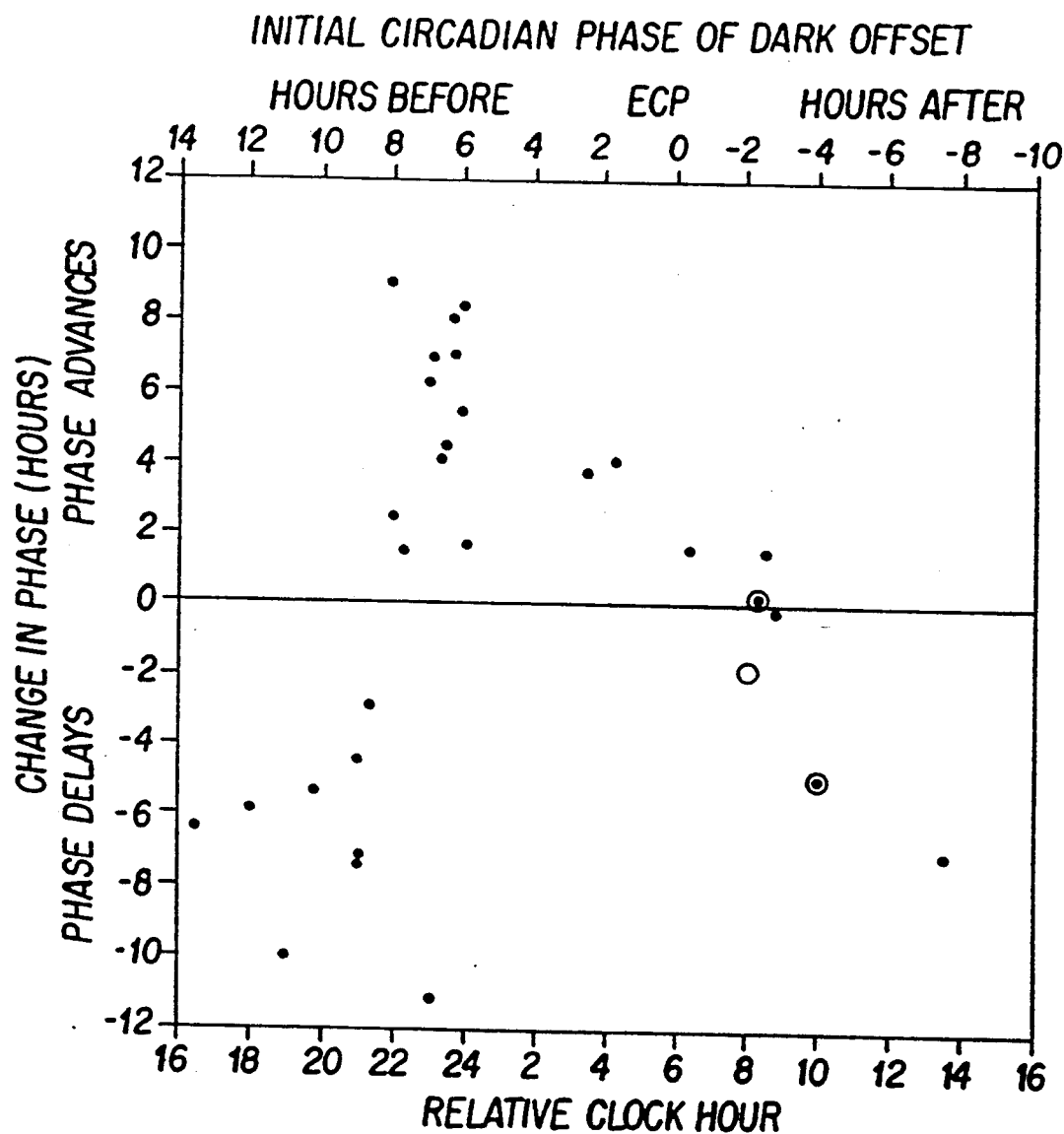
FIG. 14 shows an empirical phase response curve to 2-7 exposures of bright light, with the phase response plotted as a function of darkness/sleep offset.

Unfortunately, a 2-dimensional PRC cannot take into consideration the importance of the scheduling of episodes of darkness (rest) in relation to the bright light pulse applications. FIG. 14 demonstrates how proper alteration of episodes of darkness allows more control to be exercised over the change in circadian phase, particularly in the zone of greatest sensitivity (i.e., breakpoint).

The bright light pulse applications according to the present invention may be facilitated through use of many different types of commercially available lamps, for example, ordinary fluorescent lights. Because the photopic and scotopic sensitivity functions cover most regions of the visible spectrum, it is likely that most "white" light and many monochromatic bands of light could be used effectively, provided luminous flux is sufficiently great in the range of the pertinent visual sensitivity function.

In many of our studies we have used Vitalite fluorescent sources (Duro Test Corp.) which have a spectral output designed to mimic sunlight, including UV light. We have also, however, used commercially available cool white fluorescent sources in other studies, and have seen no difference in effect at the same illuminance level. Fluorescent lamps were chosen over incandescent lamps for primarily economic reasons. As stated previously, there is no reason to suppose superiority or inferiority of a particular lamp at the appropriate light intensity as measured in lux or foot-candles, which are weighted to reflect the human visual sensitivity function.

Bright light may be administered by any means which provides adequate optical illumination, and it is recommended that user comfort and practicality be considered. Nevertheless, to achieve the lighting intensity desirable for practice according to the preferred embodiment of the present invention 7,000–12,000 lux, averaging about 9,500 lux, essentially the entire ceiling (or wall, etc.) of a room must be covered with fluorescent light fixtures. Other devices, such as portable goggles or helmets or other appliances may also be employed. Such devices will be explained in greater detail below. All that is necessary is that the retina be exposed to bright light for the properly chosen pulse duration. Of course, the subject need not be staring directly at lights. It is sufficient that he be effectively surrounded by light of the appropriate intensity for the appropriate duration.

D. Although application of bright light pulses can alone cause rapid phase modifications, the timing of episodes of darkness (rest) with respect to the bright light pulses also has a profound effect. Together, a schedule of bright light pulses and periods of darkness maximizes the efficiency of the phase modification.

Figure 13:
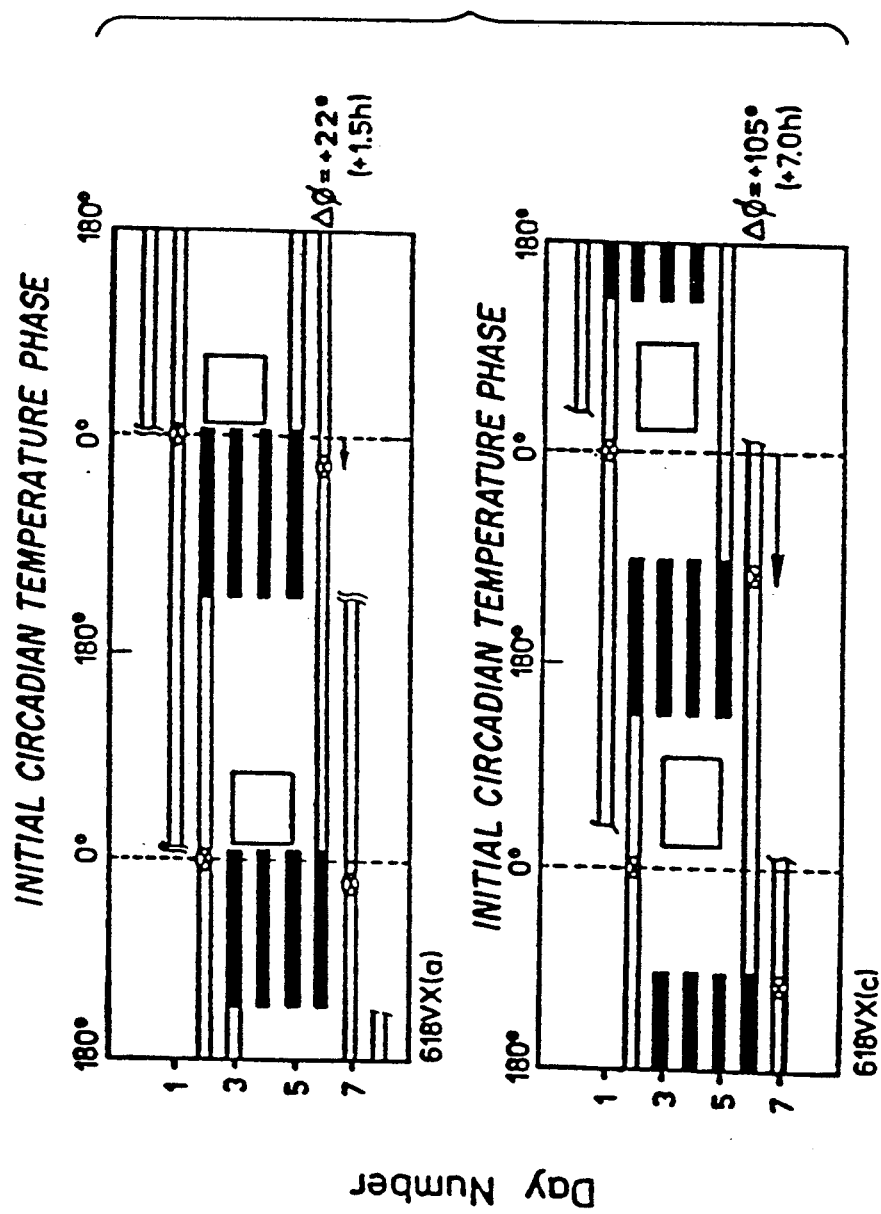
FIG. 13a shows the effect of the timing of a darkness episode on the magnitude ECP phase shift caused by a given bright light pulse regimen.
FIG. 13b shows the effect of the timing of different darkness episode on the magnitude ECP phase shift caused by a given bright light pulse regimen.

One of the most unexpected empirical results of the studies conducted to form a basis of this invention is the importance of darkness/sleep in determining the phase shift elicited in response to a bright light stimulus at a given phase. The upper panel of FIG. 13 illustrates a subject with an ECP temperature minimum occurring at its normal position, just prior to the end of the daily darkness/sleep episode. Exposure to bright light each morning for three consecutive days resulted in a small phase advance of the ECP temperature minimum, such that it now occurred 2.0 hours before the subject's habitual waketime.

However, as shown in FIG. 13b, daily exposure to the light at the same relative phase position concurrent with a phase advance of the daily episode of darkness/sleep resulted in a marked phase advance of the circadian phase position during the same interval. This demonstrates the importance of the timing of darkness/sleep in determining the magnitude of the phase shift induced by light. Thus, scheduling the timing of the daily episode of darkness/sleep is a critical element in the successful implementation of this invention because of its governing effect over the magnitude of the response to the stimulus at certain phases of administration. This governing effect of the scheduling of darkness/sleep on the magnitude of the response to bright light is opposite to that which previously would have been predicted by one skilled in the art, since the results of plant and animal studies would have led to the conclusion that shifting sleep or darkness would probably not be necessary to shift circadian phase position in response to a change in the lighting regimen (see A. J. Lewy et al., "Immediate and Delayed Effects of Bright Light on Human Melatonin Production: Shifting 'Dawn' and 'Dusk' Shifts the Dim Light Melatonin Onset (DLMO)," *Annals NY Acad. Sci.*, pp. 253–259, (1985)).

FIG. 14 illustrates the overall importance of the timing of darkness/sleep in determining the phase shift response to bright light, regardless of the circadian phase of bright light administration. The response elicited is plotted with respect to the interval between the end of the darkness/sleep episode and the ECP temperature minimum. The key to FIG. 14 is $O = \times 2$; $\bullet = \times 3$; $\odot = \times 7$. FIG. 11 and FIG. 14, when considered together, provide an adequate description of human phase resetting capacity to schedules comprised of bright light, ordinary indoor room illumination, and darkness, where corresponding data points in the two figures can be identified on the basis of the phase shifts achieved. The schedule preferred to induce any phase shift desired can be derived from those two figures, as will be illustrated in the section below entitled: "Phase and Amplitude Modification Using Empirical Foundations."

E. The timing of absolute darkness/sleep can determine the direction of the phase response to bright light in man, even when the bright light stimuli are administered at the same circadian phase.

Figure 15:
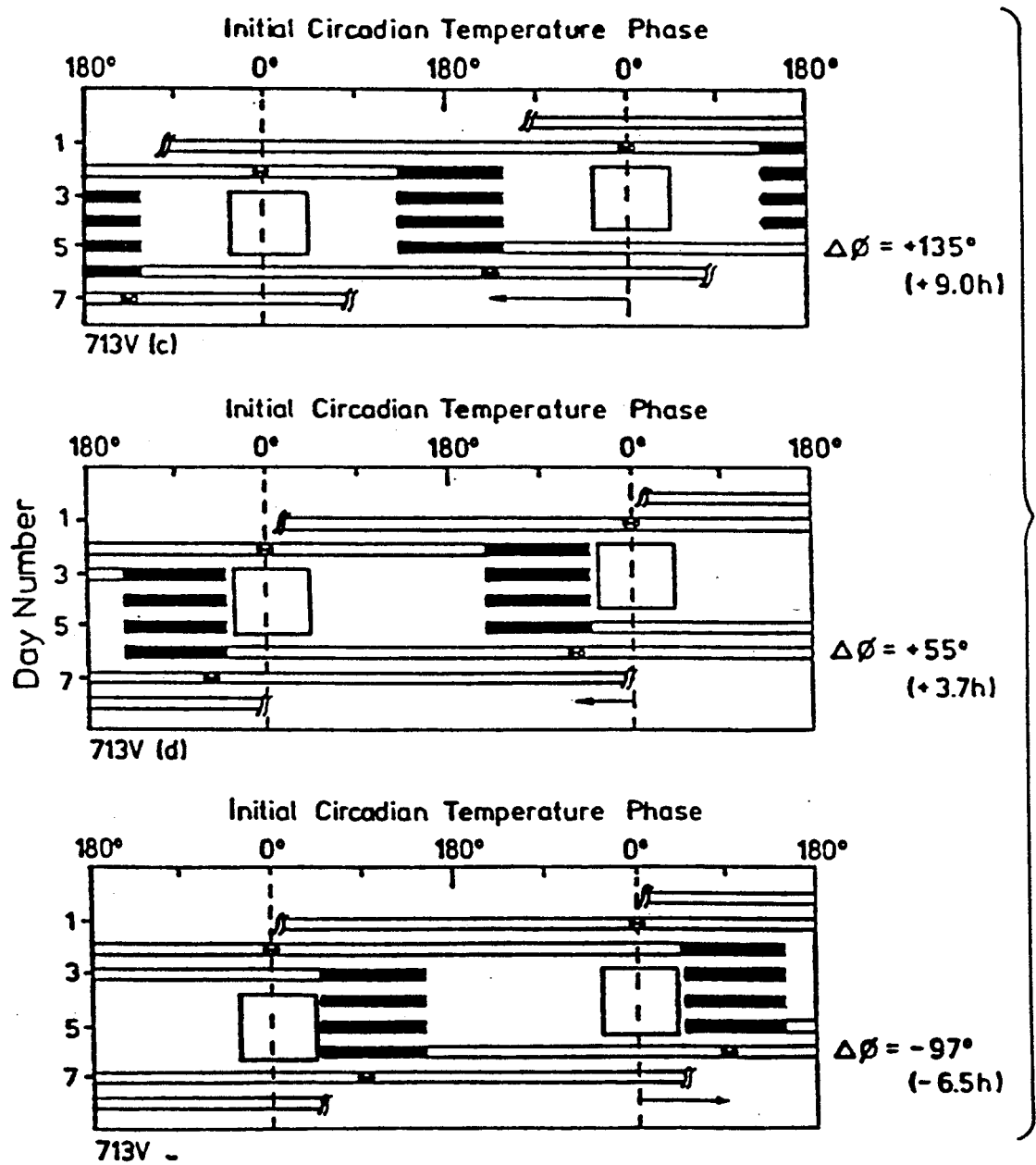
FIG. 15 demonstrates how the magnitude and direction of phase shift in response to bright light depends on the scheduling of exposure to ordinary room light versus darkness/sleep.

The upper two panels of FIG. 15 illustrate in a different subject the same type of magnitude governing effect of darkness/sleep position on the circadian phase resetting response to bright light as that illustrated in FIG. 13 and described in Section D above.

However, the third panel of FIG. 15 illustrates that if the timing of the darkness/sleep episode is scheduled to immediately follow rather than precede the daily bright light exposures, a substantial phase delay shift is elicited rather than the phase advances generated by the prior light exposures given at the same relative phase position. This effect of the scheduling of darkness/sleep vs. the scheduling of ordinary indoor room lighting is in sharp contrast to the predictions which had been made earlier by those skilled in the art (see S. Daan and A. J. Lewy, "Scheduled Exposure to Daylight: A Potential Strategy to Reduce 'Jet Lag' Following Transmeridian Flight," *Psychopharmacol. Bulletin,* Vol. 20, pp. 566–568, 1984), since it had been hypothesized by Lewy and others that the physiologic response of the circadian timing system to light only occurred when the light intensity exceeded the "threshold" intensity (about 2,500 lux) required to suppress the secretion of the hormone melatonin by the pineal gland. According to such earlier hypotheses, exposure to subthreshold levels of light intensity—whether total darkness or the 100–300 lux intensity of ordinary indoor room light—were both ineffective as compared to brighter light exceeding the 2,500 lux required to suppress melatonin production.

F. Not only the phase, but also the amplitude, of the deep circadian pacemaker is affected by the application of bright light pulses.

By reducing the amplitude with a first pulse or sequence of pulses, the effect of any subsequent pulses in phase shifting is enhanced. In the extreme case, when the amplitude is reduced to zero, a subsequent pulse immediately resets the deep circadian pacemaker to a pre-defined phase. In the development of the methods described herein we have discovered that the amplitude of the endogenous temperature rhythm, measured by the Constant Routine method, serves as a useful marker of the amplitude of the output of the endogenous circadian pacemaker.

One of our elderly subjects, shown in Panel D of FIG. 7, had a core body temperature recording during a 40-hour endogenous circadian phase (ECP) assessment which revealed an absence of any detectable circadian variation. Likewise, cortisol secretion revealed no evidence of rhythmicity.

Figure 16:
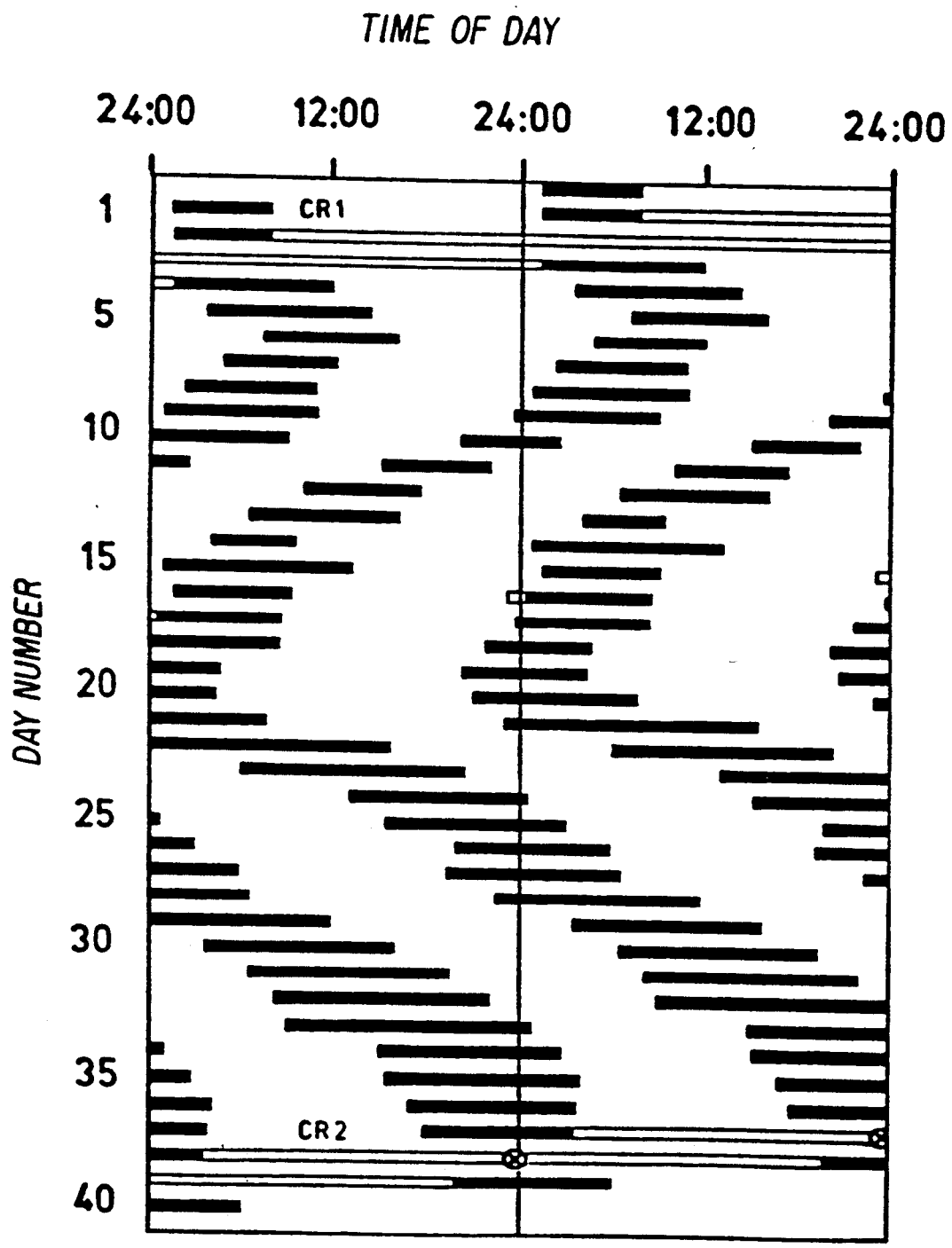
FIG. 16 shows the free-running activity-rest cycle of the elderly subject with reduced ECP amplitude whose Constant Routine core body temperature graph was presented in the bottom panel of FIG. 7.
Figure 17:
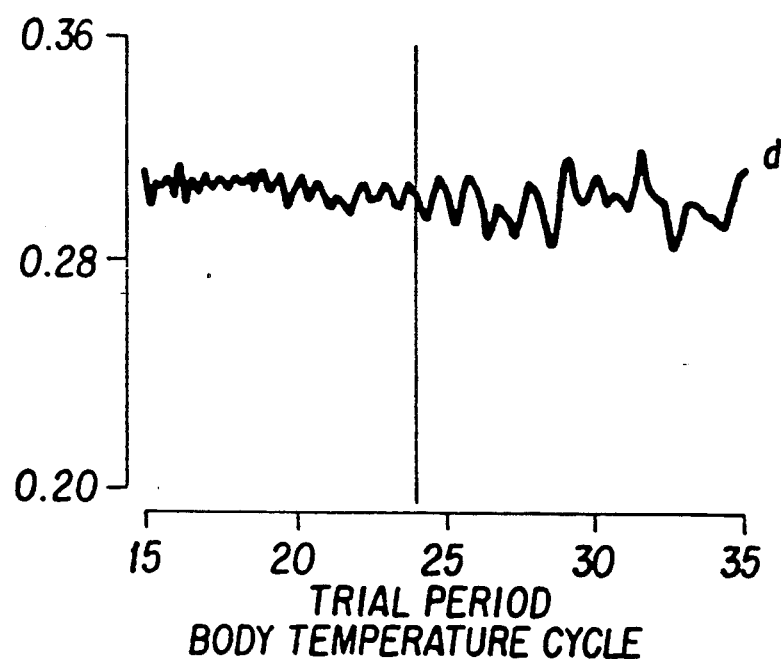
FIG. 17 shows the absence of prominent peaks in the frequency spectrum of the core body temperature of the elderly subject whose free-running activity-rest cycle was shown in FIG. 16.

In order to determine whether the lack of circadian variation in that subject's Constant Routine temperature recording reflected a reduced output of the circadian pacemaker, we conducted a follow-up recording for six weeks in a time-isolated environment, which confirmed the original finding and revealed a distinctive pattern in which the subject free-ran with an activity-rest cycle period which was alternatively shorter or longer than 24 hours (about 22 and 27 hours, respectively) (FIG. 16). Analysis of the clustering of bedrest episodes suggested the possibility of a weak output of the endogenous circadian oscillator at a period of 23.7 hours, which was further supported by the presence of a low amplitude temperature oscillation during his final constant routine, although bedrest episode durations were not consistently related to the phase of that cycle and non-parametric spectral analysis of temperature did not show a prominent peak at that or any other period (FIG. 17).

The very abnormal free-running activity-rest cycle pattern of this subject, who had a markedly reduced temperature cycle amplitude during his screening ECP evaluation, suggests that in his case the endogenous circadian oscillator had a substantial reduction in output as compared to the average subject. Otherwise, his unprecedented activity-rest cycle periods during desynchrony of first 22, and then 27, hours (activity-rest cycle periods which have not been seen in healthy young subjects, (see R. Wever, *The Circadian System of Man*, Springer-Verlag, New York, (1979)), would have been captured into synchrony by the presumably near-24-hour output of the endogenous circadian oscillator. Thus, the body temperature cycle amplitude during the ECP protocol was an accurate assessment of the amplitude of the output of the circadian pacemaker.

The confirmation of our hypothesis that the core body temperature pattern reflected the output of the endogenous circadian pacemaker has led us to conclude that interventions which change the amplitude of the endogenous component of the temperature cycle may well be altering the output of the circadian pacemaker. The phase and amplitude resetting assessment technique which we developed thereby allows us to assess the effects of a particular intervention on the amplitude, as well as phase, of the circadian pacemaker.

We have learned several general principles in the development of this method for amplitude modification. First, certain lighting regimens can reduce the amplitude of the endogenous circadian pacemaker, and in certain experiments have reduced the amplitude to a level indistinguishable from zero. Such reduction in circadian amplitude is associated with a decrease in the range of a variety of circadian controlled variables, and is especially useful in averting the decrements in physical and cognitive performance associated with the trough of the circadian temperature cycle. Also, such reduction in amplitude may facilitate the rapid shifting of circadian phase by means of manipulation of lighting schedules; and as noted above, it has been reported by Reinberg that persons with lower amplitudes are better suited to the demands of shift-work. Likewise, certain lighting regimens can increase the amplitude of the endogenous circadian pacemaker, which should facilitate both greater daytime alertness and deeper sleep at night.

Data on which the present invention is partially based therefore refute the notion that the effect of light on the circadian system is binary (i.e., dependent on light intensity exceeding a certain threshold, such as 2,500 lux), as has been suggested. The traditional "phase response curve", derived principally from brief light pulse experiments conducted on organisms living in otherwise constant darkness, is only a partial description of human phase resetting responsiveness to light-dark cycles.

The present invention uses a more useful description of circadian phase resetting by light in human. This description requires a phased summation of graded responses. That is, the response of the circadian system to a given light-dark schedule depends on the cumulative effect of all the light intensity transitions within that schedule, and that the range of intensity changes which exert an important effect are not limited to those changes which exceed a certain threshold (e.g., 2,500 lux) but encompass a graded range of light intensity transitions occurring from zero light intensity (i.e., darkness) to over 100,000 lux (e.g., the light intensity of the midday sun).

These findings are verified by several clinical intervention studies and demonstrate the practical use of the above principles in the treatment of actual jet-lag and sleep disorders. The utility of the above principles in the treatment of age-related changes in circadian function, and in the facilitation of temporal adjustment typically required by shift-workers, are also demonstrated.

4. Phase and Amplitude Modification Method Using Empirical Foundations

The modification method according to the present invention is premised on the observations that bright light has a direct effect on the endogenous circadian pacemaker, and that the effect of the bright light is significantly enhanced by proper scheduling of dark (rest) episodes. Further, proper application of light pulses and darkness episodes control the amplitude of the endogenous circadian pacemaker even to the point of reducing the amplitude to zero, so that a subsequent light pulse may instantaneously reset the endogenous circadian pacemaker to a desired phase.

Preferred embodiments of the method for shifting circadian phase based on application of light pulses, and on timing of episodes of darkness (rest) will first be described. Then, application of these methods to particular work schedules, traveling schedules, and circadian phase-related disorders will be presented. Finally, the methods of modifying the amplitude of the deep circadian pacemaker will be explained.

Although the empirically derived procedures for modifying phase and amplitude have been found experimentally to be optimal, for a particular individual in a given circumstance one of the empirically derived regimens may be inconvenient. A computer-based model has therefore been developed which allows the formulation of a variety of alternative schedules with alternative dosages, timing and duration of light exposure which will effect the same result. The theoretical foundations for the computer model are described in section 5 below, and the methods to modify phase and amplitude using that model are further described in Section 6 below.

The remainder of the current section (section 4) will therefore address the detailed description of those procedures to modify circadian phase and amplitude which may be derived directly from empirical data which is currently available.

a. Delaying Circadian Phase Using Experimentally Derived Data

Delaying circadian phase is desirable for westward jet travelers, shiftworkers who must rotate to a later shift (i.e., clockwise rotation), and patients with an undesirably advanced sleep phase (i.e., Advanced Sleep Phase Syndrome, typically, but not exclusively, found in the elderly).

Phase delays of 2-11.5 hours have been achieved in 2-3 days' time by appropriately structuring these days' lighting schedules with particular attention to the timing of bright light and darkness.

In order to best design the lighting schedule, one must have knowledge of the initial circadian phase of the person to be treated. This is best achieved by the previously described embodiment known as the Constant Routine. However, it would be acceptable in most cases to infer such phase based on comparisons made to the body of normative phase data such as is contained within this disclosure (FIGS. 3, 4, 5, and 6a, and 6b) or in the literature in general.

By subtracting the initial phase from the desired phase, the magnitude and direction of the required phase shift is determined. Then, by interpolation of FIG. 11, the optimum time to begin the administration of a bright light pulse is determined. This bright light pulse is approximately five hours in duration and has a dosage of approximately 7,000-12,000 lux in a preferred embodiment. Light of half intensity may precede and follow this five-hour pulse for approximately 15 minutes.

By interpolation of FIG. 14, the optimum timing of the dark (sleep) pulse is determined. The dark pulse lasts from approximately six to nine hours in a preferred embodiment. The retina of the eye should be appropriately shielded from substantially all light. This can be accomplished most practically by having the individual remain in a dark room, for example, while in bed sleeping. In the preferred embodiment of the technique, all artificial indoor light sources within the room (e.g., electric lamps or other light sources, gas or flame lamps, televisions, etc.) would be switched off and all sources of natural or artificial outdoor light (e.g., sunlight or street lights illuminating the room through window openings, skylights, or other modes of entry should be shielded from the room, using blackout curtains, opaque shades or other appropriate shielding devices. If the individual is unable to remain in such a dark room during the scheduled dark episode, goggles which effectively absorb 90-95 percent of visible light (such as welder's goggles) may be worn or the individual may wear contact lenses with a similar light absorbing property.

At times not specified above, the person being treated should be exposed to light of normal indoor light intensity (ca. 100-500 lux).

This lighting schedule is repeated for three days in a preferred embodiment. Upon completion of this regimen, the desired phase shift will have been achieved. A second Constant Routine can then be carried out if it is necessary to evaluate the phase or amplitude resetting capacity of the individual on that regimen.

Figure 18:
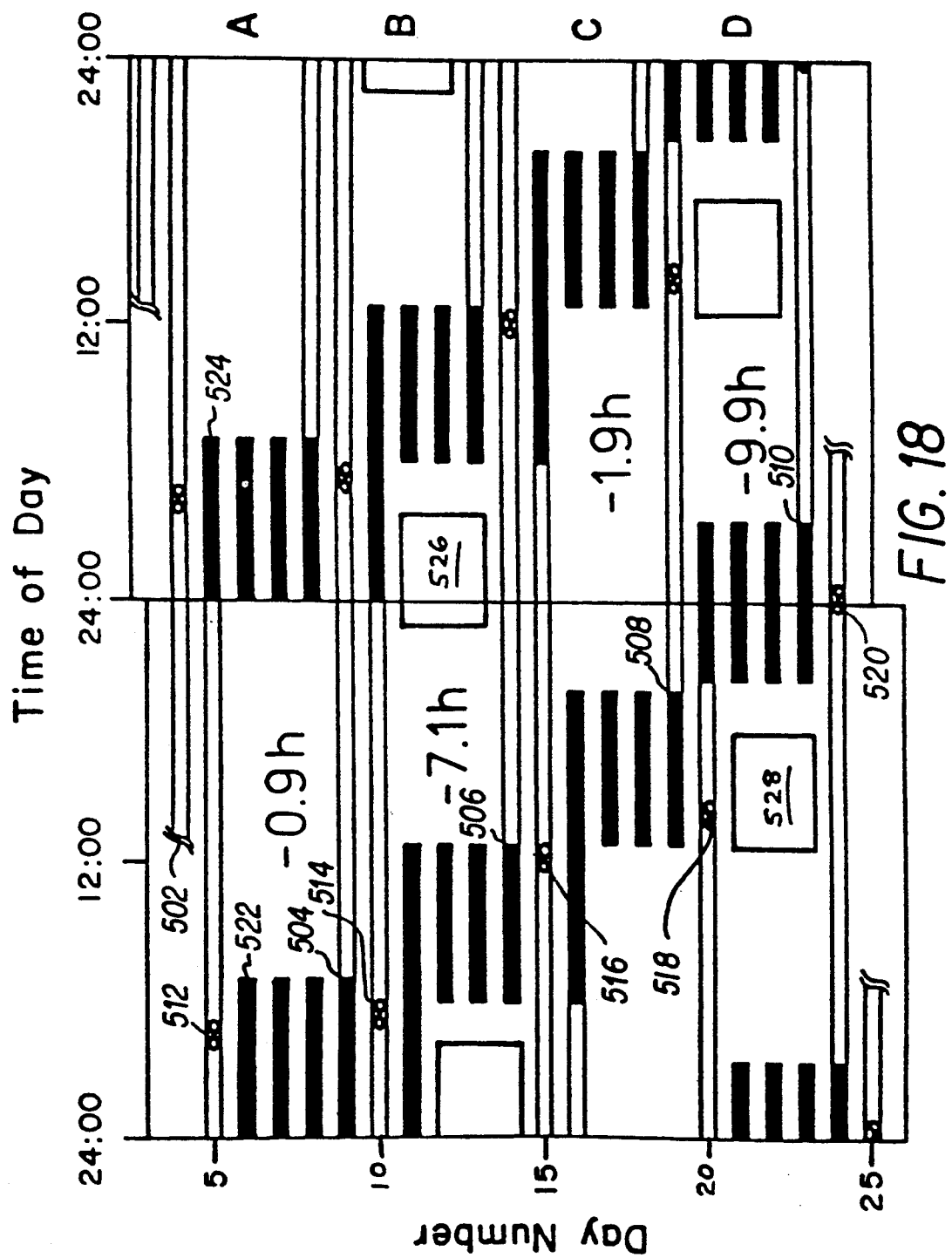
FIG. 18 is a raster diagram indicating how the application of bright light accelerates the circadian phase-shifting much faster than manipulation of the activity-rest cycle.

FIG. 18 is a raster diagram which indicates how application of bright light accelerates the phase delay shifting of the circadian pacemaker trough much faster than mere manipulation of the activity-rest cycle. FIG. 18 is a raster diagram in which the information on a horizontal time axis, for example, Day 5, contains information about both Days 5 and 6. Similarly, the time axis for Day 6 contains information about Days 6 and 7. Thus, the points indicated at 522 and 524 (FIG. 18) are in fact the same experimental point. The hollow bars in FIG. 18 indicate periods of wakefulness, and the solid bars indicate periods of enforced bed rest.

The subject was placed on a schedule of cumulatively repeated phase delays in his activity-rest cycle. During some of these delays, bright light pulses were applied in order to determine the effect of circadian phase delay attributable to the bright light pulses. The phase delay was measured using the Phase Resetting Capacity Assessment Method described above.

The first Constant Routine started before time 502 (FIG. 18). During this Constant Routine, the trough of the deep circadian pacemaker was determined to occur at time 512 (Day 5). In Days 6-9, the subject was entrained to a 24-hour activity-rest cycle. At time 504, a second Constant Routine assessment of the deep circadian pacemaker was performed. As shown at time 514 (Day 10), the deep circadian pacemaker trough was phase-delayed by only 0.9 hours, which is statistically insignificant in light of its accordance with previous results under similar circumstances.

On Day 11, the activity-rest cycle of the subject was delayed by six hours. This delay was enforced from Days 11 to 14. Unlike Days 6-9, during Days 12-14 the subject was exposed to 5.5 hours of bright light on three consecutive nights, as indicated at 526 (FIG. 18). On Day 14, a third Constant Routine was entered. It was determined that the deep circadian pacemaker trough occurred on Day 15 as indicated at time 516. The phase delay between time 514 (Day 10) and time 516 (Day 15) was a statistically significant 7.1 hours. This indicates that the application of bright light pulses on successive nights dramatically shifted the phase of the deep circadian pacemaker by a magnitude which is not explainable either by free-running phase delay or by manipulation of the activity-rest cycle.

Days 15-25 of the experiment basically repeat the procedure of Days 5-15. A 7-hour delay in the enforced activity-rest cycle on Day 16 caused a statistically insignificant phase delay in the deep circadian pacemaker of only 1.9 hours. This phase delay of the deep circadian pacemaker is indicated by the relative times of occurrence of the deep circadian pacemaker troughs at time 516 (Day 15) and time 518 (Day 20).

After another shifting of the activity-rest cycle by 7.5 hours on Day 20, bright light pulses of 5.5 hour duration were applied on Days 21-23. A statistically significant 9.9-hour phase shift in the deep circadian pacemaker is indicated by the relative timing of deep circadian pacemaker troughs at time 518 (Day 20) and time 520 (Day 24/25).

In summary, FIG. 18 graphically demonstrates that the phase-shift of the deep circadian pacemaker in response to bright light pulse applications (minus 7.1 and minus 9.9 hours) is far greater than that (less than 2 hours) explainable either by free-running phase delay or manipulation of the activity-rest cycle.

Figure 19:
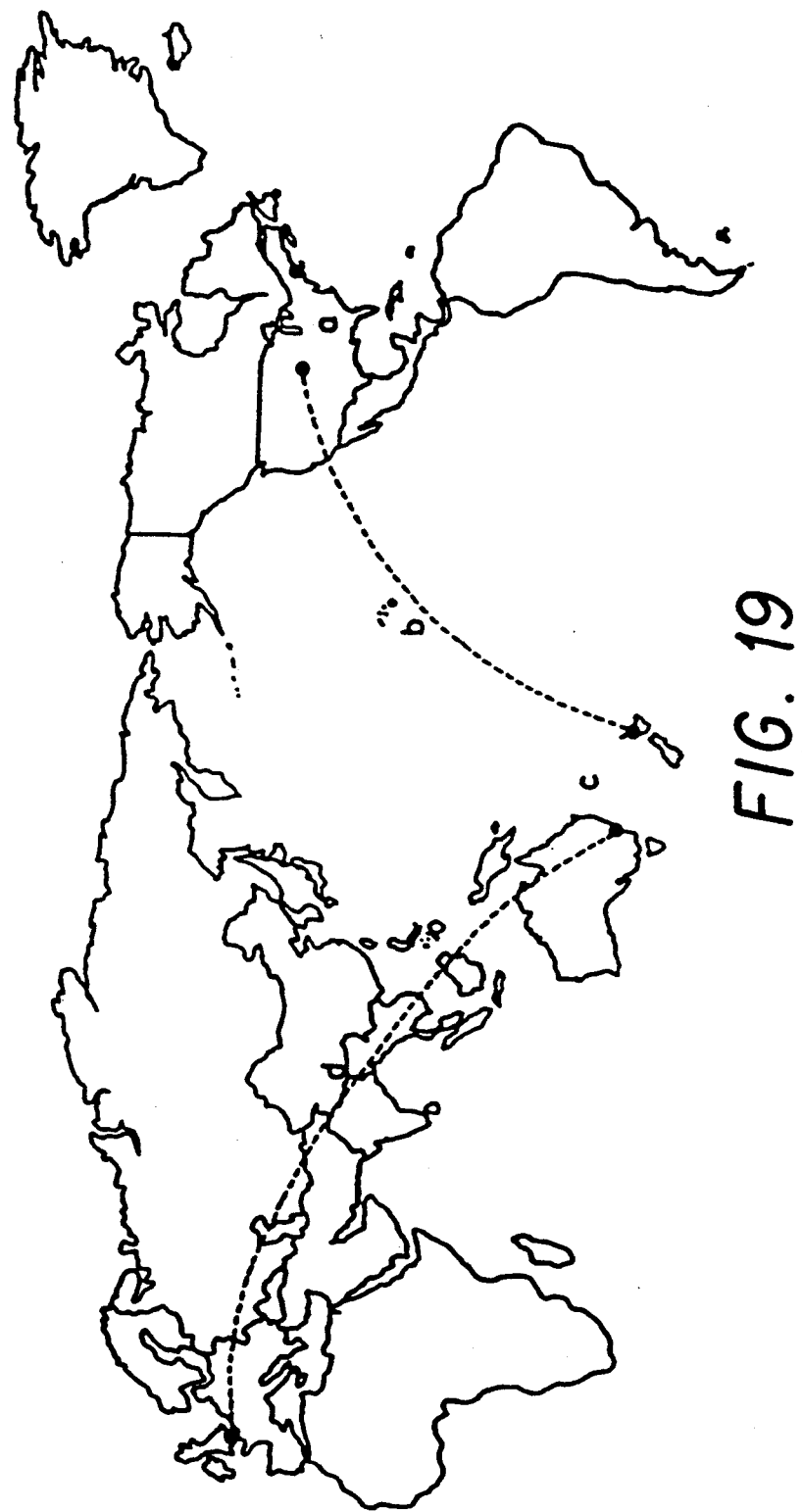
FIG. 19 is a world map indicating the adjustment to transmeridian travel which would be simulated by the specific experiment illustrated in FIG. 18.

FIG. 19 illustrates the effective application of the phase-shifting abilities of bright light pulses according to the present invention to transmeridian travelers. The letters A, B, C, and D indicated in FIG. 19 correspond to the segments so labeled in FIG. 18. During segment A (days 5-10), the endogenous circadian pacemaker of the subject effectively adjusted to a trip equivalent to that of one from New York to Omaha, since the intrinsic period of the pacemaker is greater than 24 hours and the natural tendency of the pacemaker is therefore to drift to later hours.

During segment B (days 10-15), a more dramatic phase shift caused by the application of bright light pulses on three consecutive evenings would have adjusted a traveler's endogenous circadian pacemaker by an amount equivalent to a trip from Omaha to Auckland.

Once in New Zealand, the endogenous circadian pacemaker again drifted to a later hour during segment C (days 15-20) so that the subject's endogenous circadian pacemaker had effectively adjusted to the time in Sydney. Thereafter, in segment D (days 20-25), the acceleration of the phase shifting due to three days of bright light pulse applications effectively adjusted the subject's endogenous circadian pacemaker to a trip from Australia to London.

The relatively short time in which these dramatic phase shifts are accomplished advantageously coincides with the time at which the excessive sleeping (to compensate for sleep deprivation) would otherwise cease to provide symptomatic relief, as described in the Background of the Invention. Thus, methods of endogenous circadian pacemaker phase shifting according to the present invention allow a viable treatment method for transmeridian travelers in a variety of scenarios. Also, the endogenous circadian pacemaker phase shifting according to the present invention allows viable treatment for shift workers in a variety of rotating or otherwise unusual (from the point of view of a diurnal animal) work schedule. For example, FIG. 18 represents a simulation not only of westward travel, but also of a delay shift in the timing of the sleep-wake cycle required of industrial workers when making the transition from day or evening shift work to night shift work. In the case of FIG. 18, it can be seen that the ECP minima are more strategically chosen so as to be maintained in the episodes of enforced darkness (and presumably sleep). As described above, when the ECP minimum is timed to occur within a sleep episode, the sleep tends to be more efficient, and wakeful activity tends to be more productive.

Figure 20:
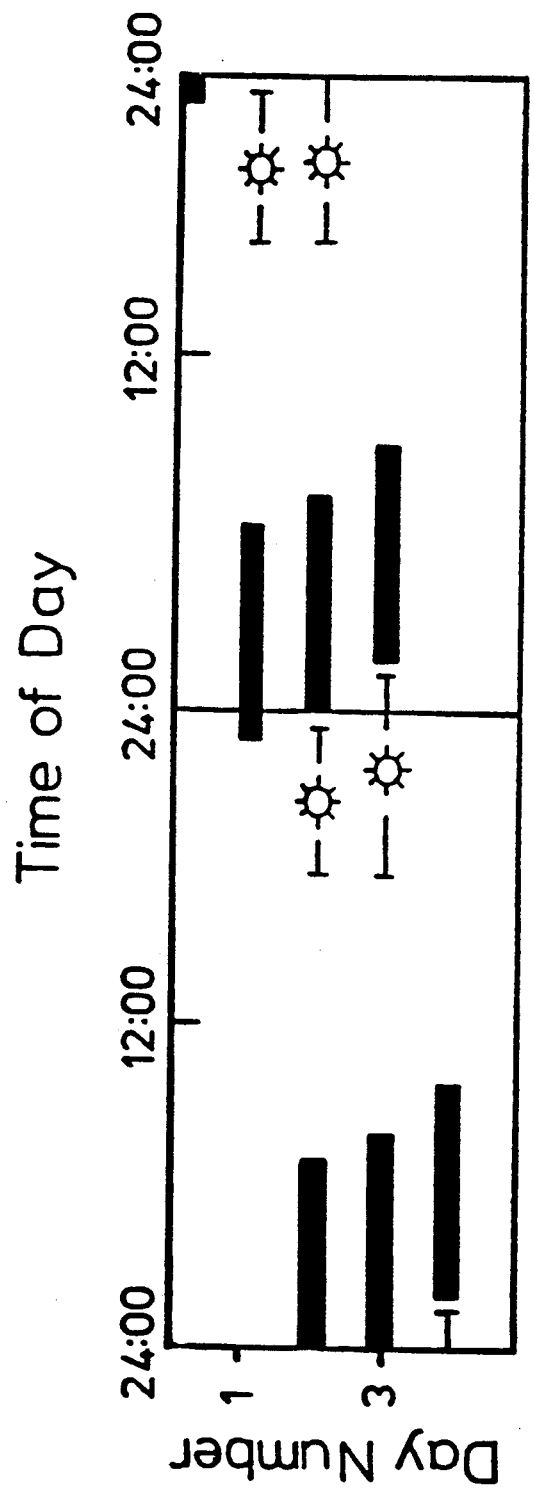
FIG. 20 shows a prototypical schedule for achieving a small phase delay (about 3 hours).

(1) FIG. 20 depicts a schedule, plotted in double raster format, which is optimally suited for achieving a delay shift of approximately 3 hours. Such a delay would be typically required of travellers flying from New York to San Francisco. This schedule utilizes a protocol which resets circadian phase with little effect on circadian amplitude (i.e., Type 1 resetting). The first solid bar represents the individual's habitual sleep/dark episode (typically occurring from 23:30 to 07:30). On the next day, which could be the day before travel, bed time and wake time are moved an hour later, and approximately 4-5 hours of bright light (at least 7,000-12,000 lux) are administered just prior to the sleep/dark episode. On the following day, which could be the day of travel, bed time and wake time are moved an additional hour and a half later, and approximately 5-6 hours of bright light are administered just prior to sleep. If convenient, the bright light could be administered on the airplane flight while en route. This could fit in quite well aboard evening non-stop flights from New York to San Francisco. Should additional phase delay shift be required, this schedule can be continued. However, if a more acute shift is desired, a schedule employing type 0 (amplitude reducing) phase resetting would be faster.

(2) Eastbound travelers (e.g., Seattle to Paris) or shift workers making the transition from evening shift to night shift are often required to accomplish a nearly complete inversion of their sleep-wake cycle (a shift requiring a 10-12 hour delay or a 10-12 hour phase advance) when they travel from the Orient to many parts of the Western world, or when industrial workers must rotate from day work to night work. When the shift required is 10 hours or greater, it cannot practically be accomplished via Type 1 resetting, since 1-2 weeks would be required before the shift were complete. Therefore, the best strategy is to center the light exposure on the circadian temperature minimum and to schedule the timing of sleep/darkness such that it is most conveniently placed with respect to the industrial work schedule or the new time zone. It should be emphasized that the room used for sleeping should be dark and shield out environmental or artificial light sources.

The potential clinical utility of the inventive method to reset human circadian phase has been documented in a follow-up case study of the elderly subject in panel B of FIG. 7 who was an extreme example of the phase advance of the circadian pacemaker which occurs with advancing age. Panel B of FIG. 7 is a comparison of baseline and constant routine temperature data (solid line) in a healthy, 66 year old woman. These data are superimposed upon normative ($\pm$S.E.M., vertical hatch marks) temperature data collected from 29 young, normal subjects on the same protocol. Data from the normal controls are averaged with respect to a nominal reference bedtime of 24:00. The black bar represents her bedrest episode which was scheduled at its regular time. Hatched bar represents constant routine assessment of phase and amplitude. The encircled cross marks the minimum of the fitted endogenous temperature rhythm. Note that the ECP minimum occurred at 11:35 p.m., approximately 5 hours earlier than would be expected on the basis of the normative data. However, this phase shift is not apparent during the night preceding the Constant Routine because of masking effects. The rhythm of cortisol secretion was similarly phase advanced during her Constant Routine. Her marked phase advance was confirmed on two subsequent repetitions of this protocol. This condition is often associated with the early bed and wake times often found in the elderly.

Figure 21:
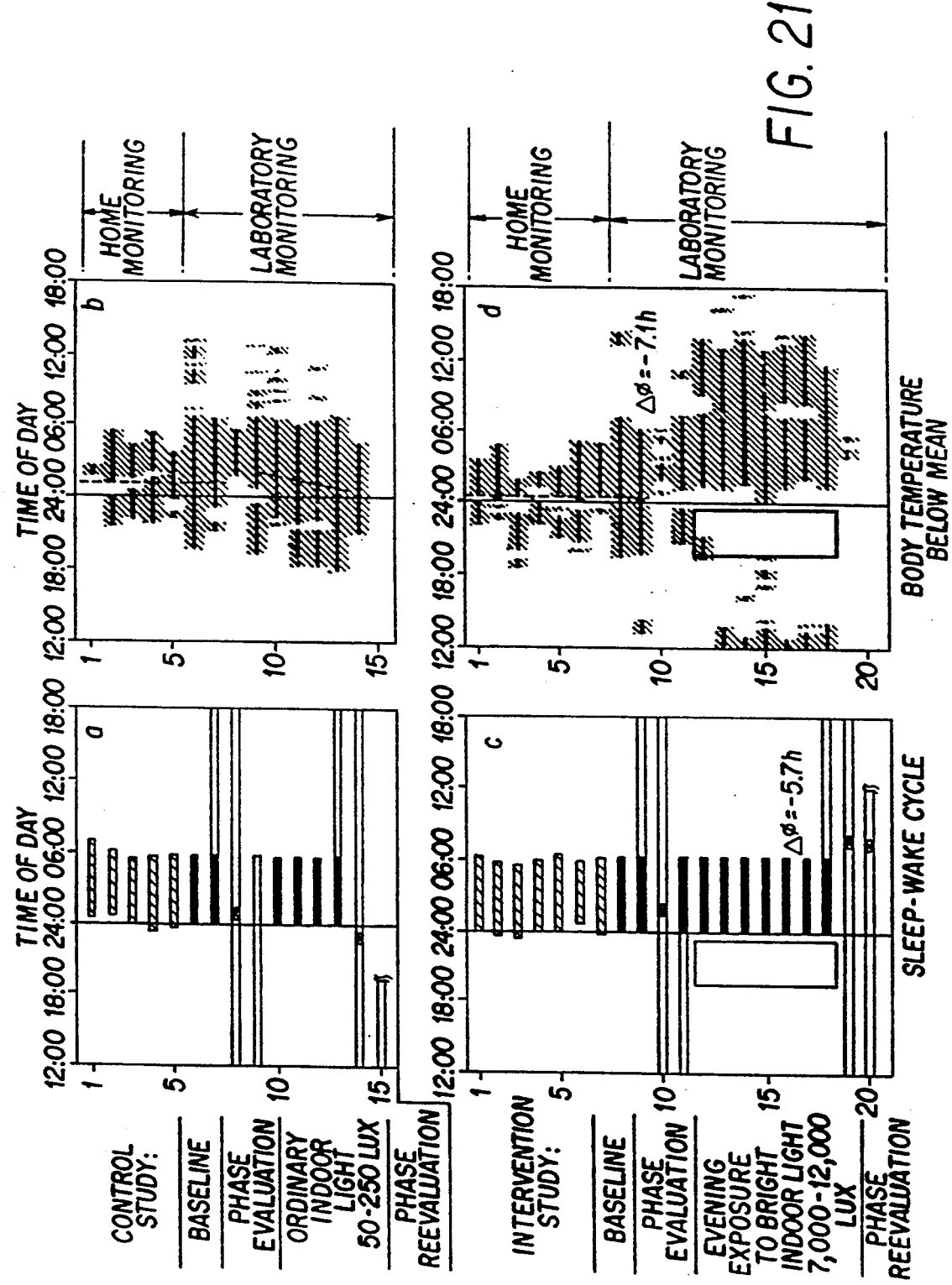
FIG. 21 shows how bright light can reset the circadian oscillator independent of the timing of sleep/darkness: the use of evening bright light to treat advanced circadian phase.

FIG. 21 shows a controlled study in which evening exposure to bright indoor light resets the circadian pacemaker of this subject by about six hours, even while her rest-activity cycle is held fixed. Symbols are as previously described with hatched bars indicating bed-rest episodes during ambulatory monitoring. Panel (A) (upper left) shows ECP evaluations before and after entrainment schedule involving exposure to ordinary room light suggest a non-significant drift of the endogenous circadian pacemaker. Panel (B) (upper right) shows a raster plot of body temperature troughs during control study. Horizontal black bars with stippling highlight the specific times and days when body temperature was below the baseline entrained mean. Note the absence of a phase shift during exposure to ordinary room light in the laboratory. Panel (C) (lower left) shows ECP evaluations before and after entrainment schedule as described in A, with the addition of an intervention stimulus with evening exposure to bright indoor light demonstrating a 5.7 hour phase delay shift of the circadian pacemaker. Symbols as in (A). The subject was exposed to bright indoor light (7,000–12,000 lux) between 19:40 and 23:40 each day for seven days. Fifteen minutes of intermediate level light (3,000–6,000 lux) preceded and followed each four hour exposure. Panel (D) (lower right) shows a raster plot of body temperature troughs before and during the intervention study confirming the magnitude of the phase delay shift previously shown in (C).

Figure 22:
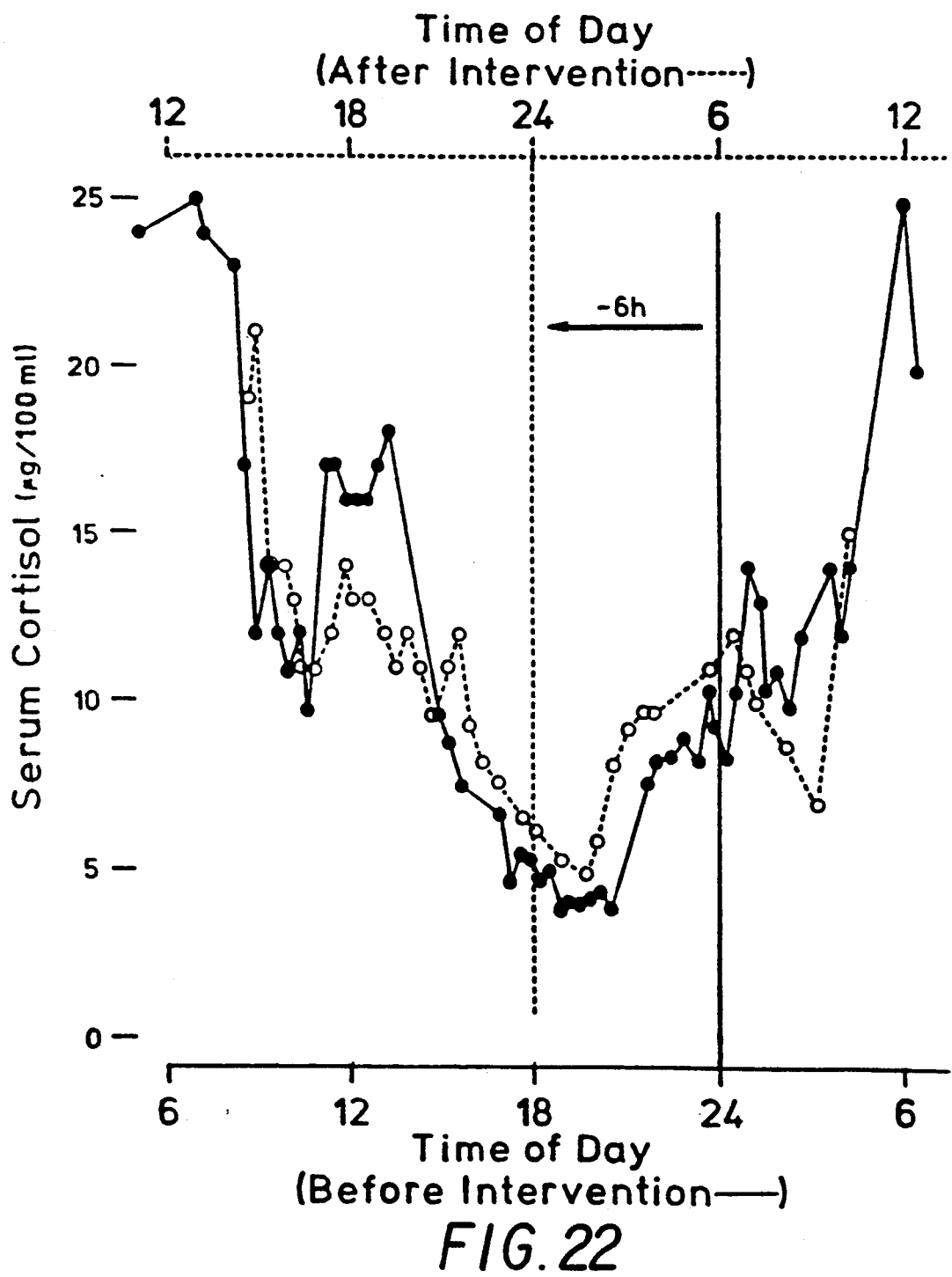
FIG. 22 shows phase displacement of cortisol rhythm following exposure to light in a patient with advanced circadian phase.

This apparent phase shift was confirmed by a similar shift in the rhythm of serum cortisol (FIG. 22), another marker of the circadian pacemaker. To align the episodic cortisol secretory patterns before and after invention with bright indoor light, their horizontal time scales have been shifted by six hours. Blood samples were collected while the subject was in ordinary room light (50–250 lux) during Constant Routines performed immediately before and after the intervention. The pattern after the intervention (open circles and dashed line) have been translated six hours to the left along the pre-intervention axis (solid axis), thereby aligning the two waveforms. The plot shows that the intervention did not change the shape of the pattern but phase delayed it by approximately six hours.

b. Advancing Circadian Phase Using Experimentally Derived Data

Advancing circadian phase is desirable for eastward jet travelers, shiftworkers who must rotate to an earlier shift (i.e., counterclockwise rotation), and patients with an undesirably delayed sleep phase (i.e., Delayed Sleep Phase Syndrome, typically but not exclusively found in the young).

Phase advances of 2–11.5 hours have been achieved in 2–3 days' time by appropriately structuring these days' lighting schedules with particular attention to the timing of bright light and darkness.

In order to best design the lighting schedule, one must have knowledge of the initial circadian phase of the person to be treated. This is best achieved by the previously described embodiment known as the Constant Routine. However, it would be acceptable in most cases to infer such phase based on comparisons made to the body of normative phase data such as is contained within this specification, or in the literature in general.

By subtracting the initial phase from the desired phase, the magnitude and direction of the required phase shift is determined. Then, by interpolation of FIG. 11, the optimum time to begin the administration of a bright light pulse is determined. This bright light pulse is approximately five hours in duration and has a dosage of approximately 7,000–12,000 lux in a preferred embodiment. Light of half intensity may precede and follow this five-hour pulse for approximately 15 minutes.

By interpolation of FIG. 14, the optimum time to begin the dark (sleep) pulse is determined. The dark pulse lasts from approximately six to nine hours in a preferred embodiment. The retina of the eye should be appropriately shielded from all light.

At times not specified above, the person being treated should be exposed to light of normal indoor intensity (ca. 100–500 lux).

This lighting schedule is repeated for three days in a preferred embodiment. Upon completion of the regimen, the desired phase shift will have been achieved.

FIG. 1 illustrates an example of an individual being phase advanced using this technique, by an amount of eastward travel equivalent to a trip from Seattle to London. Five hours of full bright light (7,000 to 12,000 lux) exposure was initiated at 6:30 A.M. (with 15 minute transitions of 3,000 to 6,000 lux preceding and following the 5 hour full-bright light exposure), about 1.5 hours before his 8:00 A.M. ECP temperature minimum (as determined by an initial Constant Routine in this case or as could have been surmised from the approximately 9:30 A.M. traditional wake-time of this young man using the normative data of FIG. 5). The individual's daily sleep episode was concurrently rescheduled from his approximate habitual bed/dark time of 2:30 A.M. and his approximate habitual wake/lights-on time of about 9:30 A.M. to occur eight hours earlier from 5:30 P.M. to 1:30 A.M.; as if he had traveled from Seattle to London. Follow-up ECP evaluation revealed that his temperature minimum had phase shifted eight hours. This same type of light/dark lighting schedules could also have been used to phase advance shift factory workers rotating from a schedule requiring them to work at night and sleep in the morning to one requiring them to sleep at night and work during the day shift. For such changes in sleep schedule required by rotating shift work schedules, whether they rotate in a clockwise or counter-clockwise direction of shift rotation, exposure of the shift workers to bright lights in the workplace during the last 4–5 hours of the day shift (from about 11:00 A.M. to 4:00 P.M.) may markedly enhance their adjustment to the schedule, raise their daytime alertness, efficiency and performance, improve their sleep at home and reduce their proneness for accidents at work. The exact timing of light exposures to be used for rotating shift workers would depend on the specifics of their work schedule, their working conditions (e.g., amount of exposure to outdoor light at work), their average age and the amount of natural light to which they will be exposed to commuting to and from work. Someone skilled in the art could draw upon the information in FIGS. 11 and 14, together—if necessary—with the mathematical model described below, to develop a paradigm most suitable for the employees concerned. An alternative strategy may be to reduce the circadian amplitude of shift workers via timed exposure to bright light just prior to shift change transitions, thereby facilitating their adaptation.

Figure 23:
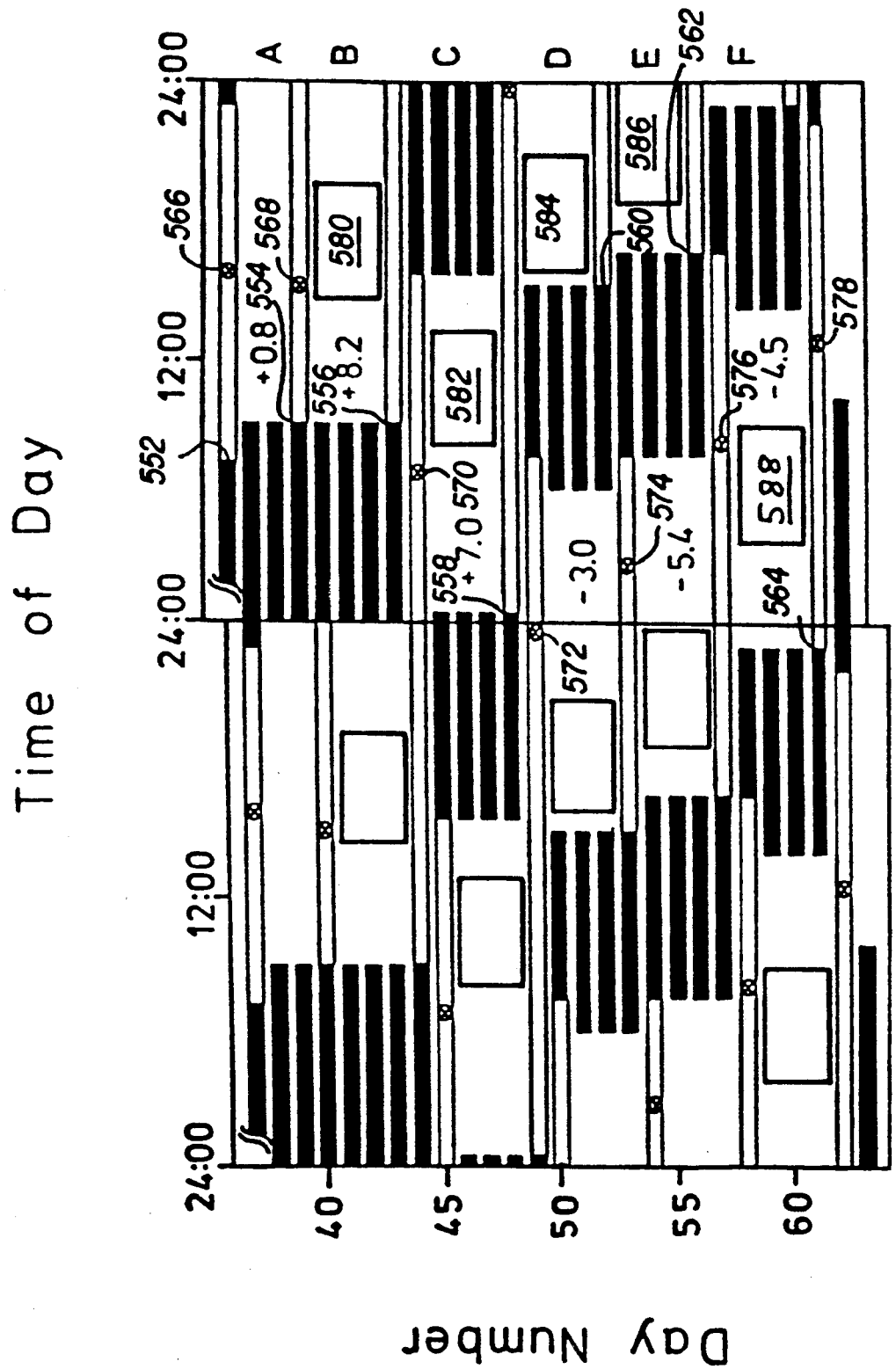
FIG. 23 is a raster plot of laboratory simulation of world travel, including phase advances and phase delays of varying magnitude.

FIG. 23 is a raster diagram similar to the raster diagram of FIG. 18. FIG. 23, however, involves not only phase delays, but also phase advances.

As in FIG. 18, hollow horizontal bars indicate periods of wakefulness, and solid horizontal bars indicate periods of enforced bedrest. At times 552, 554, 556, 558, 560, 562, and 564, Constant Routines were entered in order to determine the time of occurrence of endogenous circadian pacemaker minima at 556, 568, 570, 572, 574, 576, and 578, respectively. At various points in this laboratory experiment, bright light pulses of 5-hour duration were applied on three consecutive days at the same time, as indicated at 580, 582, 584, 586, and 588.

The timing of application of bright light pulses, as well as the timing of periods of darkness, modified the phase so as to cause controllable phase advances or delays.

During segment A, the subject was entrained to a 24-hour cycle of darkness and light. During this period of entrainment, it can be seen that the ECP phase advanced by 0.8 hours from 566 to 568. (It is unusual for a human subject to display an intrinsic period, $\tau_x$ of less than 24 hours.) During segments B and C, bright light pulses were applied on three consecutive days, as indicated at 580 and 582, respectively. FIG. 23 clearly shows that the bright light pulse groups 580 and 582 occur substantially after the ECP temperature minima 568 and 570, respectively. As a result of the timing of these bright light pulses, in conjunction with the advancement by approximately 8 hours of the darkness onset, ECP phase advances of 8.2 hours and 7.0 hours, respectively, were observed.

Bright light pulse groups, each of 5-hour duration on three consecutive days, were imposed as indicated at 584, 586, and 588. These three bright light pulse groups were timed to be substantially before the ECP minima at 572, 574, and 576. The timing of these bright light pulses, in conjunction with the phase delays indicated by the right shifting of the periods of enforced darkness in segments D, E, and F, caused phase delays of 3.0 hours, 5.4 hours, and 4.5 hours, respectively.

Figure 24:
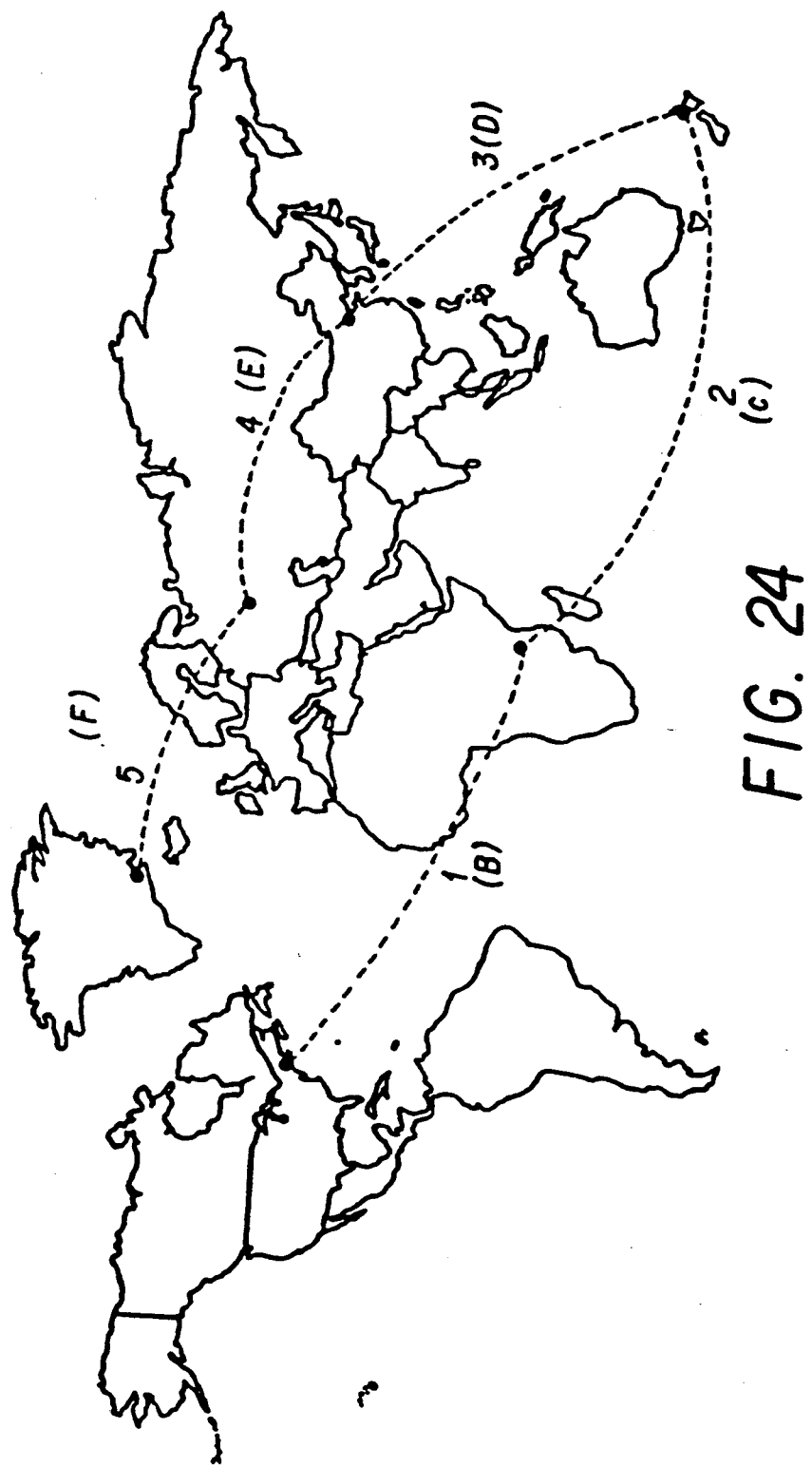
FIG. 24 is a graphical representation of itinerary simulated in FIG. 23.

Referring to FIG. 24, the laboratory experiment recorded in FIG. 23 can be thought of as simulating a transmeridian trip of intercontinental dimensions. The segments B, C, D, E, and F shown in FIG. 23 correspond to the simulated phase shift which would be advantageously experienced by a traveler with the itinerary illustrated in FIG. 24. The 8.2-hour and 7.0-hour phase advances noted in segments B and C would be ideal adjustments to a person traveling from Boston to Nairobi, and then from Nairobi to Auckland. Similarly, the phase delays of 3.0 hours, 5.4 hours, and 4.5 hours, would allow adjustment of people traveling from Auckland to Peking, and then on to Moscow and Greenland.

While it should be recognized that it is not generally desirable to experience the ECP temperature minima during the middle of the day time (which is the case in all the FIG. 23 ECP minima), and whereas it may not be practical for many travelers to expose themselves to pulses of bright light and darkness exactly as indicated, the effectiveness of pulses of bright light and enforced darkness in shifting the ECP temperature minima are clearly demonstrated. Variations on light/dark regimens which are more practical, although perhaps not as efficient, will become clearer upon an understanding of the principles expressed in the remainder of this disclosure. Based on either empirically-derived phase response curves, or upon a mathematical model, the most effective practical light/dark regimen may be designed to fit within a schedule of predefined episodes of darkness and ordinary room illumination.

For illustrative purposes, we give examples of lighting schedules which will facilitate (1) a three-hour delay shift, and (2) a ten-hour delay shift. Consideration has been given both to experimental optimization and practical convenience.

Figure 25:
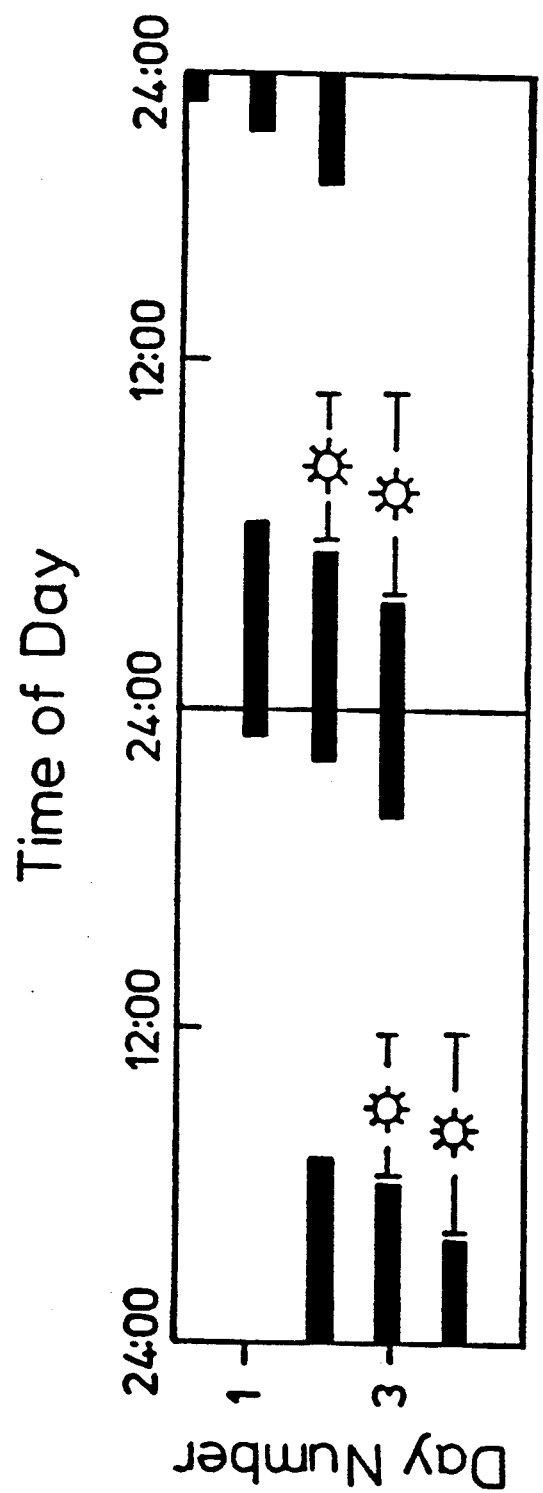
FIG. 25 shows a prototypical schedule for achieving a small phase advance (about 3 hours).

FIG. 25 depicts a schedule, plotted in double raster format, which is optimally suited for achieving an advance shift of approximately 3 hours. Such an advance would be typically required of travellers flying from, for example, San Francisco to New York. This schedule utilizes a protocol which resets circadian phase with little effect on circadian amplitude (i.e., Type 1 resetting). The first solid bar represents the individual's habitual sleep episode (typically occurring from 21:30 to 07:30). On the next day, which could be the day before travel, bed time and wake time are moved an hour earlier, and approximately 4–5 hours of bright light (at least 7,000–12,000 lux) are administered upon waking. On the following day, which could be the day of travel, bed time and wake time are moved an additional hour and a half earlier, and approximately 5–6 hours of bright light are administered upon waking. If convenient, the bright light could be administered while en route. This would be ideal if the bright light could be administered aboard the aircraft on the nonstop daily morning flight from San Francisco to New York. Such light exposure could occur via a specially equipped airplane fitted with a cabin with bright light or via the portable goggle units described below.

Figure 26A:
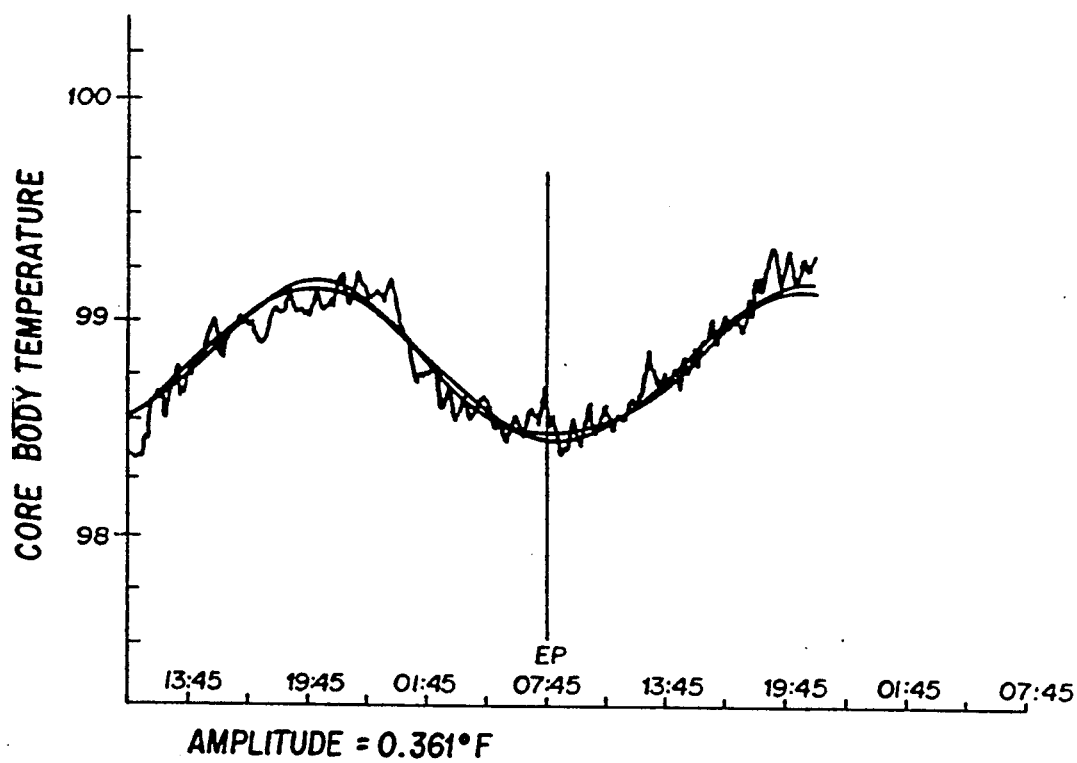
FIG. 26a shows the endogenous component of the temperature cycle during a constant routine before treatment intervention.
Figure 26B:
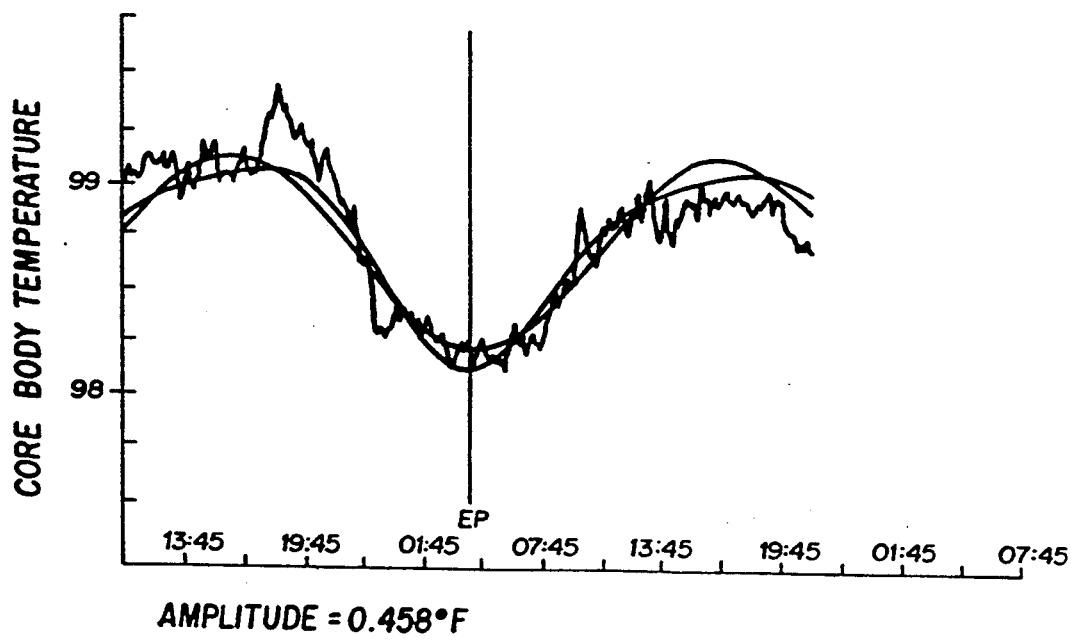
FIG. 26b shows the endogenous component of the temperature cycle during a constant routine after daily morning exposure to bright light.
Figure 27:
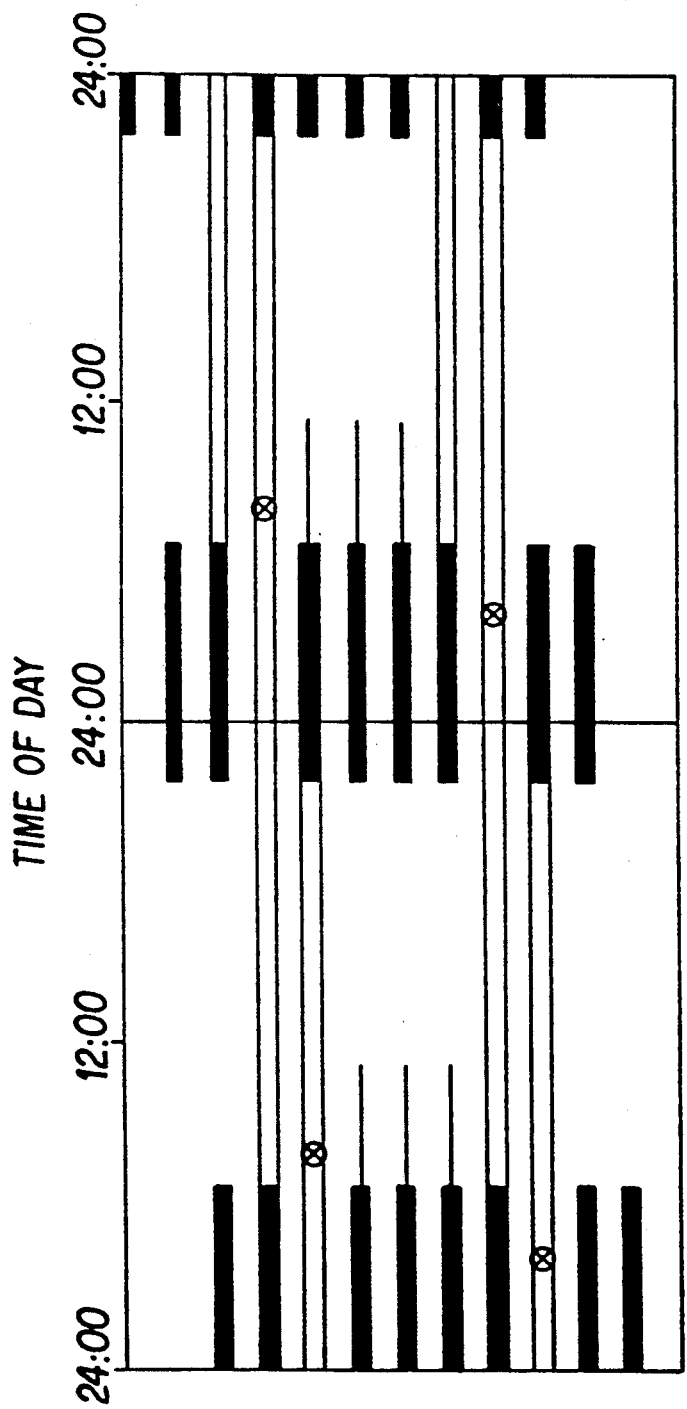
FIG. 27 is a raster plot of protocol used in the assessment and treatment of the patient described in FIG. 26.

A very similar protocol can be used to treat patients with Delayed Sleep Phase Syndrome (DSPS). FIG. 26A illustrates the endogenous circadian phase of a 52-year-old woman with DSPS, a sleep scheduling disorder characterized by sleep onset insomnia and excessive daytime sleepiness in the early morning. The panel shows the endogenous component of the temperature cycle during a constant routine before treatment intervention. The patient was treated with three exposures of morning light, without shifting the time of her scheduled sleep-wake cycle, to determine whether her circadian pacemaker could be phase advanced to an earlier hour without disrupting her habitual sleep time (the protocol is illustrated in FIG. 27). After only three daily morning exposures to bright light, her circadian pacemaker was phase advanced by nearly 4 hours, to a position normal for a woman of her age (see FIGS. 26B and 27), and the patient—who had a greater than 5 year history of DSPS—reported an immediate remission from her debilitating symptoms which had interfered with her ability to carry out her profession.

Figures 28A, 28B:
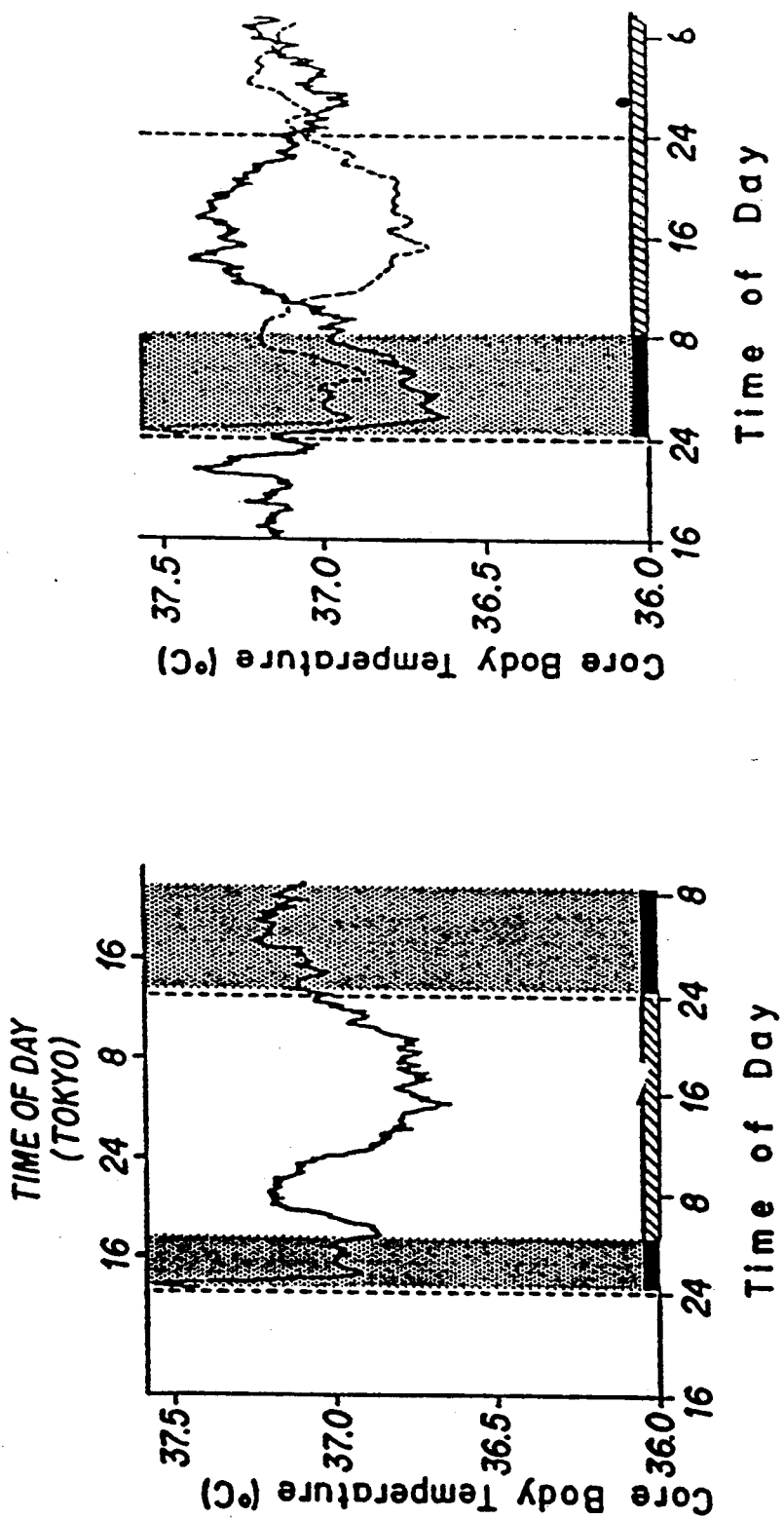
FIG. 28a shows the pre-intervention assessment of the circadian phase of a jet traveler flying from the Orient to Boston.
FIG. 28b shows the post intervention assessment of the circadian phase of a jet traveler flying from the Orient to Boston.
Figure 29:
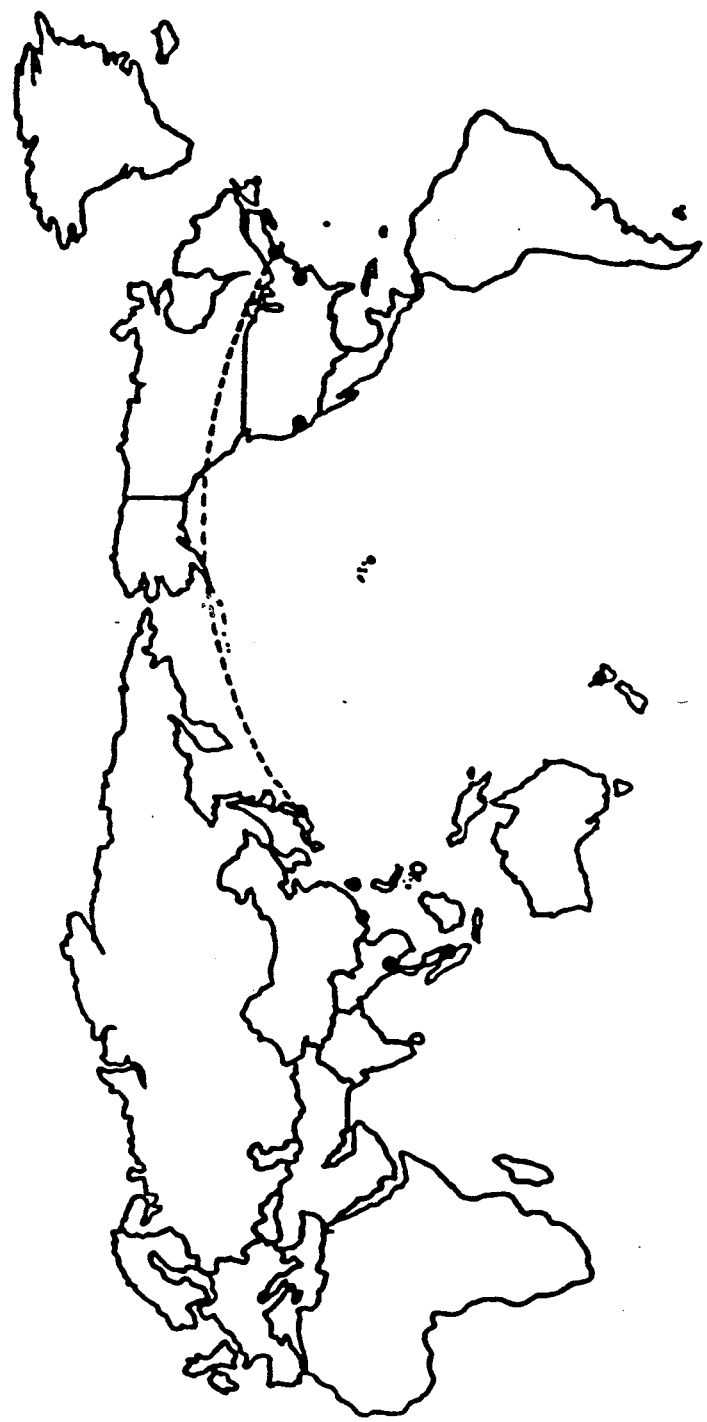
FIG. 29 is a graphical representation of the traveler whose circadian phase was assessed in FIG. 28.
Figure 30:
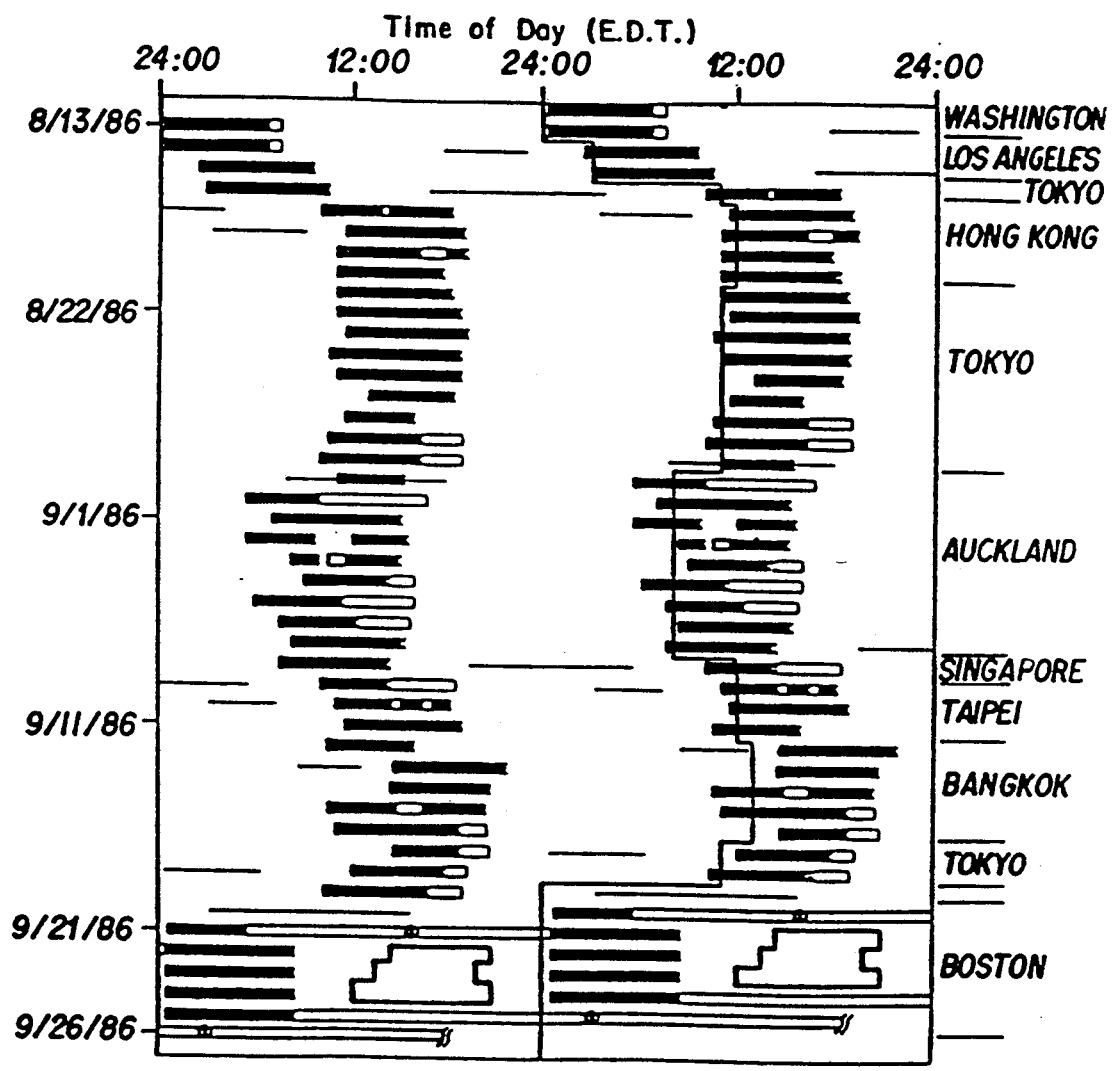
FIG. 30 is a raster plot of travel log, assessment, and treatment of the traveler of FIG. 28.

This approach has been reduced to practice in the following example. FIG. 28A and FIG. 28B show the output of the internal body clock as measured during a Constant Routine from a traveler just after returning from Tokyo to Boston (FIG. 29), before any treatment. Note that he reached the low point of his body temperature cycle (the time of greatest sleepiness, lowest performance and peak accident risk) ar about 4.00 p.m. Boston time (lower horizontal axis, FIG. 28A and 28B), and he would have ordinarily been asleep, as shown in FIG. 30, which is a raster plot of his travel schedule during that time. But it was highly inappropriate for Boston, where such a misalignment of phases made it difficult for him to remain awake during the local daytime without using stimulants and difficult to sleep at night without the use of sleeping pills. Instead, this traveler was exposed to three daily pulses of bright light and his daily sleep episode was rescheduled to Boston time. Three days after his return to Boston, when the effects on sleep and daytime alertness of "jet lag" from time zone inversion are typically at their worst, his internal clock was instead completely reset by the treatment, with the peak in his daily temperature cycle occurring where the trough had been (FIG. 29). He then felt fully alert during the local daytime and slept well at night, without stimulants or hypnotics. This same process could be applied to make it easier for shift workers to adjust to night work.

c. Reducing Circadian Amplitude Using Experimental Data

Reduction in circadian amplitude is desirable in order to place the circadian timing system in a more labile position, as would be desired when anticipating a change in circadian phase. This procedure would be desirable for travelers crossing many time zones or the shift worker making a change in worktime. As circadian amplitude is sufficiently reduced, the circadian timing system is correspondingly sensitized to a single day's lighting cycle. Thus, travelers or workers who intend to be exposed to the environmental lighting schedule (or a regimen of indoor bright light exposure designed to approximate environmentally available light) immediately upon assuming their new schedule could benefit greatly from a preparatory reduction in circadian amplitude.

There is a range of amplitude reduction which can be achieved using specifically timed regimens, which optimally include both episodes of darkness and episodes of bright light exposure. It is possible to effectively reduce circadian amplitude to zero in two days of scheduled light exposure.

In order to best design the lighting schedule, one must have knowledge of the initial circadian phase of the person to be treated. This is best achieved by the previously described embodiment known as the Constant Routine. However, it would be acceptable in most cases to infer such phase based on comparisons made to the body of normative phase data such as is contained within this specification, or in the literature in general.

The optimal lighting schedule in order to effect amplitude reduction is one in which bright light (ca. 7,000–12,000 lux) of approximately six hours' duration is centered around the time of the endogenous temperature minimum as determined by the embodiment of the Constant Routine or normative data. A seven-to-eight-hour episode of absolute darkness (sleep) ideally should be placed in a position such that the midpoint of the dark episode is 180° (12 hours) from the mid-point of the bright light exposure. This regimen is repeated for two days in the preferred embodiment.

Slight modifications in the timing of the light or dark stimulus will result in a partial attenuation of amplitude, most likely with an attendant alteration in phase. If this schedule were substantially altered or inverted, one could expect an increase in circadian amplitude, if amplitude were initially at a nominal or sub-nominal value.

Figure 31:
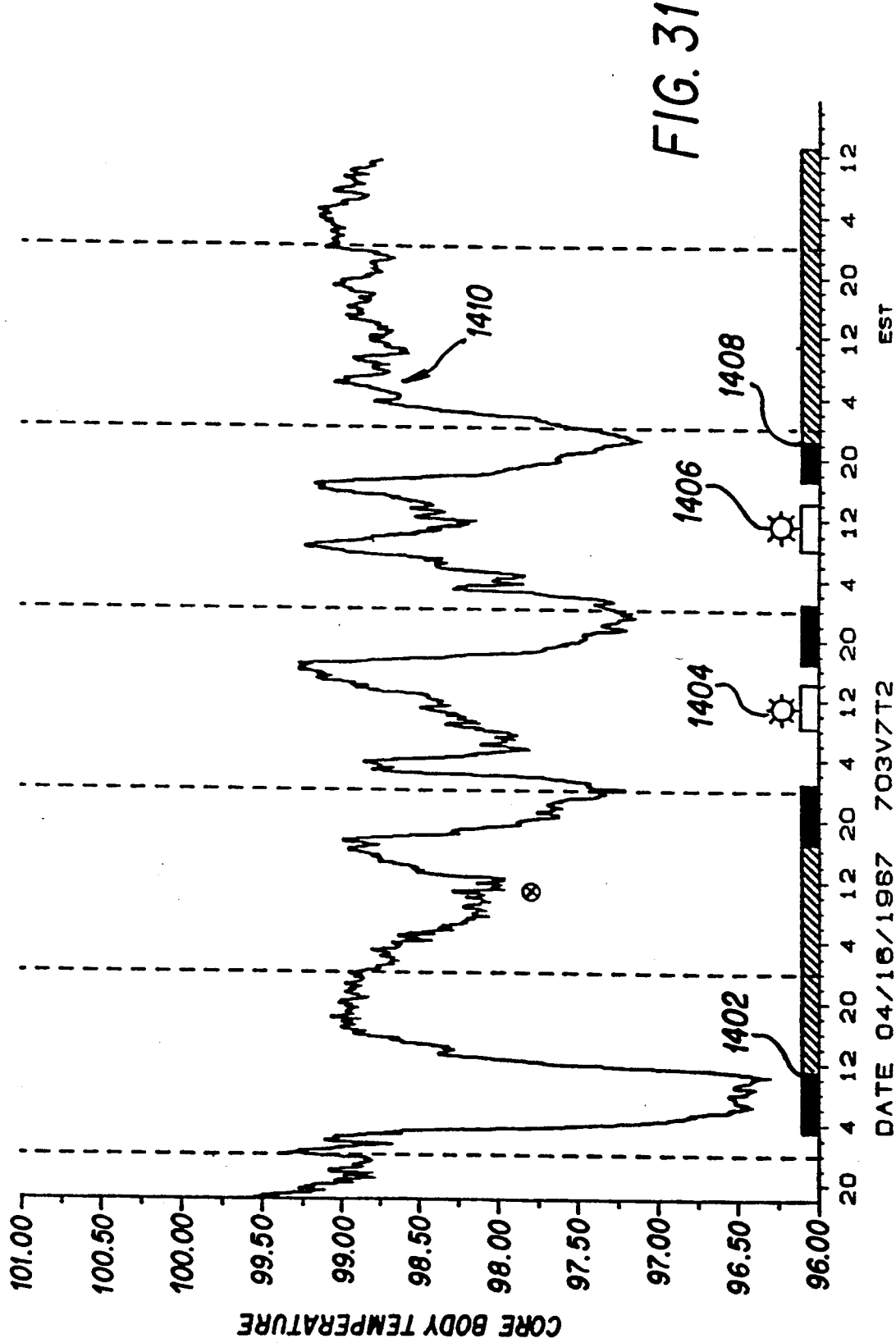
FIG. 31 is an actual timing diagram of the core body temperature of a subject whose endogenous circadian pacemaker has been driven to zero amplitude.

FIG. 31 illustrates the actual measured core body temperature of a human subject as a function of time. The subject underwent Constant Routines beginning at times indicates by 1402 and 1408. Between these two Constant Routines, however, two bright light ipisodes indicated as 1404 and 1406, were imposed.

An amplitude reduction to near zero is shown at 1410, after the commencement of the second Constant Routine. After time 1410, the peak-to-peak amplitude of the endogenous circadian pacemaker, as measured by the fitted core body temperature variation was reduced from 2°–3° F. to a level below detection.

d. Increasing Circadian Amplitude Using Experimental Data

Increasing circadian amplitude is desirable in those individuals who are or wish to be stably entrained to a schedule to which they are already phase aligned. By increasing circadian amplitude, the circadian timing system is made more resistant to perturbations. Such an increase in amplitude may benefit a straight night shift worker who wishes to be entrained to the night schedule, yet on weekends tends to alter his schedule to facilitate his social life. Likewise, the straight day worker whose amplitude was increased could better tolerate a few late weekend nights and still be prepared for work early Monday morning. Thus, it is conceivable that augmented morning light exposure, either through appliances in the home or work place, or by way of a portable device on the way to work, will improve daily alertness, performance and memory, which are known to fluctuate with the core body temperature cycle. (See Czeisler, C. A., Kennedy, W. A., Allan, J. S., "Circadian Rhythms and Performance Decrements in the Transportation Industry." *Proceedings of a Workshop on the Effects of Automation on Operator Performance*, Coblenz, A. M., ed., Commission des Communautes Europeennes, Programme de Recherche Medicale et de Santé Publique, Universite Rene Descartes: Paris, 1986, pp. 146–171.)

There is a range of amplitude augmentation which can be achieved using specifically timed regimens, which optimally include both periods of darkness and periods of bright light exposure. It is possible to effectively increase circadian amplitude in one or two days of scheduled light exposure.

In order to best design the lighting schedule, one must have knowledge of the initial circadian phase of the person to be treated. This is best achieved by the previously described embodiment known as the Constant Routine. However, it would be acceptable in most cases to infer such phase based on comparisons made to the body of normative phase data such as is contained within this specification or in the literature in general.

The optimal lighting schedule in order to effect amplitude augmentation is one in which bright light (ca. 7,000–12,000 lux) of approximately six hours' duration is diametrically opposed to the time of the endogenous temperature minimum as determined by the embodiment of the Constant Routine or normative data. A seven-to-eight-hour period of absolute darkness (sleep) ideally should be centered around the endogenous temperature minimum. This regimen may be applied chronically, if desired, as the amplitude of the circadian timing system over several weeks' time will slowly return to a nominal value following an amplitude perturbation.

Figure 32:
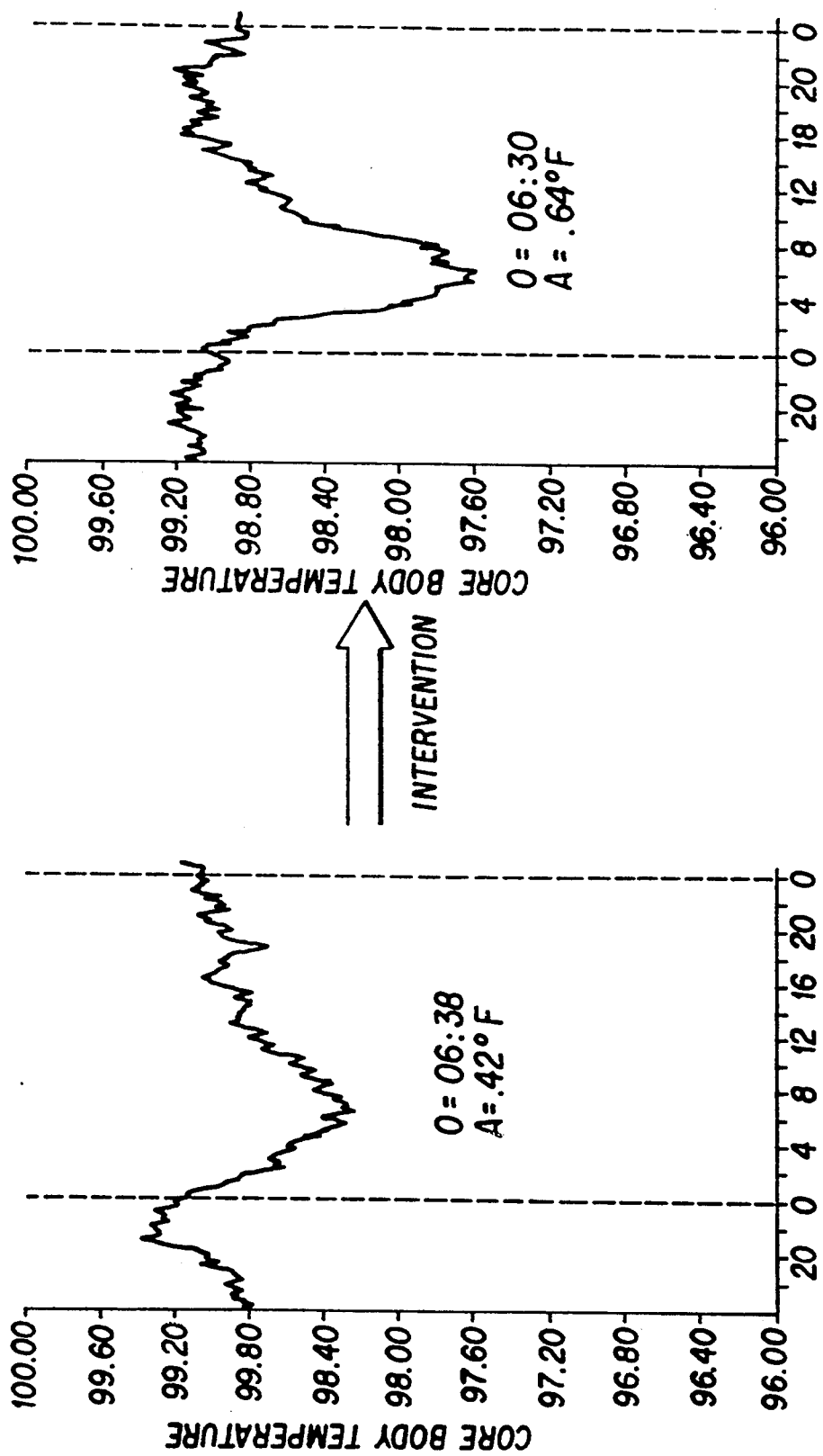
FIG. 32 shows how circadian amplitude is increased with light.
Figure 33:
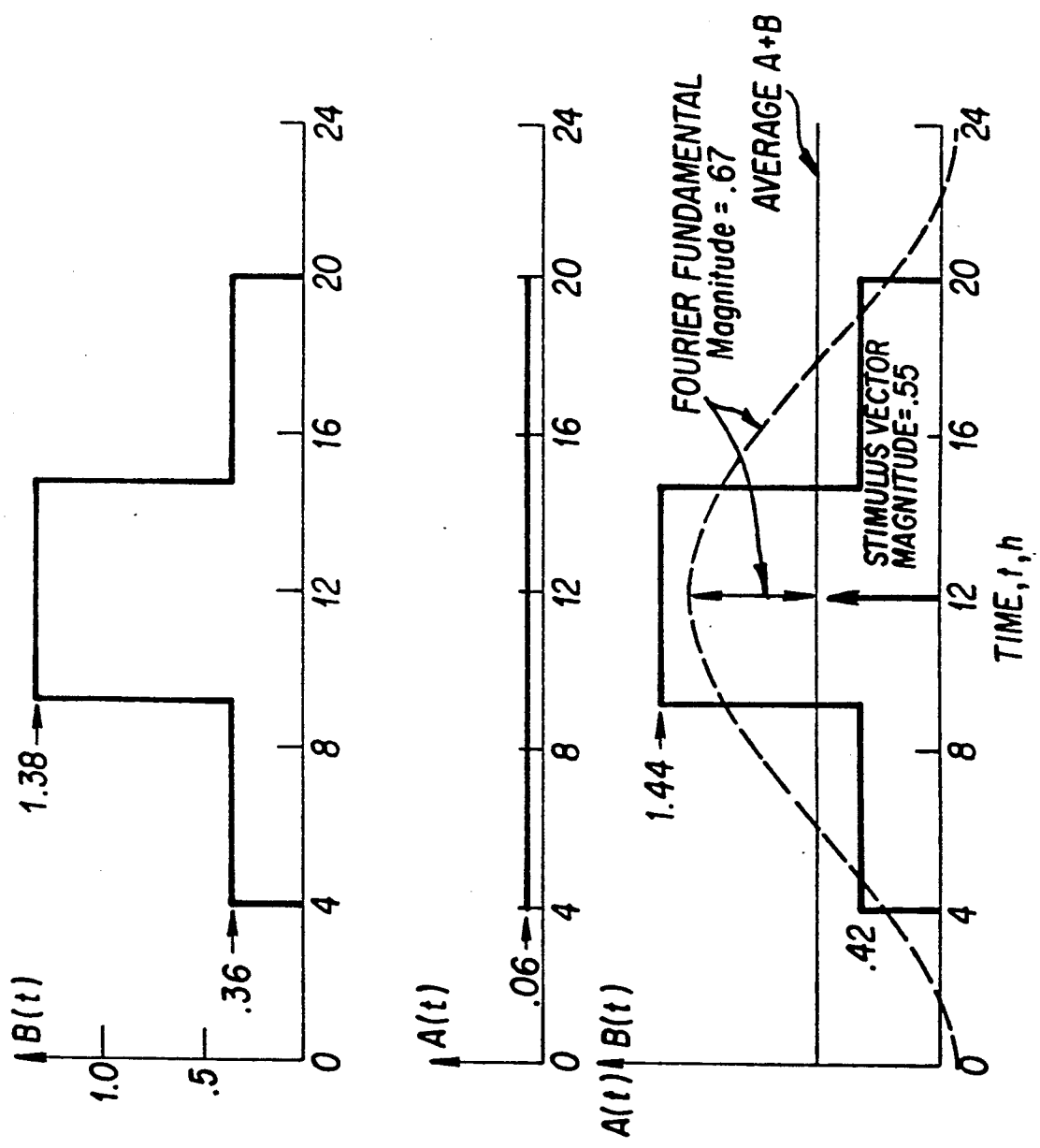
FIGS. 33A, 33B and 33C show the separate, and the summed, Brightness function B(t) and the Activity function A(t), along with the resultant stimulus vector using a Fourier fundamental.

The left panel of FIG. 32 shows a pre-intervention Constant Routine assessment of the endogenous circadian temperature rhythm of a normal male subject. The right panel shows the result of the post-intervention phase and amplitude assessment. Note that there is little change in the phase of the endogenous temperature cycle minimum; however, there is a marked increase of the amplitude of the rhythm.

Slight modifications in the timing of the light or dark stimulus will result in a partial augmentation of amplitude, most likely with an attendant alteration in phase. If this schedule were substantially altered or inverted, one could expect a decrease in circadian amplitude, if amplitude were initially at a nominal or supra-nominal value.

5. Theoretical (Model-Based) Foundation for the Inventive Techniques to Modify Circadian Phase and Amplitude The endogenous (deep) circadian pacemaker, hereafter designated as "the x oscillator," or simply "x," may be modelled mathematically by a second-order differential equation of the van der Pol type, specifically:

$$(12/\pi)^2 \frac{d^2x}{dt^2} + \mu_x(1 - x^2/4)\frac{12}{\pi}\frac{dx}{dt} + (24/\tau_x)^2 x = F_x \quad (1)$$

In the form given, time t is measured in clock hours. The parameter $\mu_x$ is the "stiffness" of the x oscillator and for normal humans is expected to be in the range $0.05 \leq \mu_x \leq 0.15$ with 0.1 as the representative value. The estimate of 0.1 for $\mu_x$ was originally chosen as a trial value by analogy with the value of $\mu_y$ (the internal "stiffness" of the y oscillator) of the dual oscillator model of the human circadian timing system (see R. E. Kronauer et al., "Mathematical Model of the Human Circadian System with Two Interacting Oscillators," *Am. Journal of Physiology*, Vol. 242, pp. R3–R17, 1982), which had been validated by earlier experimentation characterizing a phenomenon called phase trapping. Our experimental success in manipulating the amplitude of the oscillatory output implies that $\mu_x$ is very unlikely to be larger than 0.15, and certainly not larger than 0.2. An oscillator with an internal stiffness coefficient less than 0.03 would be unreasonably susceptible to external influences and therefore physiologically incompatible with the observed robustness of the endogenous circadian ("x") oscillator sensitive in this context. The parameter $\tau_x$ represents the intrinsic period of the x oscillator and for normal humans is expected to be in the range $23.6 \leq \tau_x \leq 25.6$ with 24.6 as the representative value. In the absence of any forcing function, $F_x$, x will have an approximately sinusoidal waveform with an amplitude of 1 (that is, the full excursion of x from a maximum of +1 to a minimum of −1 will be 2).

The forcing function, $F_x$, consists of two effects. The dominant effect is that of the light to which the retina is exposed. The secondary effect is due to endogenous internal influences of the activity-rest pattern.

We will consider the light effects first. A standard measure of the illuminance of the scene on which a human observer gazes is the foot-candle or the lux. This measure differs from the total light power on the visible spectrum since it is weighted by photopic luminosity function. That is, those portions of the visible spectrum to which the visual system is more sensitive are more heavily weighted. In formula 2, below, I denotes the illuminance of the scene of gaze (averaged over all of the directions of gaze encompassed by the retina). B denotes the subjective brightness which an observer associates with I. Stevens, *Science*, Vol. 133, pp. 80–86 (1961), has shown that over a wide range of I (about 6 log units), B is related to I by:

$$B = cI^{\frac{1}{3}} \quad (2)$$

where c is constant to be determined. The forcing function due to light actions on the retina is taken to be $$(F_x)_{light} = \frac{dB}{dt} = c\frac{d}{dt}(I^{1/3}) \quad (3)$$

This representation is a novel embodiment of two hypotheses: (1) subjectively assessed brightness is the appropriate measure of the effect of light on the circadian pacemaker, and (2) the x oscillator responds predominantly to changes of brightness and not, significantly, to sustained or average brightness.

The exponent, $\frac{1}{3}$, is substantially valid over a wide range of I. It is to be understood that exponents in a range about $\frac{1}{3}$ (such as $1/6$-$\frac{1}{2}$) are within the contemplation of the present invention, as are differing exponents for different ranges of I.

The coefficient c which is appropriate for normal human subjects when I is measured in lux is in the range $0.05 \leq c \leq 0.1$ with $c = 0.065$ as a representative value. The value for c is chosen on the basis of laboratory experiments conducted in ordinary room light in which entrainment occurred to an imposed period differing from $\tau_x$ by $\pm 1.0$-$1.3$ hours; and on the basis of the observation that blind subjects cannot entrain to periods which differ from $\tau_x$ by 0.4 hours. If the time history of light (including darkness, which is the absence of light) to which the retina is exposed is specified in lux, as I(t), then application of equation (3) gives the light-component of the forcing function, $F_x$, suitable for use in equation (1).

The endogenous, non-light forcing function onto the x oscillator is included in the model by an activity function A(t) which takes on the value O during sleep and a constant value $A_o$ during wakefulness. The activity forcing function is:

$$(F_x)_{activity} = \frac{dA}{dt} \quad (4)$$

Since A(t) takes on only two values, O or $A_o$, and the transitions between them take place relatively abruptly in time, the time derivative is singular at each transition and is represented mathematically as a "$\delta$-function." When the transition is from sleep to wakefulness, the $\delta$-function has the strength $A_o$; when the transition is from wakefulness to sleep the $\delta$-function has the strength $-A_o$. For normal human subjects $0.03 \leq A_o \leq 0.15$ with $A_o = 0.06$ as the representative value which is compatible with the entrainment data of blind subjects. In circumstances where sleep is associated with dark episodes, it is possible to infer A(t) from the temporal pattern of light and dark and so its effect on x becomes mingled with direct effects of light on x. Totally blind subjects display clearly the effects of A(t), since the direct effect of light is absent. Since in normal, sighted persons the effect of A is much smaller than ordinary environmental light effects, it is difficult to estimate this effect accurately.

With the descriptions given, a complete solution for x(t) can be generated computationally by an integration procedure such as the Runge-Kutta method from equation 1 if, at some initializing time, values for x and dx/dt are assigned and the subsequent temporal patterns of A(t) and B(t) are specified. The forcing function $F_x$ is represented as the sum of the two components:

$$F_x = (F_x)_{light} + (F_x)_{activity} \tag{5}$$

or $$F_x = \frac{dB}{dt} + \frac{dA}{dt}$$

Assuming that the light is within normal environmental ranges and that sleep episodes are regularly used, as time proceeds, the solution X(t) will depend progressively less and less on the specific initial conditions assigned.

6. Phase and Amplitude Modification Using Theoretical (Model-Based) Foundations a. Application of the Model to a Single Bright or Dark Episode

The objective in the application explained here is to make a quantitative assessment of the effects on the x oscillator of a specific intervention in which the light level is altered. For example, what would be the effect on a passenger during a flight of six hours' duration in which the average cabin illumination was maintained at 10,000 lux rather than the customary low level which is assumed to be 30 lux? According to equation (2), taking C to have the representative value of 0.065 we find the two B levels to be bright: $B = 0.065 * (10,000)^{\frac{1}{3}} = 1.40$
low: $B = 0.065 * (30)^{\frac{1}{3}} = 0.20$ Thus, for the six-hour flight B is increased by an amount delta $B = 1.20$. Since B is assumed to be essentially constant for the six hours, dB/dt is zero except at the beginning and end of the flight. At the beginning dB/dt has a δ-function of strength delta B and at the end dB/dt has a δ-function of strength −delta B. All other aspects of the subject's light and dark temporal pattern are presumed to be unchanged. The response of the differential equation (1) to a δ-function of strength delta B is to have an abrupt increase of $$\frac{12}{\pi} \frac{dx}{dt}$$

by an amount $$\frac{\pi}{12} \text{ delta } B$$

Let $t_1$ be the time in clock hours after the minimum of x at which the δ-function of strength delta B is applied, then $15t_1$ is the phase angle in degrees (after the minimum of x) at which it is applied. The abrupt increase in dx/dt will produce an abrupt change in the phase of x by an advance shift of $$\frac{\pi}{12} \text{ delta } B \cos(15t_1)$$

radians, assuming that the x oscillator is at its reference amplitude of unity. It will also produce a change of amplitude of amount $$\frac{\pi}{12} \text{ delta } B \sin(15t_1)$$

These are the phase and amplitude responses to elementary impulsive stimuli (abrupt change of light). If the negative δ-function is applied at time $t_2$ (after the minimum of x), it will produce an advance phase shift of $$-\frac{\pi}{12} \text{ delta } B \cos(15t_2)$$

radians and an amplitude change of $$-\frac{\pi}{12} \text{ delta } B \sin(15t_2)$$

The entire bright episode provides a change which is the sum of these two:
Phase advance (radians)=

$$\frac{\pi}{12} \text{ delta } B [\cos(15t_1) - \cos(15t_2)]$$

Amplitude change =

$$\frac{\pi}{12} \text{ delta } B[\sin(15t_1) - \sin(15t_2)] \tag{6}$$

Trigonometric identities permit them to be rewritten
Phase advance (radians)=

$$\frac{\pi}{12} 2 \text{ delta } B \left[ \sin \frac{15(t_2 + t_1)}{2} \sin \frac{15(t_2 - t_1)}{2} \right]$$

Amplitude change =

$$-\frac{\pi}{12} 2 \text{ delta } B \left[ \cos \frac{15(t_2 - t_1)}{2} \sin \frac{15(t_2 - t_1)}{2} \right] \tag{7}$$

These are the phase and amplitude responses for a bright episode of duration $t_2 - t_1$ centered at a time $(t_1 + t_2)/2$.

For the specific example of the six-hour plane flight, since $t_2 - t_1 = 6$ h, $\sin 15 (t_2 - t_1)/2 = \sin 45° = 0.707$, it follows that $$\text{phase advance} = \frac{\pi}{6} (1.20)(.707) \sin \frac{15(t_1 + t_2)}{2}$$
$$= .44 \sin \frac{15(t_1 + t_2)}{2} \text{ radians}$$
$$= 1.7 \sin \frac{15(t_1 + t_2)}{2} \text{ hours}$$

Suppose that this light episode is given to a person on an eastbound flight which leaves California at 0900 and arrives in New York at 1500 (California time). If the person is a typical young male adult with the minimum of x (as displayed by endogenous core body temperature) at 0600 California time, then $t_1 = 3$ h and $t_2 = 9$ h so $15(t_1 + t_2)/2 = 90°$ and the phase advance is seen to be 1.7 h. Thus, this acute light treatment will provide about 60% of the required phase advance from California to New York.

Suppose next that this exposure is given to a person flying westward from New York, departing New York at 1800 and arriving in California at 2400 (New York time). If this person's minimum of x is at 0600 (New York time), the typical value, then $t_1 = 12$ and $t_2 = 18$ so $15(t_1 + t_2)/2 = 225°$ and the phase shift is seen to be $-1.2$ h (actually a phase delay of 1.2 h), which is 40% of the delay required for the New York to California trip.

Both of these examples involve the increase of brightness during the episode. The formulae (7) can be applied equally well to situations where light is reduced, simply by allowing the change delta B to be negative. Thus, suppose that a subject is shielded from light (of say, 10,000 lux) to which he/she is ordinarily exposed and kept in a totally darkened room for 4 h:

bright: $B = 0.065 \times (10,000)^{\frac{1}{3}} = 1.40$
dark: $B = 0$

Then delta $B = -1.40$. Since $t_2 - t_1 = 4$ h, $\sin(15(t_2-t_1)/2 = 0.5$ and

Phase shift $= -1.40 \, (\pi/6) \, (0.5) \sin(15(t_1+t_2)/2)$ (radians)

If, as assumed before, the minimum of x is at 0600 and the dark episode is centered about 1200, $15(t_1+t_2)/2 = 90°$ and we have Phase shift = $-.37$ radians
$-1.4$h(1.4 h phase delay)

In summary, formulae (7) permit the calculation of phase and amplitude effects of any specific brightness intervention which is essentially constant over the duration of the intervention episode. It is necessary to specify both the imposed brightness and the brightness which it replaces in order to calculate the effects.

b. Application of the Model to Extended Multiple Exposure Light and Dark Protocols As the previous examples show, single episodes of reasonable brightness change lasting for reasonable durations can produce significant phase and amplitude changes, but less than are required for many common applications (for example, a 7 h phase advance from N.Y. to Paris, or an 8 h phase advance for a change of working shift). There is, therefore, a need for stronger effects and a need to program light and dark temporal patterns for extended time. To reduce somewhat the multitude of options, we will present the analysis for protocols which are cyclic with a 24 h cycle time. That is, we will consider the effects of light/dark temporal patterns which are specified for $0 \leq t \leq 24$ and repeated on a 24 h basis some integral number of times.

It was discovered that the strength of the phase-shifting drive is roughly proportional to the cube root of the illuminance, in lux. Thus, the earlier assumption by Lewy et al.—that any light of less than a 2,500-lux threshold could be equated with darkness for purposes of circadian analysis—appears to be incorrect.

This incorrect assumption was apparently related to a long-existing misconception that light was not a strong zeitgeber for the human circadian cycle. The effects of light much greater than the 2,500-lux threshold was not isolated in previous experiments which did not completely eliminate self-chosen light (100–300-lux) during periods of supposed "darkness" in the experimental procedures. The effect of applications of bright light was also masked by factors such as physical activity, posture, and timing of sleep episodes and feeding, in addition to the confounding influence of supposed "darkness" which was in fact not "dark", biologically.

It has been further discovered that it is not the bright lights, per se, that effectuate a phase modification. Rather, it is changes in light intensity that cause phase modifications. Although a 15-minute period of half illumination was used before and after "pulses" of bright light to acclimatize the subjects, it has been found that it is the change in light intensity, and not the bright light itself, which is the most direct causal factor in circadian phase shift. (In this discussion, the term "pulse" is not limited to a pulse of short duration; in fact, the duration of light pulses in the preferred embodiments of the present invention are on the order of three-six hours long. Conversely, DeCoursey determined that pulses with durations on the order of milliseconds had profound effects on flying squirrels living in otherwise total darkness.)

The first important observation is that an oscillator with low stiffness, such as $\mu_x = 0.1$, is a very effective band-pass filter. This means that it responds predominantly to excitation at or near its resonance period, $\tau_x$. This means that for forcing patterns which have a 24 h cycle it is the fundamental Fourier component (i.e., the component in the Fourier series expansion of the forcing pattern with a period of 24 h) which is principally responsible for secular (i.e., time-cumulative) shifts of phase and amplitude of x oscillation. Thus, different forcing patterns which have the same Fourier fundamental will have approximately the same cumulative effects on phase and amplitude. Different effects may be encountered for two forcing patterns with the same Fourier fundamental when the cumulative effectives per cycle are large (e.g., amplitude changes in excess of 0.6 or phase shifts in excess of 3 h per cycle).

To systematize the presentation and summary of the effects of cyclic protocols we introduce the concept of the "cyclic stimulus vector," or simply "stimulus vector." The magnitude of this vector is $\pi^2/12$ times the magnitude of the Fourier fundamental of the brightness pattern, B(t). The phase (or time of action) of this vector is the time at which the Fourier fundamental achieves its positive maximum value within the 24 h cyclic stimulus which we denote $t_m$. Then, if the cyclic pattern is initiated at some phase after the minimum of x, which we denote $t_p$, the phase of the stimulus vector after the minimum of x, $t_s$, is:

$$t_s = t_m + t_p$$

Thus, the effects of cyclic stimuli found by computational simulations will be classified according to
(1) The magnitude of the stimulus vector;
(2) The phase of the stimulus vector, $t_s$, for the first cycle of stimulus application; and
(3) The number of stimulus cycles, N.

These ideas are embodied in the example shown in FIGS. 33A, 33B, 33C, 34 and 35.

Figure 33A:
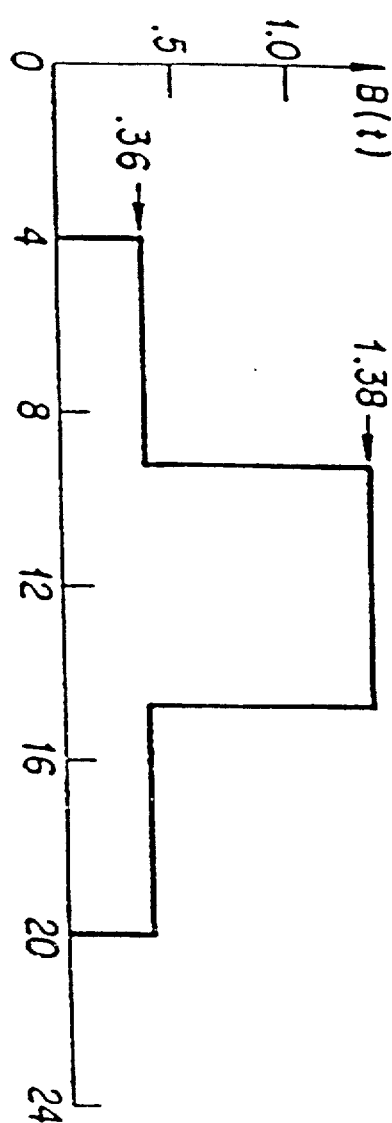
Figure 33B:
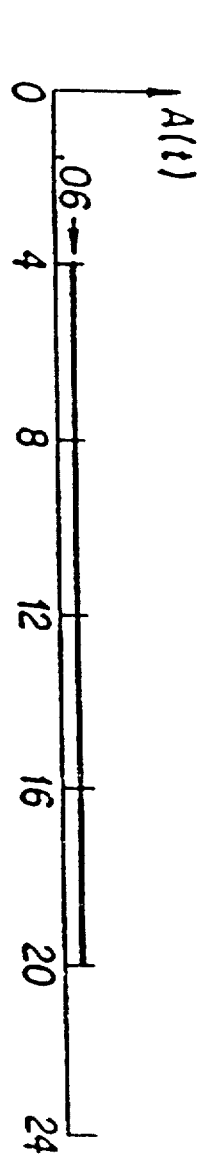
Figure 33C:
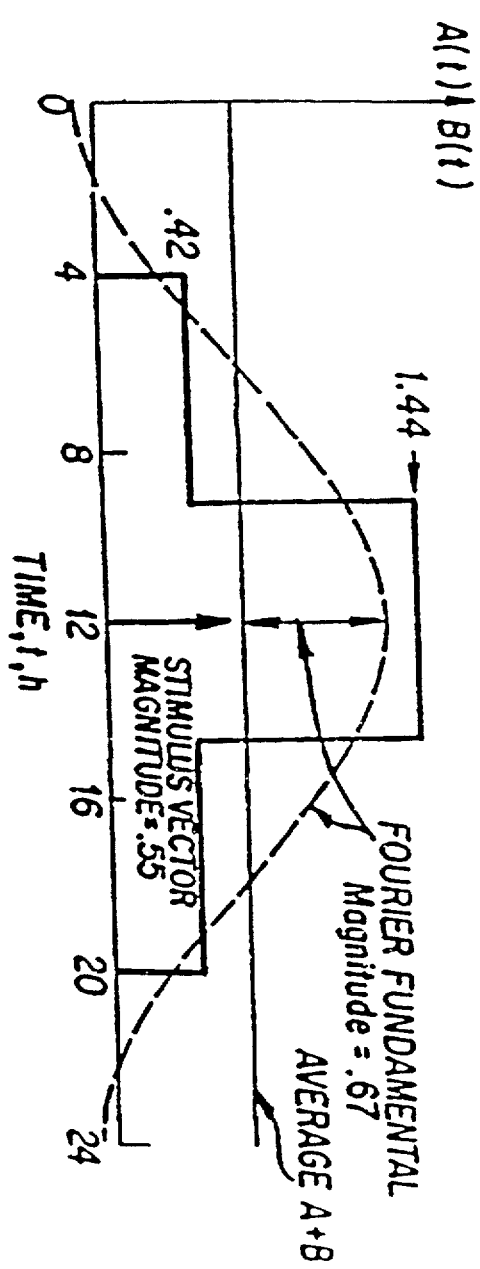

In FIGS. 33A, 33B and 33C a stimulus cycle is shown which contains both a dark episode of 8 h duration and a bright light episode (9,500 lux) of 5.5 h duration. Otherwise the brightness is equivalent to 175 lux of laboratory light. It is assumed that darkness corresponds to sleep and any light represents wakefulness so A(t) is known. The total stimulus is A(t)+B(t). Also in FIG. 33C the Fourier fundamental is shown and the corresponding stimulus vector, defined above. It is seen that $t_m = 12$ h and the stimulus vector magnitude is 0.55. Computer simulations have been performed using the representative period, $\tau_x = 24.6$ h, and locating the stimulus vector at various $t_s$. The standard amplitude of unity has been used as the initial value for x and the solutions have been started at the end of the dark episode. At the ends of succeeding dark episodes, N times 24 h later, the amplitudes and phases of the computed x are measured.

Figure 34:
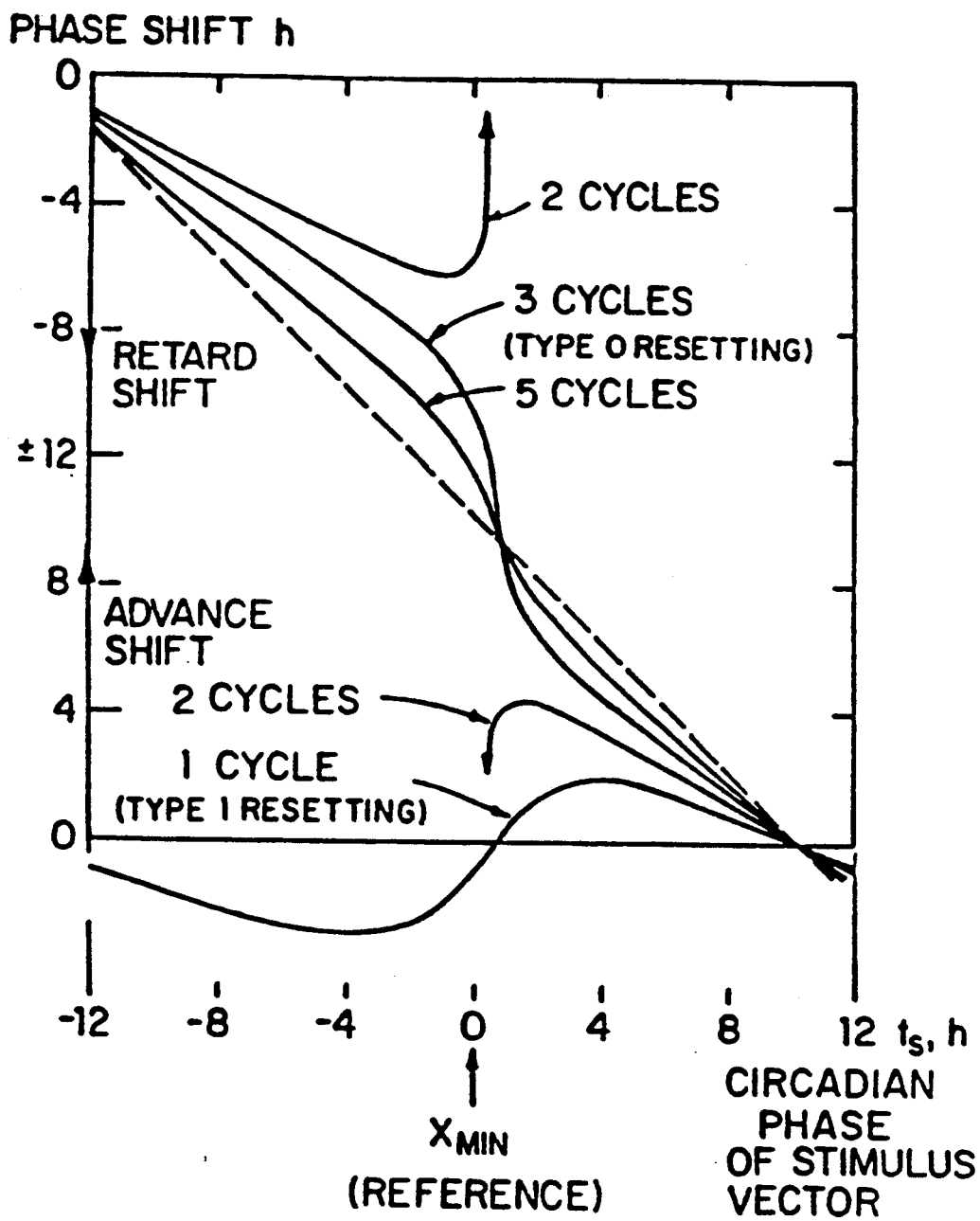
FIG. 34 shows a phase shift diagram, illustrating the two types of resetting curves which show resultant phase shift as a function of the phase of the stimulus vector.

The changes of phase from the initial x phase (in hours) are reported on the phase shift diagram of FIG. 34 for N=1, 2, 3, and 5. These are analogs of "phase response curves" (PRC) reported for other species, but whereas the conventional PRC are for briefly applied light stimuli, those of FIG. 34 are for extended light-/dark protocols. We observe that N=1 gives a PRC which is known as "Type 1 resetting" while N=3 and 5 give "Type 0 resetting." N=2 is very close to the borderline between these types but is in fact "Type 1".

Figure 35:
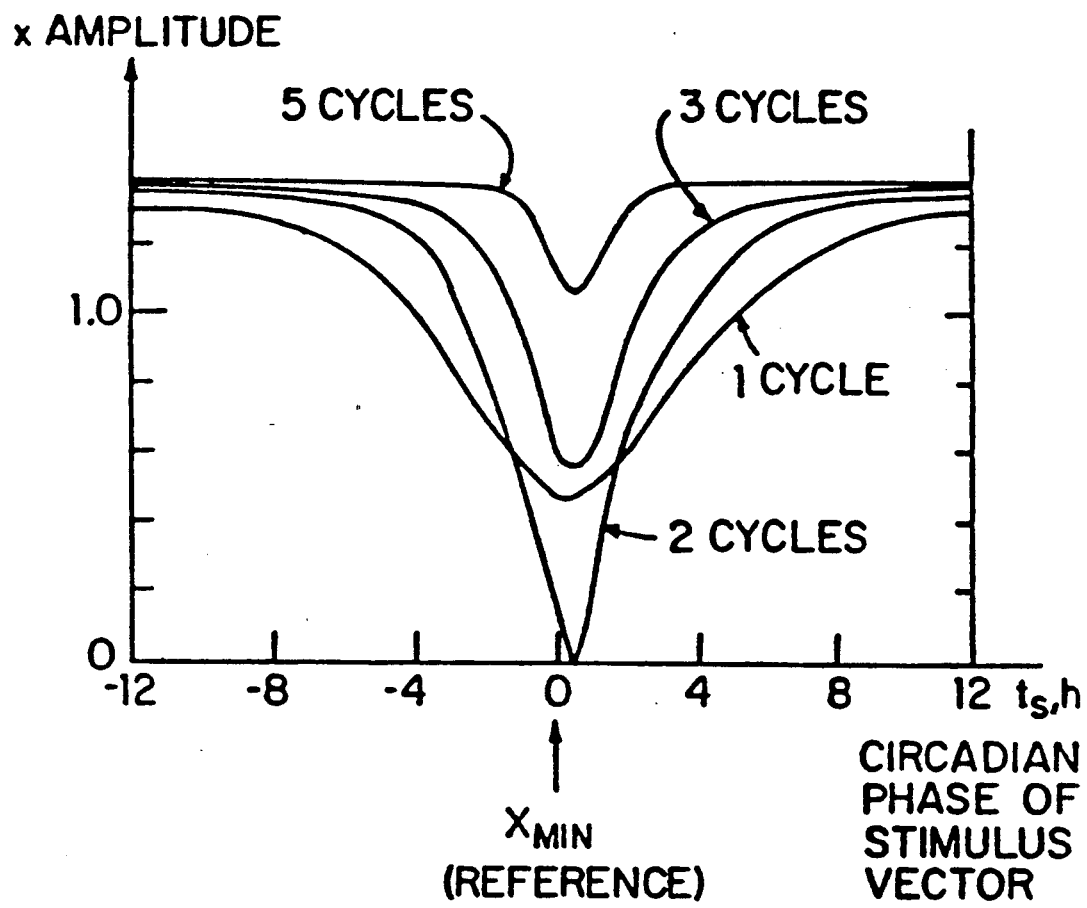
FIG. 35 shows amplitude response as a function of stimulus vector circadian phase for various numbers of 24-hour cycles.

FIG. 35 shows the amplitudes produced by the various N cycles and depicts amplitude response curves (ARC). It can be seen that the critical nature of N=2 (borderline between "Type 1" and "Type 0") is due to the reduction of amplitude virtually to zero. FIG. 34 shows that one cycle of this stimulus strength can produce at best 2 h of phase advance or 3 h of phase delay. (The asymmetry reflects the fact that x has a period, $\tau_x$, which is 0.6 h longer than the 24 h protocol. Similarly, 2 cycles can produce at best 4.2 h advance or 6.2 h delay (or 2.1 h and 3.1 h per cycle, respectively). In contrast, 3 stimulus cycles can produce any desired phase shift (up to 12 h advance or 12 h delay) because of the great reduction in the amplitude of the x oscillation on the intermediate cycles. Furthermore, after the full 3 stimulus cycles the amplitude is greatly restored, never being less than 60% of the original value and in many conditions being more than 35% larger than the original value.

Figure 36:
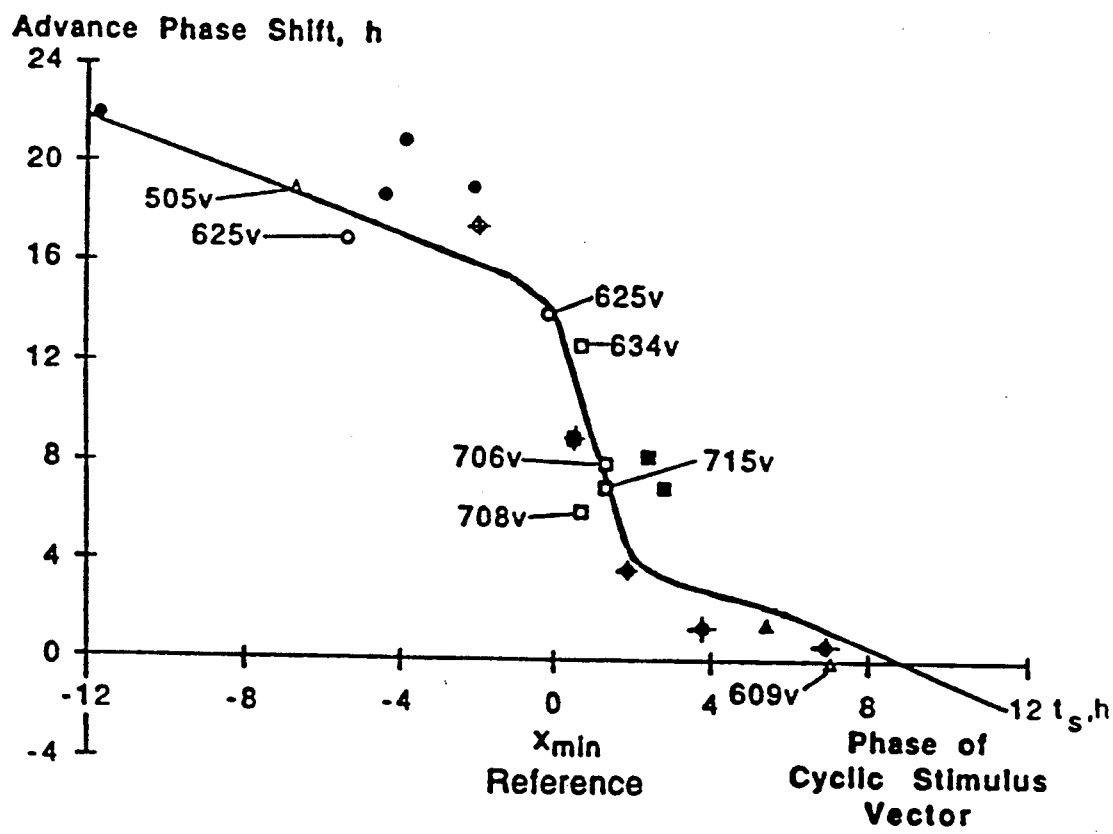
FIG. 36 shows the model's concordance with actual experimental data.

The experimental data derived from laboratory studies have been organized according to the phase of the cyclic stimulus vector being applied, as described just above, developed as part of this invention. As can be seen in FIG. 36, the comparison between the experimentally derived data and the model computations is quantitatively satisfactory. Symbols with crosses=Subject 713 V; filled symbols=Subject 618 V; open symbols=data for seven other subjects. Values for: $\square = 0.51 \leq$ Strength $\leq 0.56$; $0 = 0.35 \leq$ strength $\leq 0.50$; $\Delta = 0.27 \leq$ strength $\leq 0.34$. When organized in this manner, the experimental data themselves become internally consistent, thereby resolving the ambiguity and multivaluedness of the data as presented either in the classical phase response curve (PRC) to light, organized by the circadian phase of light administration, shown in FIG. 11 or in the newly recognized organization of the data based on the phase of dark episode timing, as in FIG. 14. Neither the representation of FIG. 11 nor that of FIG. 14 simultaneously take into account the phase of both light exposure time and dark exposure time, which is accomplished in the cyclic stimulus vector diagram of FIG. 36.

c. Stopping the x Oscillation

From the ARC (Amplitude Response Curve) of FIG. 35 we find that two cycles of a strong cyclic stimulus can reduce the amplitude of the x oscillation to extremely low values. At an amplitude of zero the circadian clock can be said to have been "stopped."

To be of use in studies of the effects of this unusual condition it is necessary to bring a subject precisely to this state under appropriate laboratory or environmental conditions. Typically this means that zero amplitude should be achieved upon a wake-up into the desired environment. If we suppose that we have some approximation to a protocol which might bring a subject from an experimentally-determined initial state (the amplitude and reference phase of x having been deduced from the core body temperature of a Constant Routine, for example) it is not a straightforward or simple matter to modify the protocol to suit a specific subject. The difficulty is that the zero-amplitude or "stopped clock" condition is, mathematically speaking, a "small target" and for the differential equation (1) which describes the x oscillator and the natural tendency of solutions is to move away from that condition. (That is, the zero-amplitude condition is an unstable singular point.)

Consequently the protocol must be "fine-tuned" to the specific subject and his/her initial state. Ideally the subject's intrinsic period, $\tau_x$, should first have been measured experimentally (as, for example, through internal desynchrony forced by placing the subject on a sleep/wake cycle of 28 h period). Then the differential equation, together with the candidate approximate protocol, should be integrated backwards in time, beginning at zero amplitude (which is the desired end state). If the candidate protocol does in fact have a usable solution, the solution for x will have an amplitude which grows (backwards in time) until it passes through the amplitude which has been ascribed to the subject's initial state. The point in this reversed-time solution which exactly matches the subject's amplitude is now the onset point for the protocol and the timing of all events in the protocol is given by returning to "forward time." Furthermore, the phase of x at this precise solution point establishes the relationship between the time at which the protocol commences and the time of the minimum of x.

Clearly there are many clock-stopping protocols which can be developed using this model. Cyclic protocols are usually required and those which involve a strong stimulus vector will achieve zero-amplitude in fewer clock hours. This is especially desirable if the subject's $\tau_x$ is not accurately known (as, for example, it is estimated on the basis of normative data relating to the subject's age and sex), since errors in $\tau_x$ produce cumulative phase errors during any protocol in direct proportion to protocol duration. Protocols which attain the initializing amplitude during a sleep episode may have to be rejected if the fraction of the sleep episode which remains within the protocol is judged to be too short to serve the appropriate sleep function. This condition can generally be eliminated by altering the strength of the stimulus vector (by changing the duration of bright episodes, for example).

What follows is a description of a particular protocol for manipulation of the amplitude of the endogenous (deep) circadian pacemaker.

Figure 37:
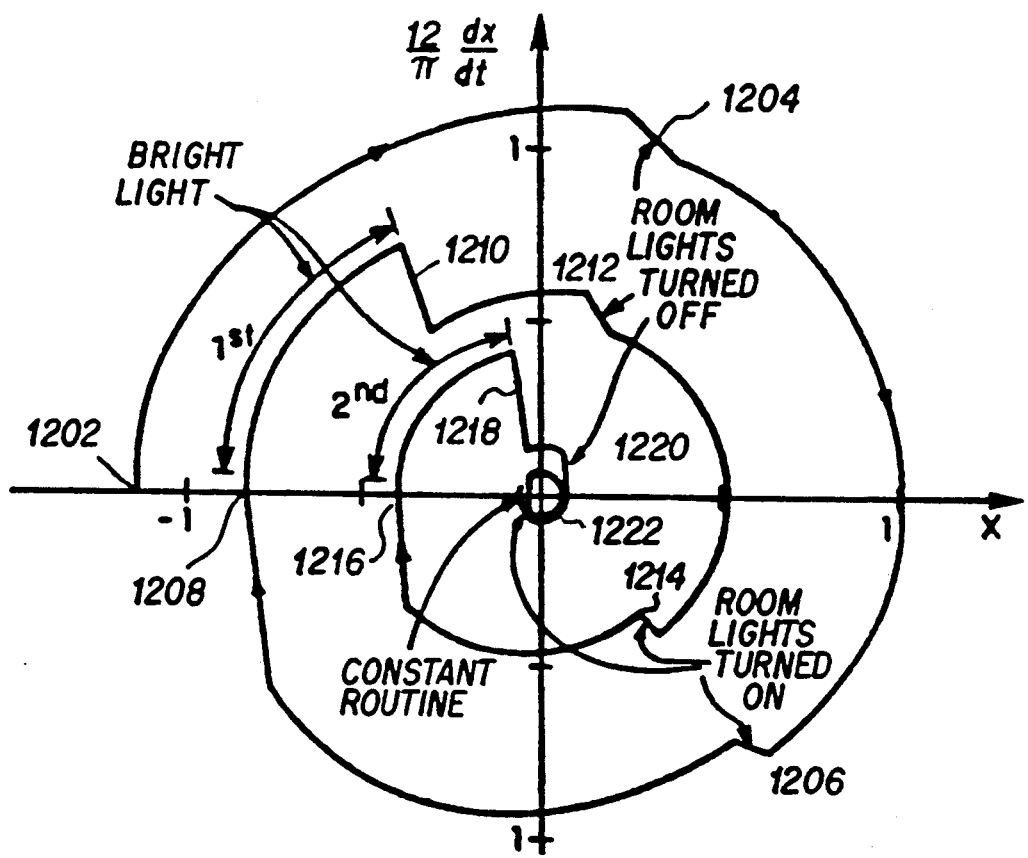
FIG. 37 is a phase-plane diagram illustrating the use of bright light pulses to reduce the amplitude of the endogenous circadian pacemaker to near the mathematical "singular point".
Figure 38:
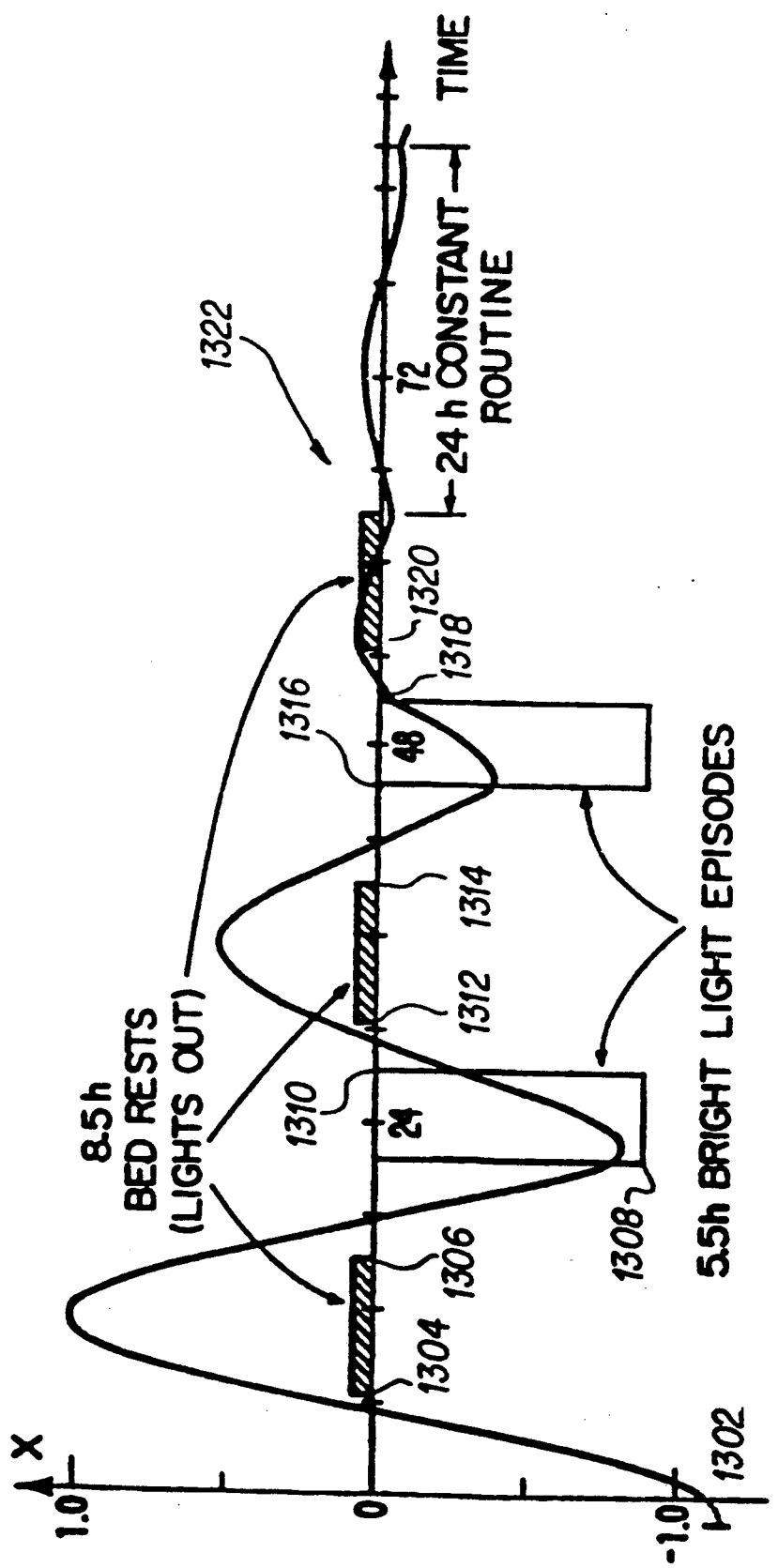
FIG. 38 is a timing diagram corresponding to the phase-plane diagram of FIG. 37.

FIGS. 37 and 38 illustrate a phase plane diagram and a timing diagram, respectively, of the phase and idealized core body temperature of a subject whose deep circadian pacemaker amplitude is being reduced to near zero.

This idealized experiment begins with the endogenous circadian pacemaker at a minimum at 1202/1302. Between times 1204/1304 and 1206/1306, the subject rested or slept, in darkness. After a period of ordinary diurnal activity, the subject was then exposed to bright light from time 1208/1308 until 1210/1310. As indicated at 1210, the bright light episode has substantially reduced the amplitude of the endogenous circadian pacemaker.

A succession of diurnal activity, bedrest, diurnal activity, and another bright light episode is repeated at times delimited by 1212/1312, 1214/1314, 1216/1316, and 1218/1318. A significant reduction in amplitude of the endogenous circadian pacemaker is indicated at 1218. After one more period of diurnal activity and another episode of bedrest in darkness, the subject entered a Constant Routine for 24 hours. By this time, the amplitude of the endogenous circadian pacemaker had been reduced by the previous bright light episodes. The amplitude of the endogenous circadian pacemaker has effectively been reduced to zero.

The application of a bright light pulse at any point after the amplitude is zero results in the instant resetting of the deep circadian pacemaker to a newly defined phase. The virtual instantaneousness of this phase resetting represents the extreme demonstrated by the difference of the phase traversals already indicated in FIG. 37. Specifically, it is evident that the phase shift during the second bright light episode 1216 to 1218 is greater than the phase shift during the first bright light episode 1208 to 1210. This enhancement of the phase shift is based on a reduction in the endogenous circadian pacemaker amplitude. When the amplitude is reduced in the extreme, that is, to an amplitude zero, any desired phase shift may be achieved in a diminishingly small period of time.

FIG. 31 illustrates the actual measured core body temperature of a human subject as a function of time in an actual experiment utilizing the principles of the present invention. The subject underwent Constant Routines beginning at times indicated by 1402 and 1408. Between these two Constant Routines, however, two bright light episodes, indicated as 1404 and 1406, were imposed.

An amplitude reduction to near zero is shown at 1410, after the commencement of the second Constant Routine. After time 1410, the peak-to-peak amplitude of the endogenous circadian pacemaker, as measured by the fitted core body temperature variation, was reduced from 2°-3° F. to a level below detection.

7. Devices for Facilitating the Method a. Devices for the Administration of Light

Use of the methods of the invention requires that a person or group of persons may be exposed to light of the necessary intensity at the necessary time(s). The invention envisions many methods for illuminating an environment which can be adapted to this purpose. In particular, electric lights of either incandescent or fluorescent type can produce light of sufficient intensity when large numbers of them are concentrated on a surface. A wall eight feet high and ten feet wide covered with conventional fluorescent lamps spaced two to three inches apart (3800-5800 watts total) will create illumination sufficient to expose a person to 9,500 lux at a distance of ten feet or so, if the person's gaze is directed at the wall. Fluorescent lamps have the advantage that they emit light over their entire surface rather than at a single bright spot. Thus the light is diffuse enough that a person can stare directly at the glowing lamp from any distance without discomfort (although a person coming directly from a dark environment would require a adjustment period of partial illumination to allow the eyes to adjust). A similar wall bearing an array of incandescent lamps is also effective, but the intensity of light at the lamps' filaments may make it necessary to place a diffuser between the lamps and the viewer. The diffuser must be of heat-resistant material and the brightness of the lamps must be increased to compensate for the overall intensity and spectral loss of light caused by the diffuser.

If the lights are placed on the ceiling or an overhead flat surface, then the illumination of the user's eye is by light reflected from the surroundings rather than by light directly from the lamp (unless the user is in a supine or reclining position looking upward, in which case the situation is the same as with the lights mounted on a wall). Thus, the light must be brighter at the source to compensate for its absorption by surfaces and objects in the environment. However, since the user would not be gazing directly at the overhead light, sources with greater intensity can be used, such as high-intensity incandescent lamps, halogen lamps, arc lamps, mercury or sodium vapor lamps, or the sun. Use of natural sunlight via skylights or outdoor atria is precluded in most but not all cases because it is available only at certain hours and is subject to variation caused by season and weather.

Large banks of lights require large amounts of space and consume a great deal of energy. The cost of the space and the light fixtures may be too high for most individual users but can be offset if multiple users are expected, for example, in a public facility, factory or airplane. The energy used to power the lights—which is ultimately converted into heat—may be recycled by circulating the air heated by the fixtures and in the illuminated area and using it for heating purposes elsewhere. Many such installations would operate primarily in the winter when short daylight hours and cold outdoor temperatures limit the availability of sunlight, so the heat produced is of value. Ideally, the parts of the light installation creating the most waste heat such as the lamps, ballasts, and dimmers, are enclosed and ventilated separately from the surrounding area; the heated air exhausted from the enclosure is handled by ducts and blowers incorporated into the environmental conditioning system of the building.

Figure 39C:
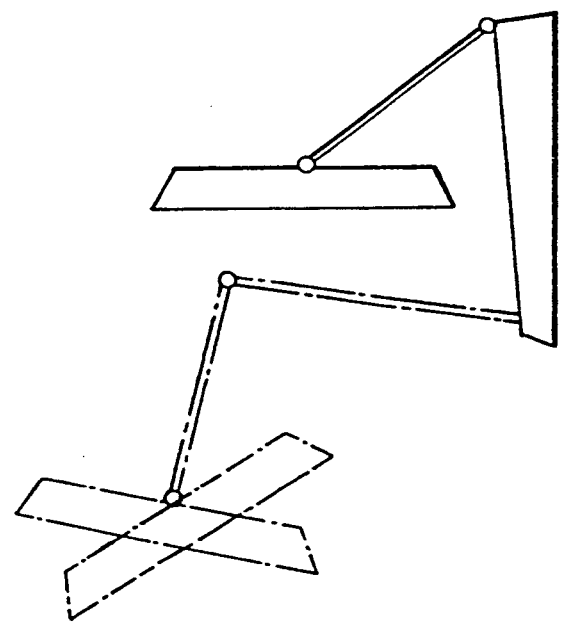
FIG. 39c illustrates the representative lighting appliance having a flexible stand.
Figure 39A:
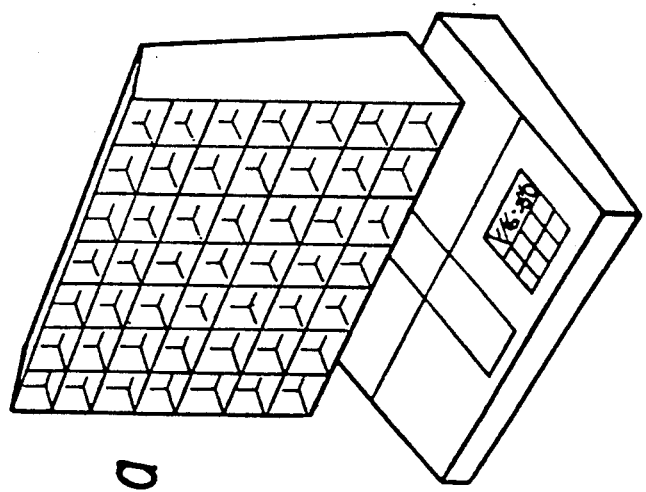
FIG. 39a illustrates a representative lighting appliance.
Figure 39B:
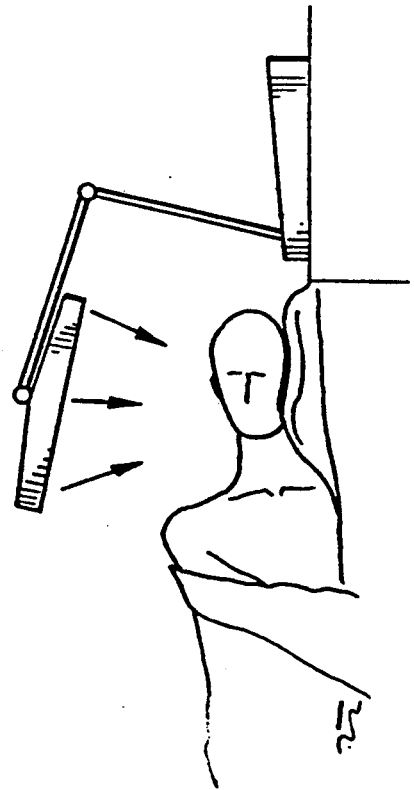
FIG. 39b shows the representative lighting appliance applied to a subject.

An alternative to large light banks are smaller lights placed closer to the user (FIGS. 39a, 39b, and 39c). A bank of ten four-foot fluorescent lamps covering a three-foot by four-foot area and positioned vertically produces illumination of 9,500 lux at a distance of about 3 feet from the eye, if the user's gaze is toward the lamps. Halving the distance between the lights and the user allows halving each dimension of the array and quartering the total light output while producing the same amount of light incident to the user's eye. Thus, a light fixture two feet wide and eighteen inches high suffices if it remains approximately eighteen inches from the user's face. Such a fixture is easily portable and can be mounted on a flexible positioning stand that would allow the user to place it at the ideal height, tilt, and distance. Such a fixture makes an ideal device for persons who must use the lights chronically. It may also be desirable to have such a device for home use. For example, morning exposure to bright light could both greatly improve daytime job performance and enhance nighttime sleep by amplifying circadian amplitude, which reinforces stable entrainment. The limitations in the user's movements caused by the closeness of the lights, and the boredom of having to gaze in a single direction, can be offset by leaving the spaces between the lamps open, thus permitting the user to focus his or her eyes on a television (or the like) placed a distance behind the fixture.

Another possibility is the use of localized retinal illumination through illuminated goggles (FIGS. 40a and 40b). The goggles provide a bright field of light, produced by small lamps within the goggles themselves, leaving a slit or other opening in the center through which the wearer can see. The light thus provided is fully portable, requires very little energy, and is easily controlled. The physical position of the goggles determines the precise distance from the lights to the eyes, making control of the illumination level very precise. Variations in light from the environment entering the openings can be compensated for by an electronic device incorporating a photodiode or phototransistor that senses the ambient light level and dims or brightens the goggles' internal lights accordingly.

While the use of localized retinal illumination through light-controlled goggles is appealing from the standpoints of portability, low energy requirement, precise timing, uniform controllability, and the mobility they afford the wearer, there are several considerations to be addressed. First, light scattering in the vitreous humor (due to the Tyndall effect) will add light to the fovea and parafovea, which may limit the usable brightness applied to the periphery by obscuring the image from the environment that we wish to preserve on the fovea. Furthermore, the peripheral retina serves an important function in alerting a person to moving objects, thereby warning of dangers, etc. This may limit the use to relatively quiet, safe environments. Also, the psychological effects of viewing the world through a restricted opening in a bright field may not be acceptable. The converse situation in which the surround is dark we expect will be very tolerable, perhaps even pleasant. We note that Eskimos have long used devices with horizontal slit-shaped apertures to shield most of the retina from snow glare. Apparently the wearer can function quite normally with this restructure of field of view. It is possible that the slit aperture may permit normal freedom of movement in the case of the bright periphery as well.

Additionally, the development of instrumentation to measure light exposure would facilitate the implementation of the preferred embodiments. For example, a light meter could be developed which would measure brightness as given by $B=0.065I^{\frac{1}{3}}$ above. The ability of such a meter to integrate light exposure over an entire day would greatly facilitate the calculation of a phased stimulus vector and could allow individuals to more closely monitor their effective dose of light.

b. Devices for the Administration of Darkness

Use of some of the methods of the invention requires that individuals be shielded from light or exposed only to attenuated light. A person may be shielded from incident light by placing him or her in a dark windowless room or by placing an opaque material over his or her eyes.

As an alternative to constructing a windowless room, the windows of a normal room such as a hospital room, hotel room, or private bedroom can be modified by covering all windows with shutters or shades designed to totally exclude light. Many such devices are used for photographic darkrooms and are highly effective. One type uses an opaque screen that slides in a frame running completely around the window opening. Black velvet-like surfaces seal out light all the way around the frame when the screen is closed. The screen opens by sliding upward in the frame and rolling up at the top, which allows normal use of the window. For short-term use, a simple "blackout curtain" of flexible opaque material, covering the window and adhered around the edges is also effective.

Some circumstances require that a person be shielded from bright light while active and able to see. Devices for reducing the light coming into a person's eye, while still permitting vision, are needed. Goggles and masks that uniformly attenuate all incident light are commonly used as safety devices by welders and other workers whose work exposes them to hazardously bright light. These same devices may be applied to the methods here when light attenuation is needed. The device must block light from all directions with opaque material or a material of a low transmissivity of approximately one to ten percent.

Another device serving a similar function has long been used by Eskimos to protect from snow glare. It has the form of an opaque eye or face covering with a horizontal slit-shaped aperture. The aperture admits sufficient light and a sufficient view area to allow normal movement while surrounding most of the eye with a dark field.

Advantageously, the light admitted by a light attenuating device may vary according to ambient conditions, blocking the light more completely in bright light or daylight and admitting more light when the surroundings are dark. This characteristic makes such a device safer and more effective, and it can be achieved in a variety of ways. Photochemically sensitive coatings exist that darken when exposed to brighter light; they are commonly used in sunglasses. Such a coating, but with a generally greater saturation level, would be applicable, or existing coatings can be used in conjunction with a conventional light attenuating filter.

More precise control is afforded by the use of an electronic device built into the goggles that senses the ambient light level and compensates accordingly, by mechanically widening or narrowing the viewing aperture with a small motor, or by rotating one polarized filter element relative to another to change the transmissivity, or by activating a translucent material or coating that changes its transmissivity in response to a small voltage placed across it.

c. Devices for the Scheduling and Timing of Therapeutic Light and Darkness

The methods and formulae described for determining the ideal scheduling of periods of light and darkness to achieve a desired phase or amplitude change for a given individual can be put into effect in a variety of ways. A physician or other person trained in the method can make the determination for an individual; this is appropriate in cases where the change is to be effected for therapeutic reasons such as the treatment of affective personality disorders or the treatment of delayed sleep phase insomnia. However, other applications of the technique, such as treatment of jet lag or to facilitate adaptation to shift change transitions for workers, may benefit from devices that automate or simplify the calculation of light and darkness schedules based on the formulae of the mathematical model developed herein.

A computer program can be created for any given computer device that performs the relevant calculations. The program queries the user about his or her sleep characteristics and the nature of the change desired. The program allows the user to express this information in nontechnical language—for example, in the case of jet lag amelioration, it would ask the origin and destination locations and the times of the airline flights;

the user would not need to know the longitudes of the locations or any of the principles behind the method. The program would inform the user what times to schedule light and darkness.

For general users such as frequent business travelers, the program can be made to run on personal or business computers, and can be sold and distributed in a variety of media including magnetic disks, magnetic tapes, optical disks, direct loading via modem, printed code strips, paper tapes, and source code listings on paper. For larger-scale users such as airlines, the program incorporating the method can itself be incorporated into existing multipurpose computer systems. In the case of airlines, such a subsystem can dispense recommended light and darkness schedules for jet lag reduction along with other flight information.

The method can also be incorporated into small dedicated devices such as "smart" wristwatches or calculators, ideal for frequent travelers or shift workers. A slide rule device, either linear or circular, can be created that allows the user to determine a schedule by setting parameters and reading results from sliding analog scales. A coin-operated electronic device that queries the user and dispenses the information for a fee can be placed in public places, particularly in airports.

Timing and scheduling mechanisms can also be built into the light fixtures and installations themselves. These devices would determine the proper times and automatically turn the lights on when appropriate. This is particularly effective where lights are installed in workplaces (for shift change adjustment) or in airport waiting areas and aircraft (for jet lag compensation) since they would operate on programmed schedules without human intervention.

d. Installations Incorporating the Devices

There are many ways that the methods and devices described herein can be implemented to provide a service to those that would benefit from them. Hospitals, factories, and utilities which operate around the clock can install overhead fixtures with sufficient lighting capacities to effect the method. Computers programmed with the operation's shift schedules could operate the lights routinely and automatically for the benefit of workers.

Hospitals and medical facilities providing care to persons with affective disorders or sleep scheduling disorders can equip certain rooms with opaque window screens and banks of wall or ceiling mounted lights to allow the patient to be exposed to light and/or darkness as required for their treatment. These rooms can also be equipped with the necessary apparatus for carrying out the phase-assessment diagnostic procedure before and/or after therapy. Patients can use home appliances for exposure to lights at specific times of day as ordered by a physician. Light and/or darkness goggles can also be used to augment this treatment. Hotels catering to international air travelers can install bright lights in bedrooms or in a central facility, and darkness curtains in bedrooms, thus creating a special service to customers likely to suffer from jet lag. A computer, coin operated or operated by hotel desk personnel, will dispense information to individual guests on the best times of exposure. A dedicated 'salon' operating independently from hotels could also provide this service in the same way that ultraviolet tanning salons operate today. Airports and airlines can install equipment allowing them to offer a special class of service providing facilities for passengers to be exposed to amplified or reduced lighting to aid in their adaptation to new time zones. This equipment can include bright lights installed in special airport lounges or in the aircraft themselves.

Frequent travelers may be willing to purchase personal portable equipment such as light/darkness goggles and exposure time calculators to facilitate their own adjustment to shifting time zones. Military and aerospace facilities and vehicles can utilize equipment similar to that described for civilian airports and aircraft, in order to help critical personnel adapt to shifting operational schedules or transmeridian travel without loss of performance.

Spacecraft, submarines, machine rooms, isolated research environments, hospital intensive care areas, and all other environments where people must live and work while isolated from the external environment can utilize schedules of bright and subdued light, designed in accordance with the methods herein, to improve the health and the sleep hygiene of their occupants.

As stated above, there are several potential uses of this invention, namely to help shift workers adapt to variable work schedules, reduce jet lag, and treat patients with a variety of medical disorders. Specifically, factories, hospitals and utilities which operate around the clock could install overhead fixtures with sufficient lighting capacity to employ this new process to facilitate adaptation of the workers to their persistently changing work schedules. In wintertime, the indoor lights could be used to provide heat for the facilities.

In addition, the process could be used by several components of the travel industry. With development of proper hardware, international air carriers could initiate a special class of service providing facilities for passengers to be exposed to amplified or reduced lighting at times designed to aid in their adaptation to their destination time zone. Airport and other hotels catering to the international business traveler could have sunlight simulator suites where guests could be exposed to lights prior to or after a trip. Finally, with appropriate miniaturization, it may be possible for consumers to purchase "sunglasses" which would actually emit light such that the retina would be exposed to the intensity of light required to achieve the desired effect.

Patients with medical disorders could use home appliances for exposure to the lights at a specific time of day. This could be conducted in conjunction with a diagnostic procedure before and/or after the administration of the phototherapy. Patients likely to benefit would include those with delayed, advanced, or hyper-nycthemeral sleep syndromes, and potentially patients with psychiatric disorders.

8. Conclusion

Whereas various particular embodiments of the present invention have been disclosed in detail above, it is to be understood that they are presented by way of example, and not limitation. Thus, the full scope and import of the present invention should not be limited by any of the embodiments described above, but should be defined only in accordance with the following claims.

What is claimed is:

1. A method of modifying a subject's endogenous circadian cycle to a desired state, comprising the steps of:
    assessing predefined specific characteristics of a present endogenous circadian cycle of the subject;

selecting one or more appropriate times in the present endogenous circadian cycle, based on the assessed characteristics, at which to apply a stimulus to effect a desired modification of said cycle;

applying said stimulus, comprised of a pulse of bright light, at each of said selected appropriate times in said present endogenous circadian cycle, to effect the desired modification of said cycle;

whereby the characteristics of the present endogenous circadian cycle of the subject are rapidly modified to substantially reduce the amplitude of the subject's endogenous circadian cycle and applying a single pulse of bright light, after said applying step has modified the amplitude so that the amplitude is substantially reduced with respect to the present circadian cycle, to set the endogenous circadian cycle to a desired phase.

2. The method of claim 1, wherein said first applying step further comprises:

applying, at preselected times in said assessed present endogenous circadian cycle, episodes of imposed strict darkness of preselected duration.

3. The method of claim 2, wherein said assessing step comprises:

assessing the phase of the present endogenous circadian cycle of the subject.

4. The method of claim 2, wherein said assessing step comprises:

assessing the amplitude of the present endogenous circadian cycle if the subject.

5. The method of claim 2, wherein said assessing step comprises:

assessing the phase and the amplitude of the present endogenous circadian cycle of the subject.

6. The method of claim 2, wherein said first applying step comprises:

applying pulses of light in the range of 7,000–12,000 lux.

7. The method of claim 6, wherein said first applying step comprises:

applying pulses of light of approximately 9,500 lux.

8. The method of claim 2, wherein said assessing step comprises:

placing the subject in a semi-recumbent position;
minimizing the subject's physical activity;
feeding the subject small amounts of food at regular, closely-timed intervals;
keeping the subject awake;
measuring the characteristics of the present endogenous circadian cycle by measuring physiological parameters of the subject; and
forming a representation of the physiological parameters as a function of time.

9. The method of claim 8, wherein said measuring step comprises:

measuring one or more of core body temperature, cortisol secretion, and other endocrine functions.

10. The method of claim 2, wherein said assessing step comprises:

using normative data to estimate the characteristics of the present endogenous circadian cycle of the subject.

11. A method of modifying a subject's endogenous circadian cycle to a desired state, comprising the steps of:

assessing predefined specific characteristics of a present endogenous circadian cycle of the subject;

selecting one or more appropriate times in the present endogenous circadian cycle, based on the assessed characteristics, at which to apply a stimulus to effect a desired modification of said cycle; and applying said stimulus, at certain ones of said selected appropriate times in said assessed present endogenous circadian cycle, to effect the desired modification of said cycle, said stimulus comprised of a pulse of bright light, and, optionally, an episode of imposed strict darkness, so as to modify the amplitude of the endogenous circadian cycle to be substantially reduced with respect to the present circadian cycle; and applying a subsequent stimulus comprised of a pulse bright light or an episode of imposed strict darkness at another one of said selected appropriate times to set the endogenous circadian cycle of the subject to the desired state.

12. The method of claim 11, wherein said selecting step further comprises the step of:

selecting a duration of said stimulus based on the assessed characteristics.

13. The method of claim 11, wherein the steps of applying comprises applying said stimulus to the subject's retinas.

14. A method of assessing modification capacity of a stimulus on a subject's endogenous circadian cycles, comprising the steps of:

assessing predefined specific characteristics of a prestimulus endogenous circadian cycle of the subject;

selecting one or more appropriate times in the prestimulus endogenous circadian cycle, based on the assessed characteristics, at which to apply a stimulus;

applying pulses of bright light and optionally episodes of imposed strict darkness to the subject at the selected appropriate times so as to modify the amplitude of the prestimulus endogenous circadian cycle of the subject to a desired state; and assessing predefined specific characteristics of a poststimulus endogenous circadian cycle of the subject;

wherein said assessing steps comprise:
placing the subject in a semi-recumbent position;
minimizing the subject's physical activity;
feeding the subject small amounts of food at regular, closely-timed intervals;
keeping the subject awake; and
measuring the characteristics of the endogenous circadian cycles by measuring physiological parameters of the subject.

15. The method of claim 14, wherein said measuring step comprises:

measuring one or both of core body temperature and cortisol secretion.

16. The method of claim 14, wherein said assessing steps comprise:

measuring the phase of the endogenous circadian cycles of the subject.

17. The method of claim 14, wherein said assessing steps comprise:

measuring the amplitude of the endogenous circadian cycles of the subject.

18. The method of claim 14, wherein said assessing steps comprise:

measuring the phase and the amplitude of the endogenous circadian cycles of the subject.

19. The method of claim 14, wherein said applying step further comprises:

applying pulses of light in the range of 7,000-12,000 lux.

20. The method of claim 14, wherein said applying step further comprises:
applying pulses of light of approximately 9,500 lux.

21. The method of claim 14, further comprising the steps of:
compensating for an endogenous circadian cycle having a period not equal to 24 hours.

22. A method of shifting the phase of a subject's endogenous circadian cycle to a desired phase comprising the steps of:
(a) determining a subject's endogenous circadian cycle;
(b) modifying the amplitude of the subject's endogenous circadian cycle;
(c) selecting a time at which to apply a stimulus in order to effect the desired shift in the phase of said cycle;
(d) applying said stimulus, comprised of bright light, at the time selected to shift the phase of the subject's endogenous circadian cycle.

23. The method of claim 22, further comprising:
(e) repeating steps (c) and (d) one or more times according to the subject's determined endogenous circadian cycle until the desired phase shift is achieved.

24. The method of claim 22, wherein step (b) further comprises:
reducing the amplitude of the subject'endogenous circadian cycle.

25. A method of changing the amplitude of a subject's endogenous circadian cycle comprising the steps of:
(a) determining a subject'endogenous circadian cycle;
(b) selecting, based on said determining step, a time at which to apply a stimulus in order to effect a desired change in the amplitude of said cycle;
(c) applying said stimulus, comprised of bright light, at the time selected, to change the amplitude of the subject's endogenous circadian cycle.

26. The method of claim 25, further comprising:
(d) repeating steps (b) and (c) one or more times according to the subject's determined endogenous circadian cycle until the desired amplitude change is achieved.

* * * * *

UNITED STATES PATENT AND TRADEMARK OFFICE
CERTIFICATE OF CORRECTION

PATENT NO. : 5,163,426

DATED : November 17, 1992

INVENTOR(S) : Czeisler et al

Page 1 of 5

It is certified that error appears in the above-indentified patent and that said Letters Patent is hereby corrected as shown below: On the title page: Item

[75] Inventors, after "Allan," delete "Pittsburgh, Pa." and substitute --Boston, Mass.-- therefor.

Column 51, line 7, delete "steps" and substitute --step-- therefor.

Column 52, line 7, delete "subject'" and substitute --subject's-- therefor;

line 11, delete "subject'" and substitute --subject's-- therefor.

In the drawings, delete Figures 2, 9, 13 and 33 and substitute therefor Figures 2A, 2B, 9a, 9b, 13a, 13b, 33A, 33B, and 33C attached hereto.

Signed and Sealed this

Twenty-sixth Day of October, 1993

Attest:

BRUCE LEHMAN

*Attesting Officer*

*Commissioner of Patents and Trademarks*

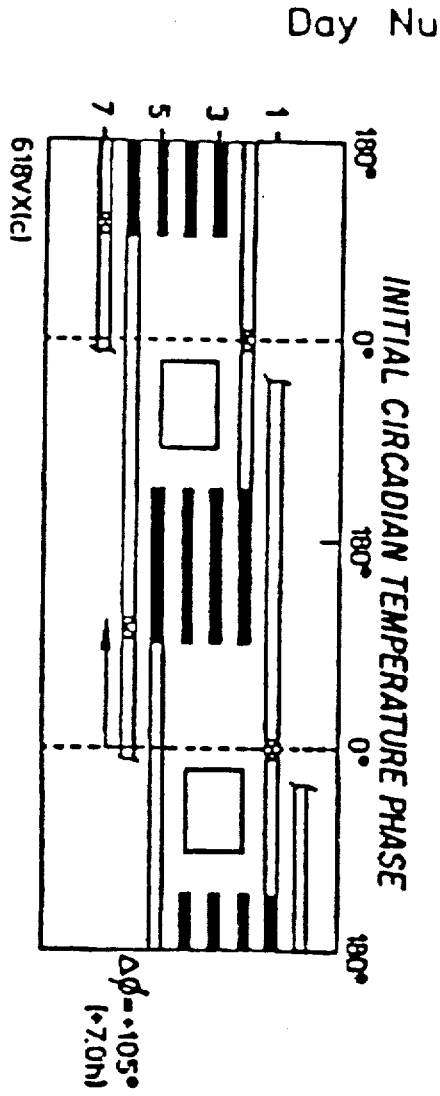
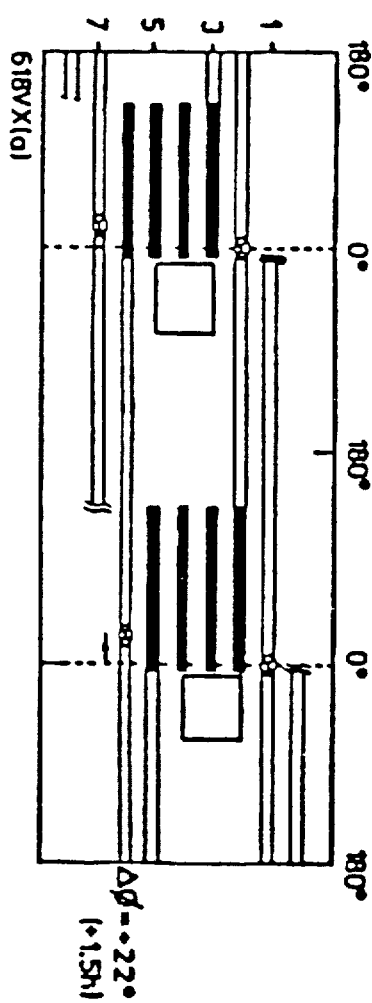
FIG. 13a
FIG. 13b

UNITED STATES PATENT AND TRADEMARK OFFICE
CERTIFICATE OF CORRECTION

PATENT NO. : 5,163,426

DATED : November 17, 1992

INVENTOR(S) : Czeisler et al

It is certified that error appears in the above-indentified patent and that said Letters Patent is hereby corrected as shown below:

Column 1, line 4, after the title, insert the following:

--This invention was made with government support under Grant Nos. 1 R01 AG04912-03 and 1 R01 HD20174-01 awarded by the National Institutes of Health. The government has certain rights in the invention.--.

Signed and Sealed this

Twenty-second Day of February, 1994

Attest:

BRUCE LEHMAN

*Attesting Officer*          *Commissioner of Patents and Trademarks*